United States Patent [19]

Foged et al.

[11] Patent Number: 6,110,470
[45] Date of Patent: *Aug. 29, 2000

[54] PASTEURELLA MULTOCIDA TOXIN DERIVATIVES

[75] Inventors: Niels Taekker Foged, Frederiksberg; Svend Petersen, Lyngby, both of Denmark

[73] Assignee: Akzo Nobel N.V., Arnhem, Netherlands

[*] Notice: This patent is subject to a terminal disclaimer.

[21] Appl. No.: 08/293,314

[22] Filed: Aug. 22, 1994

Related U.S. Application Data

[63] Continuation of application No. 07/582,945, filed as application No. PCT/DK89/00084, Apr. 11, 1989.

[51] Int. Cl.[7] .................... A61K 39/102; A61K 39/02; C07H 19/00; C07H 21/04
[52] U.S. Cl. .................. 424/255.1; 424/832; 424/93.2; 536/22.1; 536/23.1; 536/23.7; 536/24.32; 435/69.1; 435/69.3
[58] Field of Search .................... 536/22, 23.1, 23.7, 536/24.32, 22.1; 435/69.1, 69.3; 424/255.1, 93.2

[56] References Cited

U.S. PATENT DOCUMENTS 4,677,070  6/1987  Larrick et al. ..................... 435/240
5,369,019  11/1994  Foged et al. ..................... 435/69.3

FOREIGN PATENT DOCUMENTS 036 995  10/1981  European Pat. Off. .
085 469  8/1983  European Pat. Off. .
109 942  5/1984  European Pat. Off. .

OTHER PUBLICATIONS

Petersen et al, Infect & Immunity 57:3907–3913 1989.
Houghten et al Vaccines 86, pp. 21–25.
Chanten et al Journal of Microbiol 132:1089–97 1986.
Young et al PNAS 80:1194–1198 1983.
Itakura et al, Science 209:1401–1405 1980.
Manratis et al, Molecular Cloning: A Laboratory Manual, 1982 As Referenced by the State of the Art.
Foged et al Infect & Immunity 56:1901–6 1988.
Foged et al FEMS Microbiology Letters 43:45–57, 1987.
Petersen Molecular Microbiology 4:821–830, 1990.
Chemical Abstracts, vol. 107, (1987), Abstract No. 107:110786w, FEMS Microbiol. Lett. 1987, 43(1), 45–51 (Eng.).
Chanter et al. *J. Gen. Microbiol.*, Partial Purification of an Osteolytic Toxin from *Pasteurella multocida*, 132: 1089–97.
Kim et al. DIALOG, file BIOSIS, Dialog Accession No. 0017115392 (BIOSIS No. 83054453) Res Rep Rural Dev Adm (SUWEON) 28 (Livest. and Vet), "Studies on immunogenecity of Pasteurella . . . ", 77–93, 1986.

(List continued on next page.)

*Primary Examiner*—James C. Housel
*Assistant Examiner*—S. Devi
*Attorney, Agent, or Firm*—William M. Blackstone; Michael G. Sullivan

[57] ABSTRACT

A vaccine for immunizing animals against diseases caused by microorganisms producing an osteolytic toxin comprising an immunologically effective amount of a recombinant, immunogenic, detoxified *Pasteurella multocida* toxin or toxin analog, the vaccine being encoded by a nucleotide sequence coding for a *Pasteurella multocida* toxin or toxin analog which is inserted in an expression vector capable of replicating in a suitable host microorganism in which the said sequence may be expressed. Optionally, the produced toxin or toxin analog is subjected to posttranscriptional modifications to provide the detoxified toxin or toxin analog. Alternatively, the nucleotide sequence may be modified prior to insertion into the expression vector so as to provide the toxin or toxin analog in a detoxified form. Furthermore, the use of a monoclonal antibody against *Pasteurella multocida* toxin or toxin analog, a labelled DNA sequence homologous to a DNA sequence coding for a toxin or toxin analog, and the toxin or toxin analog per se as diagnostic agents are described.

13 Claims, 31 Drawing Sheets

OTHER PUBLICATIONS

Nakai, et al. Reconstructon of *Pasteurella multocida* dermonecrotic toxin from three polypeptides, *FEMS Microb. Lett.*, 44: 259–265 (1987).

Kodama DIALOG, file MEDLINE, Dialog Accession No. 04970881 (NLM Accession No. 83203881) Avian Dis, "Soluble fractions of *Pasteurella multocida*: . . . ", 27(1):283–91, (Jan.–Mar. 1983).

Lugtenberg DIALOG, file MEDLINE, Dialog Accession No. 05389686 (NLM Accession No. 85005686) Infect. Immun., "Atrophic rhinitis in swine: correlation of . . . ", 46(1):48–54, (Oct. 1984).

Pedersen et al. "The aetiological significance of *Bordetella bronchiseptica* and *P. multocida* in atrophic rhinitis of swine", Nord. Vet.–Med. 33, pp. 513–522, (1981).

Rutter et al. "Atrophic rhinitis in piglets: Differences in the pathogenicity of *Pasteurella multocida* in combined infections . . . ", Vet. Rec. 110: pp. 531–535, (1982).

Elling et al. "The pathogenesis of persistent turbinate atrophy induced by toxigenic *Pasteurella multocida* in pigs", Vet. Pathol. 22: pp. 469–474, (1985).

Pedersen, et al "Atrophic rhinitis in pigs: Proposal for a revised definition", Vet. Rec. 22: pp. 190–191, (1988).

Pedersen et al. "The pathogenesis of atrophic rhinitis in pigs induced by toxigenic *Pasteurella multocida*", J. Comp. Pathol. 94: pp. 203–214, (1984).

Foged et al. "Characterization and biological effect of the *P. multocida* toxin", FEMS Microbiol. Lett. 43: pp. 45–51, (1987).

Kamp et al. "Purification of a heat labile dermonecrotic toxin from culture fluid of *Pasteurella multocida*" Vet. Microbiol. 13: pp. 235–248, (1987).

Nakai et al. "Purification of dermonecrotic toxin from a sonic extract of *Pasteurella multocida* SP–72 serotype D", *Infect. Immun.* ,46: 429–434, (1984).

Trummel, et al. Stimulation of bone resorption by a factor from *Actinomyces viscosus*, J. Perdont, Res. 14: pp. 263–264, (1979).

Price "Structure and function of vitamin K–dependent bone proteins", In: Christiansen, et al. (eds.), Osteoporosis, Norhaven A/S, Viborg, Denmark, pp. 656–663, (1987).

Nielsen et al. Production of toxin in strains previously classified as *P. multocida*, Acta Path. Microbiol. Immunol. Scand. Sec. B, 94: pp. 203–204, (1986).

Rutter "Virulence of *Pasteurella multocida* in atrophic rhinitis of gnotobiotic pigs infected with *Bordetella bronchiseptica*", Res. Vet. Sci. 34: pp. 287–295, (1983).

Kume et al. "Dissociation of *Pasteurella multocida* Dermonecrotic Toxin into Three Polypeptide Fragments",*Japanese Journal Vet. Sci.*, 47(5): 829–833, (1985).

Nakai et al. "Characterization of dermonecrotic toxin produced serotype D strains of *Pasteurella multocida*", Am. J. Vet. Res., vol. 45 (11), pp. 2410–2413, (1984).

Nakai et al. *Research in Vet Science*, 42:232–237, (1987).

Young et al. "Efficient Isolution of Genes Using Antibody Probes", *PNAS*, 80:1194–1198 (1983).

Itakura et al. "Chemical DNA Synthesis and Recombinant DNA Studies", *Science*, 209:1401–1405, (1980).

International Search Report (Swedish), 2 pp.

```
AACAAGGGAAAATAGCTAGATTAGACGATATCGATAATATCATAAATAATATTTAAAAAT
         10        20        30        40        50        60

TACGCCCCTTGACCTAGAGGGGCTTTTTTATTACATCAAAAAAATAAACCCAAACACTGC
         70        80        90       100       110       120

GAATGTTTGGGGTTTTATTTATAACCAAAATACATTAATATGTTTATTAAGTAAGCATTA
        130       140       150       160       170       180

M   K   T   K   H   F   F   N
TCTTACTTTAGGAATAAACTAACATAGAGGTTATGGATATGAAAACAAAACATTTTTTTA
        190       200       210       220       230       240

S   D   F   T   V   K   G   K   S   A   D   E   I   F   R   R   L   C   T   D

ACTCAGATTTTACTGTAAAAGGAAAAAGTGCCGATGAAATTTTTAGAAGATTGTGTACTG
        250       260       270       280       290       300

H   P   D   K   Q   L   N   N   V   K   W   K   E   V   F   I   N   R   F   G

ATCATCCTGACAAGCAATTAAACAATGTAAAATGGAAAGAAGTTTTTATTAATCGTTTTG
        310       320       330       340       350       360

Q   M   M   L   D   T   P   N   P   R   K   I   V   E   K   I   I   N   E   G

GTCAGATGATGCTAGATACTCCTAATCCGAGAAAGATTGTAGAAAAAATTATTAATGAAG
        370       380       390       400       410       420
```

GGCTTGAAAAACAAGGCCTGAAAAATATAGATCCTGAAAACACATATTTCAACATTTTTT
      430       440       450       460       470       480

S   S   D   S   S   D   G   N   V   F   H   Y   N   S   L   S   E   S   Y   R

CATCTTCTGACAGCTCCGATGGGAACGTTTTTCATTATAACTCTTTATCAGAATCCTATC
      490       500       510       520       530       540

V   T   D   A   C   L   M   N   I   F   V   E   R   Y   F   D   D   W   D   L

GAGTTACTGATGCCTGCCTAATGAATATTTTTGTGGAGCGTTATTTTGATGATTGGGACT
      550       560       570       580       590       600

L   N   S   L   A   S   N   G   I   Y   S   V   G   K   E   G   A   Y   Y   P

TGCTAAATAGCTTAGCCAGTAATGGAATATATTCAGTAGGAAAAGAAGGAGCTTATTATC
      610       620       630       640       650       660

D   H   D   Y   G   P   E   Y   N   P   V   W   G   P   N   E   Q   I   Y   H

CTGATCATGATTATGGTCCAGAATATAACCCTGTTTGGGGACCAAACGAACAAATTTACC
      670       680       690       700       710       720

S   R   V   I   A   D   I   L   Y   A   R   S   V   W   D   E   F   K   K   Y

ATTCTAGAGTGATTGCAGATATCCTTTATGCTCGCTCCGTATGGGATGAATTTAAAAAAT
      730       740       750       760       770       780

F   M   E   Y   W   Q   K   Y   A   Q   L   Y   T   E   M   L   S   D   T   F

ACTTCATGGAGTATTGGCAAAAATATGCTCAGCTTTATACCGAAATGTTATCTGATACAT
      790       800       810       820       830       840
```

TTCTTGCAATGGCTATTCAGCAATATACACGACAAACGCTTACTGATGAAGGCTTTCTTA
       850       860       870       880       890       900

V   C   N   T   Y   Y   G   N   K   E   E   V   Q   I   T   L   L   D   I   Y

TGGTTTGTAACACATATTATGGCAATAAGGAAGAAGTTCAAATAACTCTACTAGATATCT
       910       920       930       940       950       960

G   Y   P   S   T   D   I   I   C   I   E   Q   K   G   L   P   T   P   K   V

ATGGATACCCTTCCACTGATATAATTTGTATAGAGCAAAAAGGGCTTCCTACTCCTAAAG
       970       980       990      1000      1010      1020

I   L   Y   I   P   G   G   T   Q   P   F   V   E   F   L   N   T   D   D   L

TGATACTTTACATTCCTGGAGGAACACAACCATTTGTTGAATTTCTTAATACAGATGATC
      1030      1040      1050      1060      1070      1080

K   Q   W   I   A   W   H   L   K   D   N   K   H   M   V   R   F   R   K   H

TGAAACAATGGATTGCATGGCATTTAAAAGATAACAAACATATGGTCCGATTCCGCAAAC
      1090      1100      1110      1120      1130      1140

F   S   L   K   Q   R   Q   E   G   E   T   F   T   G   I   D   K   A   L   Q

ATTTCTCGCTAAAACAACGTCAGGAAGGAGAAACGTTTACAGGTATAGATAAAGCACTTC
      1150      1160      1170      1180      1190      1200

Y   I   A   E   E   S   P   E   W   P   A   N   K   Y   I   L   Y   N   P   T

AATATATTGCAGAAGAGTCCCCTGAATGGCCTGCCAATAAATACATCCTTTATAATCCGA
      1210      1220      1230      1240      1250      1260
```

CACATTTAGAAACAGAAAATTTATTTAACATCATGATGAAGCGAACAGAACAGCGGATGC
     1270      1280      1290      1300      1310      1320

E   D   S   D   V   Q   I   R   S   N   S   E   A   T   R   D   Y   A   L   S

TTGAAGATAGTGATGTACAGATTAGATCAAATTCAGAAGCTACCCGTGACTATGCTCTTT
     1330      1340      1350      1360      1370      1380

L   L   E   T   F   I   S   Q   L   S   A   I   D   M   L   V   P   A   V   G

CATTACTCGAAACCTTTATTTCACAGTTATCTGCAATAGATATGTTAGTACCAGCAGTAG
     1390      1400      1410      1420      1430      1440

I   P   I   N   F   A   L   S   A   T   A   L   G   L   S   S   D   I   V   V

GTATCCCAATTAATTTTGCCCTATCAGCTACAGCATTAGGACTTAGCTCGGATATTGTAG
     1450      1460      1470      1480      1490      1500

N   G   D   S   Y   E   K   R   K   Y   G   I   G   S   L   V   Q   S   A   L

TTAATGGAGATTCATATGAAAAGAGAAAATATGGAATTGGGTCCTTAGTGCAATCTGCAT
     1510      1520      1530      1540      1550      1560

F   T   G   I   N   L   I   P   V   I   S   E   T   A   E   I   L   S   S   F

TATTCACAGGAATTAATCTTATTCCAGTTATTTCGGAAACCGCAGAAATTTTATCTTCTT
     1570      1580      1590      1600      1610      1620

S   R   T   E   E   D   I   P   A   F   F   T   E   E   Q   A   L   A   Q   R

TCTCTAGAACAGAAGAAGATATTCCAGCTTTTTTCACTGAAGAACAAGCTTTAGCTCAAC
     1630      1640      1650      1660      1670      1680

```
GCTTTGAAATAGTAGAAGAAGAATTACATTCTATCTCACCTGATGATCCTCCTCGAGAAA
     1690      1700      1710      1720      1730      1740

T  D  E  N  L  H  K  I  R  L  V  R  L  N  N  E  N  Q  P  L

TTACTGACGAAAATTTACATAAAATTCGTCTGGTACGTCTTAACAATGAAAATCAACCTT
     1750      1760      1770      1780      1790      1800

V  V  L  R  R  L  G  G  N  K  F  I  R  I  E  P  I  T  F  Q

TAGTTGTGTTACGAAGATTAGGAGGAAATAAATTTATCAGAATCGAGCCTATAACATTCC
     1810      1820      1830      1840      1850      1860

E  I  K  G  S  L  V  S  E  V  I  N  P  V  T  N  K  T  Y  Y

AGGAAATAAAAGGTTCTTTAGTAAGTGAAGTTATAAATCCAGTGACTAATAAAACGTACT
     1870      1880      1890      1900      1910      1920

V  S  N  A  K  L  L  G  G  S  P  Y  S  P  F  R  I  G  L  E

ACGTAAGCAATGCTAAACTATTAGGGGGCTCTCCTTATAGTCCTTTCCGTATTGGATTAG
     1930      1940      1950      1960      1970      1980

G  V  W  T  P  E  V  L  K  A  R  A  S  V  I  G  K  P  I  G

AAGGTGTTTGGACACCAGAGGTATTAAAAGCAAGAGCTTCCGTTATTGGAAAGCCTATTG
     1990      2000      2010      2020      2030      2040

E  S  Y  K  R  I  L  A  K  L  Q  R  I  H  N  S  N  I  L  D

GAGAATCATATAAAAGAATATTAGCCAAACTACAAAGAATACATAACAGTAATATCTTAG
     2050      2060      2070      2080      2090      2100

```
ATGAGCGACAAGGTTTAATGCATGAACTCATGGAGCTTATTGATCTTTATGAAGAATCGC
     2110      2120      2130      2140      2150      2160

P   S   S   E   R   L   N   A   F   R   E   L   R   T   Q   L   E   K   A   L

AACCTTCTTCAGAGCGTTTGAATGCTTTTCGTGAACTGCGTACTCAATTAGAAAAAGCGC
     2170      2180      2190      2200      2210      2220

Y   L   P   E   M   E   A   L   K   K   Q   I   L   Q   I   P   N   K   G   S

TTTATCTTCCTGAAATGGAAGCATTAAAAAAACAAATACTACAGATTCCTAACAAAGGTT
     2230      2240      2250      2260      2270      2280

G   A   A   R   F   L   L   R   T   A   M   N   E   M   A   G   K   T   S   E

CTGGTGCCGCTCGATTTTTACTTCGTACAGCCATGAATGAAATGGCTGGAAAAACCAGTG
     2290      2300      2310      2320      2330      2340

S   T   A   D   L   I   R   F   A   L   Q   D   T   V   I   S   A   P   F   R

AAAGCACGGCTGATTTAATACGCTTTGCCTTGCAAGATACAGTAATTTCAGCGCCTTTTC
     2350      2360      2370      2380      2390      2400

G   Y   A   G   A   I   P   E   A   I   D   F   P   V   K   Y   V   I   E   D

GCGGATATGCTGGTGCGATTCCAGAGGCAATAGACTTTCCTGTAAAATATGTAATAGAAG
     2410      2420      2430      2440      2450      2460

I   S   V   F   D   K   I   Q   T   N   Y   W   E   L   P   A   Y   E   S   W

ACATATCTGTATTTGATAAAATACAGACAAATTACTGGGAACTTCCTGCTTATGAAAGCT
     2470      2480      2490      2500      2510      2520

N   E   G   S   N   S   R   L   L   P   G   L   L   R   E   S   Q   S   K   G

GGAACGAAGGAAGTAATAGCCGATTACTGCCTGGTTTGTTACGTGAATCGCAAAGCAAGG
```

GGATGTTAAGTAAGTGTCGTATCATAGAAAATAGCCTTTATATTGGACATAGCTATGAAG
                2590        2600        2610        2620        2630        2640

M   F   Y   S   I   S   P   Y   S   N   Q   V   G   G   P   Y   E   L   Y   P

AAATGTTTTACAGCATTTCTCCATATTCAAACCAGGTTGGAGGGCCTTATGAATTATATC
                2650        2660        2670        2680        2690        2700

F   T   F   F   S   M   L   Q   E   V   Q   G   D   L   G   F   E   Q   A   F

CTTTCACTTTTTTCAGTATGCTTCAAGAAGTACAAGGTGATTTAGGATTTGAGCAGGCCT
                2710        2720        2730        2740        2750        2760

A   T   R   N   F   F   N   T   L   V   S   D   R   L   S   L   M   E   N   T

TTGCCACACGTAACTTTTTCAATACTCTTGTTTCTGATCGACTATCCTTAATGGAAAATA
                2770        2780        2790        2800        2810        2820

M   L   L   T   E   S   F   D   Y   T   P   W   D   A   I   Y   G   D   I   N

CGATGTTACTTACAGAAAGTTTTGATTATACACCTTGGGATGCTATTTATGGAGATATTA
                2830        2840        2850        2860        2870        2880

Y   D   E   Q   F   A   A   M   S   I   N   E   R   I   E   K   C   M   N   T

ATTATGATGAACAATTTGCTGCAATGTCTATTAATGAACGCATAGAAAAATGTATGAATA
                2890        2900        2910        2920        2930        2940

Y   R   G   V   A   F   Q   N   S   S   K   S   I   D   F   F   L   N   N   L

CCTATAGAGGTGTGGCATTCCAAAACTCTTCAAAAAGTATTGACTTTTTCCTAAATAATC
                2950        2960        2970        2980        2990        3000
```

TAACCACATTCATTGATAATGGACTAACCGAAATTGCTATATCTGATTTACCGTATGATA
        3010      3020      3030      3040      3050      3060

V   Q   Q   E   I   S   Q   F   L   Q   G   S   N   E   W   K   T   L   D   A

TTGTGCAACAAGAAATCTCTCAATTCTTACAAGGAAGTAATGAATGGAAAACACTTGATG
        3070      3080      3090      3100      3110      3120

M   L   F   N   L   D   K   G   D   I   N   G   A   F   R   K   L   L   Q   S

CCATGTTATTTAACTTAGATAAAGGAGATATTAATGGTGCTTTCAGAAAGCTTCTGCAAT
        3130      3140      3150      3160      3170      3180

A   K   D   N   N   I   K   F   R   A   I   G   H   S   D   N   S   V   P   P

CAGCAAAAGATAATAATATAAAATTTAGAGCTATAGGGCATTCAGATAATTCTGTTCCGC
        3190      3200      3210      3220      3230      3240

F   N   N   P   Y   K   S   L   Y   Y   K   G   N   I   I   A   E   A   I   E

CATTTAATAACCCTTATAAGTCTTTATATTATAAAGGAAATATAATAGCTGAAGCAATTG
        3250      3260      3270      3280      3290      3300

K   L   D   R   E   G   Q   K   F   V   V   F   A   D   S   S   L   L   N   S

AAAAACTAGATCGAGAAGGTCAAAAATTTGTTGTATTTGCTGATAGTTCTCTGCTCAACA
        3310      3320      3330      3340      3350      3360

T   P   G   T   G   R   P   M   P   G   L   V   Q   Y   L   K   I   P   A   T

GCACGCCTGGGACAGGTCGTCCTATGCCAGGACTAGTTCAATATTTAAAAATACCAGCAA
        3370      3380      3390      3400      3410      3420
```

CTGTAGTAGATAGCGATGGTGCATGGCAATTTCTTCCAGATGTAGCTTCAAGCAGAGTTC
      3430      3440      3450      3460      3470      3480

I   E   V   T   E   L   E   N   W   Q   V   L   T   P   P   Q   G   K   I   L

CTATTGAAGTTACAGAGTTAGAAAATTGGCAAGTCTTAACTCCTCCACAAGGTAAGATTC
      3490      3500      3510      3520      3530      3540

G   L   K   Q   F   K   L   T   A   G   F   P   T   E   Q   S   R   L   P   L

TTGGATTAAAGCAATTTAAGTTAACGGCAGGTTTTCCAACAGAACAAAGTCGCTTACCTC
      3550      3560      3570      3580      3590      3600

L   E   N   S   V   S   E   D   L   R   E   E   L   M   Q   K   I   D   A   I

TTTTAGAGAATTCGGTTTCTGAAGATTTAAGGGAAGAATTAATGCAAAAGATTGATGCAA
      3610      3620      3630      3640      3650      3660

K   N   D   V   K   M   N   S   L   V   C   M   E   A   G   S   C   D   S   V

TAAAAAATGATGTGAAAATGAATAGTTTAGTGTGTATGGAAGCTGGCTCTTGTGATTCAG
      3670      3680      3690      3700      3710      3720

S   P   K   V   A   A   R   L   K   D   M   G   L   E   A   G   M   G   A   S

TAAGCCCTAAGGTAGCTGCCCGTCTTAAAGATATGGGGTTAGAAGCTGGGATGGGTGCTT
      3730      3740      3750      3760      3770      3780

I   T   W   R   R   E   G   G   M   E   F   S   H   Q   M   H   T   T   A

CTATTACCTGGTGGAGACGTGAAGGCGGGATGGAATTTTCACATCAGATGCATACTACTG
      3790      3800      3810      3820      3830      3840
```

CTTCCTTTAAATTTGCTGGTAAAGAGTTTGCCGTGGATGCTTCACATTTACAATTTGTAC
    3850      3860      3870      3880      3890      3900

D   Q   L   D   T   T   I   L   I   L   P   V   D   D   W   A   L   E   I   A

ACGACCAATTAGATACAACTATCCTGATACTACCTGTAGATGATTGGGCTTTAGAAATAG
    3910      3920      3930      3940      3950      3960

Q   R   N   R   A   I   N   P   F   V   E   Y   V   S   K   T   G   N   M   L

CTCAAAGAAATCGGGCTATTAATCCTTTTGTGGAATATGTTAGTAAAACAGGAAACATGT
    3970      3980      3990      4000      4010      4020

A   L   F   M   P   P   L   F   T   K   P   R   L   T   R   A   L

TAGCACTCTTCATGCCTCCTCTTTTCACAAAGCCTCGCTTAACAAGAGCACTATAACTAA
    4030      4040      4050      4060      4070      4080

TTAAAAACTGTATTAAAGCCTTATATTATAAGGCTTTAATTTTCTTTCAAGAATTATTAA
    4090      4100      4110      4120      4130      4140

GTAGAAGAATCAAAATCAATGAGATAGATAAAATCAAATGTTATTACCAATACAACTTTC
    4150      4160      4170      4180      4190      4200

TTAAGTATACTTTTTGAATTTTTTGCGTTAATAAATTTATAATACCCTTAACTCAATAAA
    4210      4220      4230      4240      4250      4260

AGAAGTTATTGAGAAGTTTAAATCTTGTGAGCAAGATGAAGATATAATTTCAGCAATCGA
    4270      4280      4290      4300      4310      4320

TCTTATTAGCGCTTCATATAGAAGGGCTGTGGATGCAGTGGAACAAAGATTCGGTTCTAG
    4330      4340      4350      4360      4370      4380
```

FIG. 10j

PASTEURELLA MULTOCIDA TOXIN DERIVATIVES

This application is a continuation of application Ser. No. 07/582,945, filed Oct. 12, 1990 which is the national stage of PCT/DK89/00084 filed Apr. 11, 1989.

FIELD OF INVENTION

The present invention relates to a vaccine for immunizing animals against diseases caused by microorganisms producing an osteolytic toxin, a DNA sequence encoding a *Pasteurella multocida* toxin useful for producing the toxin and as a diagnostic agent, methods of producing and isolating a *P. multocida* toxin, use of a *P. multocida* toxin, a monoclonal antibody directed against a *P. multocida* toxin, a diagnostic agent comprising said monoclonal antibody and the use of said monoclonal antibody for a variety of diagnostic and other purposes.

TECHNICAL BACKGROUND

Atrophic rhinitis is a disease which profoundly affects the bone structure of, the porcine snout. The etiological agent which is currently considered to be the cause of growth retarding progressive atrophic rhinitis is toxigenic (toxin-producing) strains of *P. multocida* which colonize the nasal cavity of pigs (Pedersen and Barfod, 1981, (ref. 1), Rutter and Rojas, 1982, (ref. 2), Elling and Pedersen, 1985, (ref. 3), Pedersen et al. 1988 (ref. 4). It has been shown that the nasal mucosa are more easily colonized by *P. multocida* when the resistance to infection is lower such as when the pigs are concomitantly infected with *Bordetella bronchiseptica* or when the nasal mucosa are exposed to a mild chemical irritant (cf. Pedersen and Elling, 1984, (ref. 5).

The pathological effects of *P. multocida* infection may be ascribed to a toxin produced by this bacterium. The toxin which has an apparent molecular weight of 143 kd and an actual molecular weight of 146.5 kd induces bone resorption (osteolysis) of the nasal turbinates and other bone structures in the nasal cavity by stimulating osteoclast activity in porcine turbinate bones, and causes impaired osteoblastic bone formation.

The disease is of major economic importance to pig breeders all over the world, since apart from the pathological effects on the nasal (and occasionally facial) bones noted above, it causes a slower growth rate of the infected pigs and consequently higher production costs. Attempts have therefore been made to reduce the occurrence and the significance of *P. multocida* infection, for instance by the establishment of SPF (specific pathogen free) pigs via cesarean section, or by antibiotic treatment of infected animals or prophylactic vaccination.

Known vaccines for the immunization of animals, principally pigs, against diseases ascribable to *P. multocida* infection, especially atrophic rhinitis, comprise killed *P. multocida* cells optionally combined with killed *Bordetella bronchiseptica* cells (cf. EP 85 469) and/or an inactivated (usually by heat treatment or addition of formaldehyde) toxin-containing extract of toxigenic *P. multocida*. Vaccines of the latter type are commercially available from Northern Drugs & Chemicals Ltd., Copenhagen, Denmark, under the trademark Atrinord®, as well as from Intervet International BV, Boxmeer, Holland, under the trademark Nobi-vacART®.

The present inventors contemplate that an improved immunogenic effect relative to the known vaccine preparations may be obtained by using a purified and suitably modified toxin preparation for vaccination purposes either to replace the conventional vaccines or as a constituent thereof.

The purification of *P. multocida* toxin has previously been described. Thus, Foged et al., 1987, (ref. 6) disclose the purification of the toxin by chromatography and polyacrylamide gel electrophoresis. The purified toxin is used solely for studying its toxic and pathological effects. Kamp et al., 1987, (ref. 7) also disclose the purification of the *P. multocida* toxin for the purpose of clinical studies. They suggest that the purified toxin may be used as an antigen to raise specific antibodies useful for serological tests. Nakai et al., 1984, (ref. 8) disclose a method of purifying the *P. multocida* toxin by chromatography and polyacrylamide gel electrophoresis. They further disclose the production of polyclonal antibodies directed against the purified toxin which they use to analyse the purity of the purified toxin. It is suggested that the antibodies may be used to further study the role of the toxin in atrophic rhinitis.

None of these publications suggest the use of a purified toxin as a component of a vaccine for immunizing animals against Pasteurella infection, and this is believed to be a novel concept.

SUMMARY OF THE INVENTION

Accordingly, in one aspect the present invention relates to a vaccine for immunizing an animal, including a human being, against diseases caused by microorganisms producing an osteolytic toxin, the vaccine comprising an immunogenically effective amount of a recombinant, immunogenic, detoxified *P. multocida* toxin or toxin analogue together with an immunologically acceptable carrier or vehicle.

For the preparation of the known vaccines, a toxigenic Pasteurella strain is cultivated and the toxin is isolated from the culture medium or from a bacterial extract followed by detoxification by, for instance, thermal or chemical treatment. Compared to this procedure, the production of the toxin or toxin analogue by recombinant DNA techniques has a number of advantages: it is possible to produce the toxin or toxin analogue by growing a non-pathogenic organism, the toxin or toxin analogue may be produced in higher quantities than those produced by wild-type *P. multocida* strains, for instance by using a strong promoter to induce a high level of expression of the toxin gene or by using a high copy number vector for cloning the toxin gene, and it is possible to produce the toxin or toxin analogue in a detoxified form, e.g. by subjecting the gene encoding the toxin to treatment with a mutagen, or by deleting a part of the nucleotide sequence coding for the toxin or toxin analogue, substituting one or more nucleotides in the sequence, etc. The recombinant toxin or toxin analogue may be used in substantially pure form in the vaccine of the invention but may also be employed as a crude or partially purified preparation.

In the present context, the term "substantially pure" is understood to mean that the vaccine is substantially free from other immunogenically active components the presence of which might give rise to adverse immune reactions in the animals immunized with the vaccine and, most importantly, that no other components of the microorganisms producing the toxin or toxin analogue, such as cell debris or cellular proteins apart from the toxin or toxin analogue itself or a protein or polypeptide to which the toxin or toxin analogue is fused (vide below) are present in the vaccine preparation. A high purity of the detoxified toxin or toxin analogue is believed to result in a high antitoxin response on immunization with the vaccine of the invention and a lower dosage of the toxin or toxin analogue may consequently be required for immunization purposes than that used in crude or partially purified vaccine preparations. A substantially pure toxin or toxin analogue has the added advantage that the exact concentration thereof in a given vaccine preparation is known so that an exact dosage may be administered to the animal in question.

The microorganism producing an osteolytic toxin (i.e. a toxin directly or indirectly involved in bone resorption) against which the vaccine confers immunity is preferably *P. multocida*. Other microorganisms which have shown osteolytic effects or regulation of specific markers of bone metabolism are e.g. *Actinomyces viscosus* and *Bordetella pertussis* (Trummel et al., 1979, (ref. 9) and Price (ref. 10).

Due to the toxic activity of the *P. multocida* toxin, it is not possible to use the native toxin in a vaccine of the invention. Rather, it must be present in detoxified form. The term "detoxified" should be understood to mean that the toxic activity has been removed from at least a sufficient number, but not necessarily all, of the toxin molecules present in the vaccine preparation so that the vaccine, when administered to an animal to be immunized, will not produce any adverse toxic effects in the animal in question, while still giving rise to a satisfactory immune response.

The detoxification of the *P. multocida* toxin or toxin analogue may be carried out in a variety of ways. Thus, it is possible to subject the toxin or toxin analogue to thermal treatment, the toxin being known to be heat labile and to be inactivated (i.e. detoxified) at 70° C. Furthermore, the toxin or toxin analogue may be subjected to treatment with a chemical, such as formaldehyde, glutaraldehyde or a suitable proteolytic enzyme, e.g. trypsin. Detoxification may also be brought about by mutagenizing the gene coding for the *P. multocida* toxin or toxin analogue by means of, for instance, ultraviolet radiation, ionizing radiation or a chemical mutagen such as mitomycin C, 5-bromouracil, methylmethane sulphonate, nitrogen mustard or a nitrofuran. Furthermore, the toxin may be detoxified by substitution, deletion, addition or insertion of one or more amino acids in the toxin or toxin analogue, or by substitution, addition, deletion or insertion of one or more base pairs in the nucleotide sequence coding for the toxin or toxin analogue, or a combination of these measures.

In contrast to detoxification by thermal or chemical treatment, the genetic procedure has the obvious advantage of resulting in a uniform population of equally detoxified molecules.

It should be noted that the terms "substitution, deletion, addition or insertion" should be interpreted with reference to the full-length toxin protein. Thus, "substitution" is intended to mean the replacement of any one or more amino acids or nucleotides in the full amino acid or nucleotide sequence with one or more others, "addition" is understood to mean the addition of one or more amino acids or nucleotides at either end of the full amino acid or nucleotide sequence, "insertion" is intended to mean the introduction of one or more amino acids or nucleotides within the full amino acid or nucleotide sequence, and "deletion" is intended to indicate that one or more amino acids or nucleotides have been deleted from the full amino acid or nucleotide sequence whether at either end of the sequence or at any suitable point within it. It should be understood that the detoxification of the toxin or toxin analogue may also be brought about by a combination of two or more of these procedures.

The term "toxin analogue" is used in the present context to indicate a protein or polypeptide of a similar amino acid composition or sequence as the *P. multocida* toxin, allowing for variations which do not have an adverse effect on the immunogenicity of the analogue.

The analogous polypeptide or protein may be derived from a microorganism of another species than *P. multocida* or may be partially or completely of synthetic origin. The analogous polypeptide or protein may also be one which comprises at least one epitope reactive with anti-*P. multocida* toxin antibodies found in samples from individuals with atrophic rhinitis and/or which elicits antibodies reactive with native *P. multocida* toxin. The term is further intended to mean any immunogenic subsequence, functional equivalent or derivative of the toxin.

The term "immunogenic subsequence" is intended to indicate a sequence of the full-length toxin which from the outset is produced in a truncated form relative to the full-length toxin protein or which subsequent to production of the full-length protein is generated, for instance by proteolytic cleavage thereof or by expression of a nucleotide sequence shorter than the full nucleotide sequence encoding *P. multocida* toxin. The minimum subsequence is one which at least comprises a relevant epitope of the toxin, i.e. an epitope which gives rise to a relevant immune response in an animal immunized with the vaccine of the invention.

The term "functional equivalent" is intended to include all immunogenically active substances with the ability to evoke an immune response in animals to which a vaccine containing the equivalent has been administered which is similar to the immune response evoked by the detoxified *P. multocida* toxin, in that it is able to confer immunity to diseases caused by microorganisms producing an osteolytic toxin. The functional equivalent may be derived from a microorganism of another species than *P. multocida* or may partially or completely be of synthetic origin. It should be understood that the similarities between the *P. multocida* toxin and the functional equivalent are qualitative rather than quantitative, relating to the nature rather than the level of activity of the functional equivalent.

The term "derivative" is understood to mean a modification of the toxin such as one produced by substitution, insertion, addition or deletion of one or more amino acids or nucleotides or a combination of these measures, as defined above, or by fusion with another polypeptide.

In a further aspect, the present invention relates to a DNA fragment comprising a nucleotide sequence coding for a *P. multocida* toxin or toxin analogue, as defined above. The DNA fragment may for instance be used in a method of preparing the toxin or toxin analogue by recombinant DNA techniques or as a diagnostic agent (i.e. a DNA probe).

In a still further aspect, the present invention relates to a monoclonal antibody which is directed against or reactive with a *P. multocida* toxin or a toxin analogue as defined above, or a fragment of said antibody. It should be noted that the antibody may be reactive with both the toxic and detoxified toxin, thus making it useful for a variety of diagnostic, immunization and isolation purposes as will be described in further detail below.

DETAILED DISCLOSURE OF THE INVENTION

The toxin produced by *P. multocida* (in the following occasionally abbreviated to PMT) which, as noted above, is generally believed to be the causative agent of porcine atrophic rhinitis, has in the prior literature been variously termed "dermonecrotic toxin", "osteolytic toxin", "turbinate atrophy toxin" and "heat labile exotoxin", but it would appear to be the same toxin as the amino acid composition, isoelectric point and biological activities of the variously termed toxins show basic similarities, although minor variations in the properties of toxins isolated from different strains of P. multocida appear to exist. The estimated amino acid composition of PMT (as deduced from the DNA sequence) is as follows:

| | |
|---|---|
| Ala is found 76 times | = 5.91% |
| Cys is found 8 times | = 0.62% |
| Asp is found 71 times | = 5.53% |
| Glu is found 100 times | = 7.78% |
| Phe is found 69 times | = 5.37% |
| Gly is found 71 times | = 5.53% |
| His is found 19 times | = 1.48% |
| Ile is found 92 times | = 7.16% |
| Lys is found 70 times | = 5.45% |
| Leu is found 127 times | = 9.88% |
| Met is found 36 times | = 2.80% |
| Asn is found 73 times | = 5.68% |
| Pro is found 62 times | = 4.82% |
| Gln is found 56 times | = 4.36% |
| Arg is found 58 times | = 4.51% |
| Ser is found 97 times | = 7.55% |
| Thr is found 66 times | = 5.14% |
| Val is found 63 times | = 4.90% |
| Trp is found 18 times | = 1.40% |
| Tyr is found 53 times | = 4.12% |

The total number of amino acid residues is 1285, and the full-length toxin has a molecular weight of 146.5 kd.

The recombinant toxin or toxin analogue used in the vaccine of the invention may more specifically be one encoded by a DNA sequence substantially as shown in FIGS. 10 (a)–(j) (SEQ ID NO:1) or a subsequence thereof encoding an immunogenic subsequence of the toxin or toxin analogue. It should be noted that the amino acid sequence deduced from the DNA sequence is also shown in FIGS. 10 (a)–(j) (SEQ ID NO:2) above the DNA sequence. A suitable analogue may be one which has a DNA sequence which differs from that of the native toxin by one or more base pairs and which may be derived by substituting one or more nucleotides in the toxin DNA sequence either giving rise to the same amino acid sequence, but where the nucleotide substitutions make the sequence conform to the codon usage of the microorganism in which the sequence is inserted, or giving rise to a somewhat different amino acid sequence which, however, is functionally similar to that of the native toxin.

Apart from the toxin or toxin analogue as defined above, the vaccine of the invention also comprises an immunologically acceptable carrier or vehicle. This vehicle may be any vehicle usually employed in the preparation of vaccines, e.g. a diluent such as isotonic saline, suspending agent etc. The vaccine may be prepared by mixing an immunogenically effective amount of the toxin or toxin analogue with the vehicle in an amount resulting in the desired concentration of the toxin or toxin analogue in the vaccine preparation. Although the amount of toxin or toxin analogue per unit dose of the vaccine will differ according to the age of the animals to be immunized (for instance according to whether sows or piglets are to be immunized against P. multocida), the route and form of administration, and the immunogenicity of the particular toxin present in the vaccine, a suitable amount of toxin or toxin analogue is contemplated in the range of 0.1–500 μg per dosage of the vaccine.

The vaccine may further comprise an adjuvant in order to increase the immunogenicity of the vaccine preparation. The adjuvant may be selected from Freund's complete or incomplete adjuvant, aluminium hydroxide, Bordetella pertussis, a saponin, a muramyl dipeptide, an iscom (immune stimulating complex; cf. for instance EP 109 942) and an oil, such as a vegetable oil, e.g. peanut oil, or a mineral oil, e.g. silicone oil.

In some cases it may be advantageous to couple the toxin or toxin analogue to a carrier, in particular a macromolecular carrier. The carrier is usually a polymer to which the toxin is bound by hydrophobic non-covalent interaction, such as a plastic, e.g. polystyrene, or a polymer to which the toxin is covalently bound, such as a polysaccharide, or a polypeptide, e.g. bovine serum albumin, ovalbumin or keyhole limpet hemocyanin. The carrier should preferably be non-toxic and non-allergenic. The toxin or toxin analogue may be multivalently coupled to the macromolecular carrier as this provides an increased immunogenicity of the vaccine preparation. It is also contemplated that the toxin or toxin analogue may be presented in multivalent form by polymerizing the toxin or toxin analogue with itself.

In a particular embodiment of the vaccine of the present invention, the toxin or toxin analogue as defined above is fused to another polypeptide. Techniques for preparing fused polypeptides are known from, e.g. Casadaban and Cohen, 1983, (ref. 11). Alternatively, the fusion may be provided by fusing the nucleotide sequence encoding the toxin to a nucleotide sequence encoding another polypeptide so that the fused nucleotide sequence, when inserted in an appropriate vector, is expressed as a fusion polypeptide on transformation of the vector to a suitable microorganism and growth of the microorganism under conditions favorable to the expression of the fused sequence. The polypeptide to which the toxin is fused may, for instance, be a carrier polypeptide as suggested above, lysozyme or another immunogenic peptide such as a Ty protein from Saccharomyces cerevisiae, protein A from Staphylococcus aureus, Hepatitis B core antigen, etc.

It is also contemplated that the vaccine may be in the form of tablet, granule or capsule intended for oral administration since there is some evidence that immunogens may be absorbed through the intestinal wall and stimulate B-lymphocytes which then migrate to local epithelial regions where they transform into immunoglobulin-secreting plasma cells. An oral vaccine should be provided with an enteric coating in order to protect the toxin or toxin analogue from substances present in gastric juice which might be deleterious to the toxin or toxin analogue, such as pepsin. The enteric coating may be selected from shellac, cellulose acetate esters such as cellulose acetate phthalate, hydroxypropylmethyl cellulose esters such as hydroxypropylmethyl cellulose phthalate, polyvinyl acetate esters such as polyvinyl acetate phthalate, and polymers of methacrylic acid and (meth)acrylic acid esters. Newly developed methods of encapsulations, based on microspheres with a diameter of about 5–15 μm are of special interest since such particles containing an immunogenic substance after administration will be selectively delivered to Peyers's patches thereby providing immunity on mucosal surfaces. Stimulation of the immune response on respiratory mucosal surfaces may also be obtained through intranasal immunizations. (Mestecky, 1987, (ref. 12).

The DNA molecule or DNA fragment of the invention comprising the nucleotide sequence encoding the toxin or toxin analogue may be derived from complementary cDNA obtained by preparing a cDNA library on the basis of mRNA from a toxin-producing P. multocida strain by standard methods. Alternatively and preferably, the nucleotide sequence may be derived from a P. multocida genome, by screening for genomic sequences hybridizing to a DNA probe prepared on the basis of the full or partial amino acid sequence of the toxin in accordance with established procedures or by establishing a toxin gene library and screening for toxin-producing clones by means of a toxin-specific antibody (for a more detailed description of this procedure, see Example 4). In the case of PMT, it is not possible to prepare a DNA probe on the basis of its N-terminal amino acid sequence since PMT is blocked in the N-terminal and therefore is not degraded by procedures for the sequencing of amino acids.

Another routine screening method which has proven to be difficult in the case of PMT is screening for toxin-producing clones by means of an anti-PMT serum. When using serum from a rabbit repeatedly immunized with PMT, the present inventors found 5 E. coli clones by the Colony blot method in the gene library described in Example 5. Further studies of the above 5 clones, however, showed that none of them were producing PMT. These results indicate the importance of performing the screening with anti-PMT monoclonal antibodies as described in Example 5.

The nucleotide sequence may also be derived from a bacteriophage infectious for *P. multocida*, i.e. one which has been transferred from one bacterial strain which originally carried the sequence to another strain which did not originally carry the sequence by bacteriophage transfection. Similarly, the nucleotide sequence may be derived from a plasmid or other genetic element transferred from one strain to another by conjugation, transformation or the like.

Furthermore, the nucleotide sequence coding for the toxin may be a synthetic sequence, that is, one prepared according to standard procedures, e.g. as described in Matthes et al., 1984, (ref. 13). Finally, the nucleotide sequence may be a mixed genomic and synthetic or mixed cDNA and synthetic sequence prepared by ligating DNA fragments of genomic, cDNA or synthetic origin (as appropriate) which DNA fragments each contain part of the nucleotide sequence encoding the toxin, in accordance with established methods.

In accordance with the explanation given above, the DNA molecule or DNA fragment may be one which has been modified by substitution, addition, insertion or deletion of one or more nucleotides in the sequence with the purpose of establishing a sequence which, when expressed, results in the production of a detoxified toxin or toxin analogue.

In particular, the invention relates to a DNA fragment which comprises a nucleotide sequence substantially as shown in FIGS. 10 (*a*)–(*j*) (SEQ ID NO:1) or a modification thereof as indicated above. The sequence coding for the full-length toxin starts at position 219 (or 213) of the sequence shown in the figure, while the end of the sequence is at position 4073. The DNA sequence shown in FIGS. 10 (*a*)–(*j*) (SEQ ID NO:1) has been established by well-known methods as described in Example 7 below.

The DNA molecule or DNA fragment of the invention may further comprise a nucleotide sequence encoding another polypeptide fused to the nucleotide sequence encoding the toxin or toxin analogue with the purpose of producing a fused polypeptide, as explained above. A further purpose of preparing a fused polypeptide may be to facilitate purification of the toxin. In this case, the fused sequence may be inserted into an appropriate vector which is transformed to a suitable host microorganism which is grown under conditions ensuring expression of the fused sequence after which the fused polypeptide is recovered from the culture by subjecting the fused polypeptide to affinity chromatography involving an antibody or any other ligand reacting with the second polypeptide. After purification, the second polypeptide may then be removed, for instance by suitable proteolytic cleavage followed by separation of the two polypeptides.

In a further aspect, the invention relates to an expression vector which is capable of replicating in a host microorganism and which carries a DNA molecule or DNA fragment as described above. The vector may either be one which is capable of autonomous replication, such as a plasmid, or one which is replicated with the host chromosome, such as a bacteriophage. Specific examples of expression vectors of the invention are the plasmids pSPE A-R described in Example 9 below and shown in the appended FIG. 13.

In a still further aspect, the invention relates to a microorganism which is capable of expressing a DNA molecule or DNA fragment as defined above and which carries a vector as described above. The microorganism is preferably a bacterium, especially a gramnegative bacterium such as *E. coli*.

The invention also relates to a method of producing an immunogenic detoxified *P. multocida* toxin or toxin analogue, the method comprising a) isolating a nucleotide sequence coding for the *P. multocida* toxin or toxin analogue, b) inserting said sequence, optionally in suitably modified form resulting in the expression of the detoxified toxin or toxin analogue or a subsequence coding for an immunogenic subsequence of the toxin ot toxin analogue, in an expression vector, c) transforming a suitable host microorganism with the vector produced in step b), d) cultivating the microorganism produced in step c) under suitable conditions for expressing the toxin or toxin analogue, e) harvesting the toxin or toxin analogue from the culture, and f) optionally subjecting the toxin to posttranslational modifications to produce the detoxified toxin or toxin analogue.

In step a) of the method, the nucleotide sequence may for instance be isolated by establishing a *P. multocida* gene library and screening for toxin-positive clones in accordance with established methods as indicated above as well as described in detail in Example 4 below.

In step b) of the method, the modification of the sequence optionally carried out may be performed before or after the sequence has been inserted in the vector. The modification may comprise substitution, addition, insertion or deletion of one or more nucleotides in the sequence or a combination thereof, as explained above.

The transformation in step c) of the method may be carried out by standard procedures, such as disclosed in Maniatis et al. (ref. 14).

The cultivation of the host microorganism in step d) of the method may be carried out in a culture medium conventionally used for fermentation purposes, e.g. Luria Broth medium, and under conditions with respect to pH, temperature, aeration, etc. suited to the type of microorganism in question, e.g. as disclosed in Maniatis et al. (ref. 14).

In step e) of the method, the harvesting of the toxin or toxin analogue may proceed by well-known methods such as by precipitation, gel filtration, ion exchange or HPLC reverse phase chromatography or immunoaffinity chromatography.

If the nucleotide sequence coding for the toxin or toxin analogue has not been modified in step b) of the method to result in expression of the detoxified toxin or toxin analogue, the toxin or toxin analogue should be subjected to posttranslational modifications in step f) of the method, for instance thermal treatment, treatment with a chemical such as formaldehyde, glutaraldehyde or a suitable proteolytic enzyme, e.g. trypsin, or substitution, addition, insertion or deletion of one or more amino acids in the toxin or toxin analogue.

In a still further aspect, the invention concerns a method of producing a vaccine for immunizing an animal, including a human being, against diseases caused by microorganisms producing an osteolytic toxin, the method comprising formulating the toxin or toxin analogue produced by recombinant DNA techniques or by peptide synthesis as described above with an immunologically acceptable carrier or vehicle, such as those indicated above.

In a further, interesting aspect, the present invention relates to a non-pathogenic microorganism which carries and is capable of expressing an inserted nucleotide sequence coding for an immunogenic detoxified P. multocida toxin or toxin analogue for use as a live vaccine for the immunization of an animal against diseases caused by microorganisms producing an osteolytic toxin. The use of a live vaccine might be advantageous since there is some indication that vaccines based on living organisms show an excellent immunogenicity, often conferring a lifelong immunity against the disease in question. Live vaccines also tend to be less expensive to produce than those based on a purified protein, no purification step being required.

In order to provide expression of the toxin or toxin analogue in detoxified form, the nucleotide sequence coding for the toxin or toxin analogue may be suitably modified, either before or after introduction into the host microorganism, by substitution, addition, insertion or deletion of one or more nucleotides in the sequence or a combination of these measures, as explained above.

In a particularly advantageous embodiment of the live vaccine of the invention, the nucleotide sequence coding for the toxin or toxin analogue is expressed on the outer surface of the host cell. This provides a favorable presentation of the toxin epitope(s) which will be recognized by the immune defense mechanisms of the animal to which the live vaccine is administered, thus provoking an appropriate immune response. One way of providing the expression of the toxin or toxin analogue on the cell surface is to fuse the nucleotide sequence encoding the toxin or toxin analogue to another nucleotide sequence encoding a surface protein or a subsequence thereof (e.g. a signal peptide) which cause the toxin or toxin analogue to be expressed on the outer surface of the host cell, optionally as a fused polypeptide, Examples of useful surface proteins are adhesins, fimbrial proteins, e.g. the E. coli K88 or Type 1 fimbrial protein, or the LamB protein of E. coli.

The invention also relates to the use of a recombinant, detoxified immunogenic P. multocida toxin or toxin analogue for preparing a vaccine for the immunization of an animal, including a human being, against diseases caused by microorganisms producing an osteolytic toxin. The toxin or toxin analogue used for immunization may be one encoded by the DNA sequence shown in FIGS. 10 (a)–(j) (SEQ ID NO:1) or a modification thereof as explained above.

Similarly, the present invention relates to a method of immunizing an animal, including a human being, against diseases caused by microorganisms producing an osteolytic toxin, the method comprising administering to the animal an immunogenically effective amount of a recombinant detoxified immunogenic P. multocida toxin or toxin analogue, such as the one encoded by the DNA sequence shown in FIGS. 10 (a)–(j) (SEQ ID NO:1) or a modification thereof. The toxin or toxin analogue may be administered intravenously, intramuscularly, subcutaneously, intraperitoneally, orally or intranasally. It is contemplated that a suitable dosage range will be 0.1–500 µg, dependent on the age and condition of the animal in question, the route and form of administration and the immunogenicity of the toxin or toxin analogue.

In a preferred embodiment, the monoclonal antibody of the present invention is one raised against the P. multocida toxin produced by P. multocida ssp. multocida 45/78, which is publicly available from the National Collection of Type Cultures (NCTC), Central Public Health Laboratory, London, England, with the accession number NCTC 12178.

In connection with the research leading to the present invention, several different monoclonal antibodies to the toxin produced by this Pasteurella strain have been prepared (vide Example 1 below), representative examples of which are the ones produced by the hybridoma cell lines P3F37 and P3F51. Samples of these cell lines were deposited in accordance with the provisions of the Budapest Treaty on the International Recognition of the Deposit of Microorganisms for the Purpose of Patent Procedure, on Dec. 3, 1987, in the European Collection of Animal Cell Cultures (ECACC), Centre for Applied Microbiology and Research, Porton Down, Salisbury, Wiltshire, Great Britain, with the accession numbers ECACC 87120301 and ECACC 87120302, respectively.

The monoclonal antibody of the invention may be prepared by a method comprising:

a) Immunizing a suitable animal or animal cell with an immunogenic P. multocida toxin or toxin analogue to obtain cells producing an antibody to said toxin or toxin analogue, b) fusing cells producing the antibody with cells of a suitable myeloma cell line, and selecting and cloning the resulting hybridoma cells producing said antibody, or c) immortalizing an unfused cell line producing said antibody, e.g. by viral transformation, followed by d) growing the cells of step b) or c) in a suitable medium to produce said antibody and harvesting the antibody from the growth medium.

The initial immunization of the animals in step a) of the method requires a modification of the conventional method of producing monoclonal antibodies disclosed by Köhler and Milstein, Nature 256, 1975, p. 495, since, PMT, even when it is administered to mice in sublethal doses, will cause an atrophy of the spleen which seriously complicates the hybridoma technique. The animals must therefore initially be immunized with a detoxified toxin preparation as it has been found that any subsequent booster immunizations may be carried out with the native toxin which need not be detoxified before use. The immunization may otherwise be carried out according to conventional procedures, e.g. by administering a solution or suspension of the (detoxified) toxin or toxin analogue in a suitable solvent such as isotonic saline or phosphate buffered saline optionally containing an adjuvant such as one of those indicated above. Animals suited for immunization purposes are, for instance, mice, rabbits, goats, sheep, guinea pigs, etc. The bleeding of the animals and recovery of the polyclonal antibodies may be performed by conventional procedures.

The antibody-producing cells used for fusion to the myeloma cells are preferably spleen or lymph cells (e.g. lymphoblasts, B-lymphocytes, plasma cells or related cells isolated from spleen, lymph nodes or functionally related tissues). The fusion of antibody-producing cells and myeloma cells may be performed substantially as described by Köhler and Milstein, supra, that is, preferably in the presence of a fusion promoter such as polyethylene glycol. A ratio of about 3 antibody-producing cells per myeloma cell is preferred. The myeloma cell line employed is preferably of a type unable to survive in selective medium and unable to produce immunoglobulins by itself; one type of cell line frequently used for cell fusions is one which lacks the enzyme hypoxanthine-guanine phosphoribosyltransferase and which is consequently unable to grow in a medium containing hypoxanthine, aminopterin and thymidine (HAT medium).

The selection of hybridoma cells which produce an antitoxin-antibody may then be carried out by culturing unfused antibody-producing cells, unfused myeloma cells and supposedly fused cells in a selective medium (such as HAT) in which the unfused myeloma cells cannot grow and eventually die out. The unfused antibody-producing cells can only survive for a limited period of time after which they also die out. On the other hand, successfully fused cells continue to grow as they have inherited permanent growth properties from the parent myeloma cells and the ability to survive in the selective medium from the parent antibody-producing cells.

Alternatively to the production of hybridomas, immortalized unfused antibody-producing cells may be produced either by transferring the genes responsible for production of immunoglobulin from the hybridoma to another (more viable) cell line or by viral transformation as described by Klein et al., (ref. 16).

The resulting antibody-producing cells (whether hybridomas or unfused cells) may be grown in vitro after cloning, e.g. as described in Example 1 below, in a suitable medium, such as RPMI 1640. This results in the production of monoclonal antibodies of a very high purity as these are secreted into the culture supernatant by the cells. The antibodies may then be isolated by conventional methods such as centrifugation, filtration, precipitation, chromatography, or a combination thereof.

In an alternative method, the monoclonal antibodies may also be produced in the body cavity of an animal such as a mouse. In this embodiment, the antibody-producing cell is injected into an animal such as a mouse resulting in the formation of an ascites tumour which releases high concentrations of the antibody in the ascites of the animal. Although the animals will also produce normal antibodies, these will only amount to a minor percentage of the monoclonal antibodies which may be purified from ascites by standard purification procedures such as centrifugation, filtration, precipitation, chromatography or a combination thereof.

In a further aspect, the invention relates to a diagnostic agent which comprises a monoclonal antibody as defined above.

Although in some cases such as when the diagnostic agent is to be employed in an agglutination assay in which solid particles to which the antibody is coupled agglutinate in the presence of a *P. multocida* toxin in the sample subjected to testing, no labelling of the monoclonal antibody is necessary, it is preferred for most purposes to provide the antibody with a label in order to detect bound antibody. In a double antibody ("sandwich") assay, at least one of the antibodies may be provided with a label. Substances useful as labels in the present context may be selected from enzymes, fluorescers, radioactive isotopes and complexing agents such as biotin.

Examples of enzymes which may be used as label substances are peroxidases, e.g. horseradish peroxidase, or phosphatases. e.g. alkaline phosphatases. As enzymes are not directly detectable, they must be combined with a substrate to form a detectable reaction product which may, for instance, be fluorescent or coloured. Examples of useful substrates are $H_2O_2$/o-phenylene diamine, $H_2O_2$/azinodiethylbenzthiazoline sulphonic acid and p-nitrophenylphosphate.

Examples of fluorescers useful as label substances are $H_2O_2$/p-hydroxyphenylacetic acid and methylumbelliferyl phosphate. Such substances may be detected by means of a fluorescence spectrophotometer in a manner known per se.

Examples of radioactive isotopes useful as label substances are I-125, S-35 and P-32. The radioactivity emitted by these isotopes may be measured in a gamma-counter or a scintillation counter in a manner known per se.

In a favoured embodiment, the diagnostic agent comprises at least one antibody covalently or non-covalently coupled to a solid support. This may be used in a double antibody assay in which case the antibody coupled to the solid support is not labelled. The solid support may be composed of a polymer or may comprise a matrix on which the polymer is applied. The solid support may be selected from a plastic, e.g. latex, polystyrene, polyvinylchloride, nylon, polyvinylidene difluoride, cellulose, e.g. nitrocellulose and magnetic carrier particles (e.g. iron particles coated with polystyrene).

For use in a diagnostic assay, the solid support may have any convenient shape. Thus, it may be in the form of a plate, e.g. a thin layer or, preferably, microtiter plate, a strip, film, paper or solid particles such as latex beads or the like.

Rather than being coupled directly to the solid support, the monoclonal antibody may be coupled to a ligand immobilized on a solid support. Examples of ligands include Protein A, or an immunoglobulin-specific antibody.

It should be noted that practically all methods or applications based on intact monoclonal or polyclonal antibodies could instead be performed using fragments of the monoclonal or polyclonal antibody, e.g. $F(ab')_2$ or Fab fragments (cf. Coding, 1978, (ref. 17).

For use in a sandwich assay, the diagnostic agent may additionally comprise a polyclonal antibody. This antibody may be labelled and/or coupled to a solid support as described above in connection with the. monoclonal antibody.

The monoclonal antibody of the invention may be used in a method of determining the presence of a *P. multocida* toxin or toxin analogue in a sample, the method comprising incubating the sample with a monoclonal antibody as described above and detecting the presence of bound toxin or toxin analogue resulting from said incubation. The antibody may be provided with a label as explained above and/or may be bound to a solid support as exemplified above.

In a favoured embodiment of the method, the sample is incubated with a first monoclonal antibody coupled to a solid support and subsequently with a second monoclonal or polyclonal antibody provided with a label. An example of this embodiment is the sandwich ELISA (enzyme linked immunosorbent assay) assay described in Example 2 below.

In an alternative embodiment (a so-called competitive binding assay), the sample may be incubated with a monoclonal antibody coupled to a solid support and simultaneously or subsequently with a labelled *P. multocida* toxin or toxin analogue the latter competing for binding sites on the antibody with any toxin or toxin analogue present in the sample.

The sample subjected to the present method may be any sample suspected of containing a *P. multocida* toxin or toxin analogue. Thus, the sample may be selected from bacterial suspensions, bacterial extracts, culture supernatants, animal body fluids (e.g. serum, colostrum or nasal mucous) and intermediate or final vaccine products.

Apart from the diagnostic use of the monoclonal antibody of the invention, it is contemplated to utilize the well-known ability of certain monoclonal antibodies to inhibit or block the activity of biologically active antigens by incorporating the monoclonal antibody in a composition for the passive immunization of an animal, including a human being, against diseases caused by microorganisms producing an osteolytic toxin, which comprises a monoclonal antibody as described above and a suitable carrier or vehicle. The composition may be prepared by combining an effective immunizing amount of the antibody or fragment thereof with a suitable carrier or vehicle. Examples of suitable carriers and vehicles may be the ones discussed above in connection with the vaccine of the invention. The composition may further comprise an adjuvant such as one of those indicated above.

Based on experiments with mice (cf. Example 11 below) where the monoclonal antibody induced passive immunity against PMT, it is contemplated that a PMT-specific antibody may be used for prophylactic or therapeutic treatment of atrophic rhinitis in pigs. It may be administered intravenously, subcutaneously or intramuscularly as well as orally in suitably protected form or by means of an intranasal aerosol.

A further use of the monoclonal antibody of the invention is in a method of isolating a *P. multocida* toxin or toxin analogue, the method comprising adsorbing a biological material containing said toxin or toxin analogue to a matrix comprising an immobilized monoclonal antibody as described above, eluting said toxin or toxin analogue from said matrix and recovering said toxin or toxin analogue from the eluate.

The matrix may be composed of any suitable material usually employed for affinity chromatographic purposes such as agarose, dextran, controlled pore glass, DEAE cellulose, optionally activated by means of CNBr, divinylsulphone, etc. in a manner known per se.

The present invention further relates to a diagnostic agent for the detection of PMT-producing microorganisms, which comprises a labelled DNA sequence homologous with a DNA sequence coding for a *Pasterurella multocida* toxin or toxin analogue. In this context, the term "homologous with" is intended to indicate that the DNA sequence comprises at least one stretch of deoxyribonucleotides of at least 15 bases with 80% homology to a part of the shown sequence or to a part of the sequence encoding a toxin analogue.

In a method employing the diagnostic agent, probe DNA is labelled, and the DNA is denatured to separate the strands in both probe and sample DNA; the DNAs are mixed and the strands are left to reform the double helical structure, but in case of homology, some of the probe DNA will have combined with the sample DNA. This is known as hybridization and is described by for instance Southern, 1980, (ref. 18). The DNA used as the probe should have a unique nucleotide sequence of a certain length in order to be sufficiently specific as a diagnostic agent. The probe DNA may advantageously be labelled with a radioactive isotope such as H-3, I-125, S-35 or P-32 as described e.g. by Rigby et al., 1977, (ref. 19); a complexing agent such as biotin (Gebeyechu et al., 1987, (ref. 20); or with digoxygenin-dUTP according to the method described by the manufacturer of the reagent, Boehringer, Mannheim.

In a particular embodiment of the invention, detection of the presence of *Pasteurella multocida* toxin producing microorganisms in a sample is performed by use of a DNA probe in the polymerase chain reaction procedure described by Saiki et al., 1985, (ref. 21). The polymerase chain reaction (PCR) is a procedure used for the amplification of DNA present in a sample. The procedure involves the use of two oligonucleotide primers which flank the DNA segment to be amplified. The oligonucleotide primers may e.g. comprise the regions of the gene coding for *Pasteurella multocida* toxin or toxin analogue and may thus be used to amplify the said gene or part of it present in a sample. The oligonucleotide primers hybridize to opposite strands of the DNA sequence to be amplified, and the primers are extended by using DNA polymerase, e.g. the Klenow fragment of *E.coli* DNA polymerase I or another useful DNA polymerase such as the Taq DNA polymerase, so as to synthesize a DNA sequence which is complementary to the DNA sequence to which the primers are annealed. Subsequent to the synthesis of these complementary sequences, the DNA synthesized is denatured, e.g. by heating, from the "parent DNA strings", and the parent strings as well as the newly synthesized DNA strings are subjected to a new PCR amplification cycle. In this manner, it is possible to obtain a substantial amplification of specific DNA sequences which are present in a sample. By use of the PCR amplification method, it may be possible to amplify and then detect originally very small and undetectable amounts of DNA sequences present in a sample.

In a still further aspect, the present invention relates to a method of determining the presence of antibodies against a *P. multocida* toxin or toxin analogue in a sample, the method comprising incubating the sample with a *P. multocida* toxin or toxin analogue and detecting the presence of bound antibody resulting from said incubation.

A diagnostic agent comprising the toxin or toxin analogue used in this method may otherwise exhibit any of the features described above for diagnostic agents comprising the monoclonal antibody and be used in similar detection methods although these will detect bound antibody rather than bound toxin as such. The diagnostic agent may be useful, for instance as a reference standard or to detect anti-toxin antibodies in body fluids, e.g. serum, colostrum or nasal mucous, from animals exposed to the toxin or toxin analogue.

A still further use of a *P.multocida* toxin or toxin analogue is for the preparation of a toxin reference standard which may be useful as a standard of comparison in qualitative or quantitative analytical procedures. In a qualitative procedure, the standard toxin in a known concentration may be reacted with a monoclonal or a polyclonal antibody raised against the toxin or toxin analogue, a positive reaction indicating the specificity of the antibodies. In another aspect, the reference standard preparation is applied in a quantitative analytical procedure by which different concentrations of the preparation is reacted with a monoclonal or a polyclonal antibody in order to provide a calibration curve which may allow the precise amount of toxin or toxin analogue in a sample to be estimated.

BRIEF DESCRIPTION OF THE DRAWINGS

The invention is further disclosed in the following with reference to the drawings in which.

The hatched area denotes *P. multocida* DNA, the shaded area denotes the pmt gene and the vertically hatched area denotes plasmid pUN121 DNA.

Figure 5:
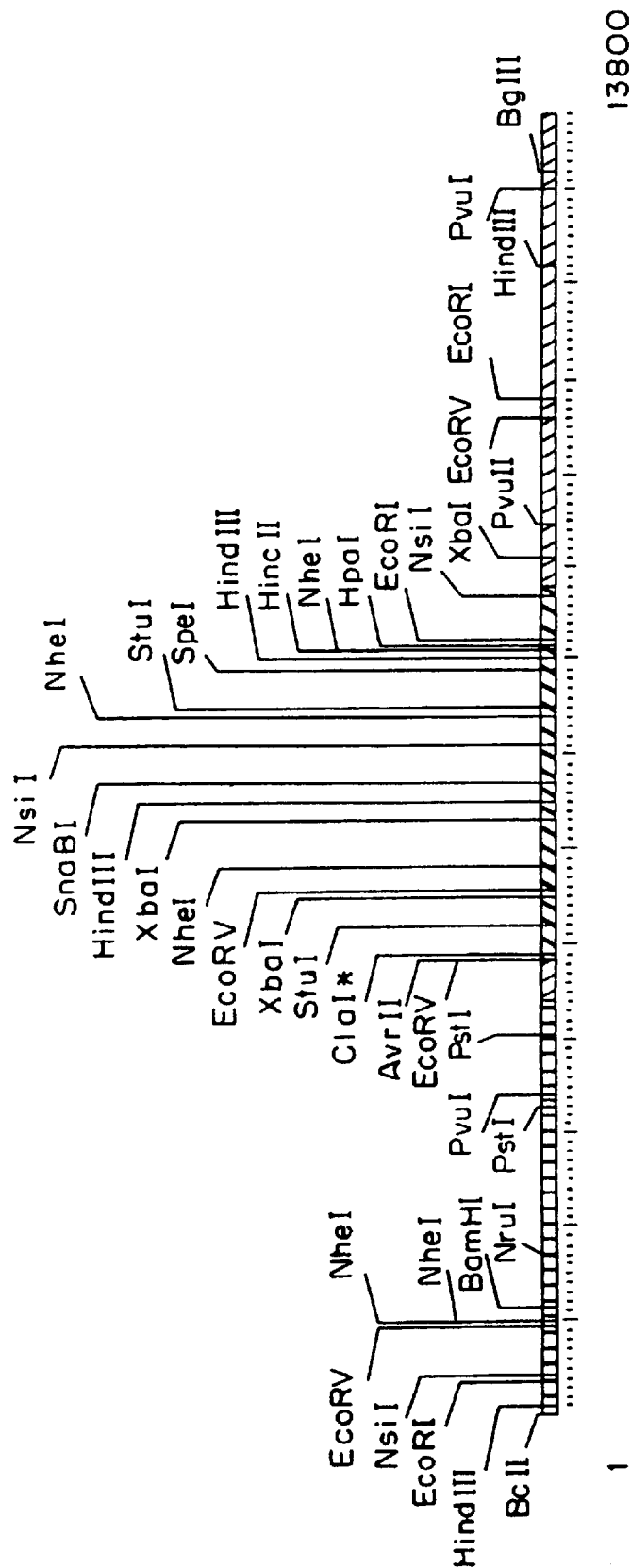

FIG. 5 is a restriction enzyme cleavage map of the plasmid pSPE 312 with a length of 13.8 kb. The hatched area denotes *P. multocida* DNA, the shaded area denotes the pmt gene and the vertically hatched area denotes plasmid pUN121 DNA.

Figure 6:
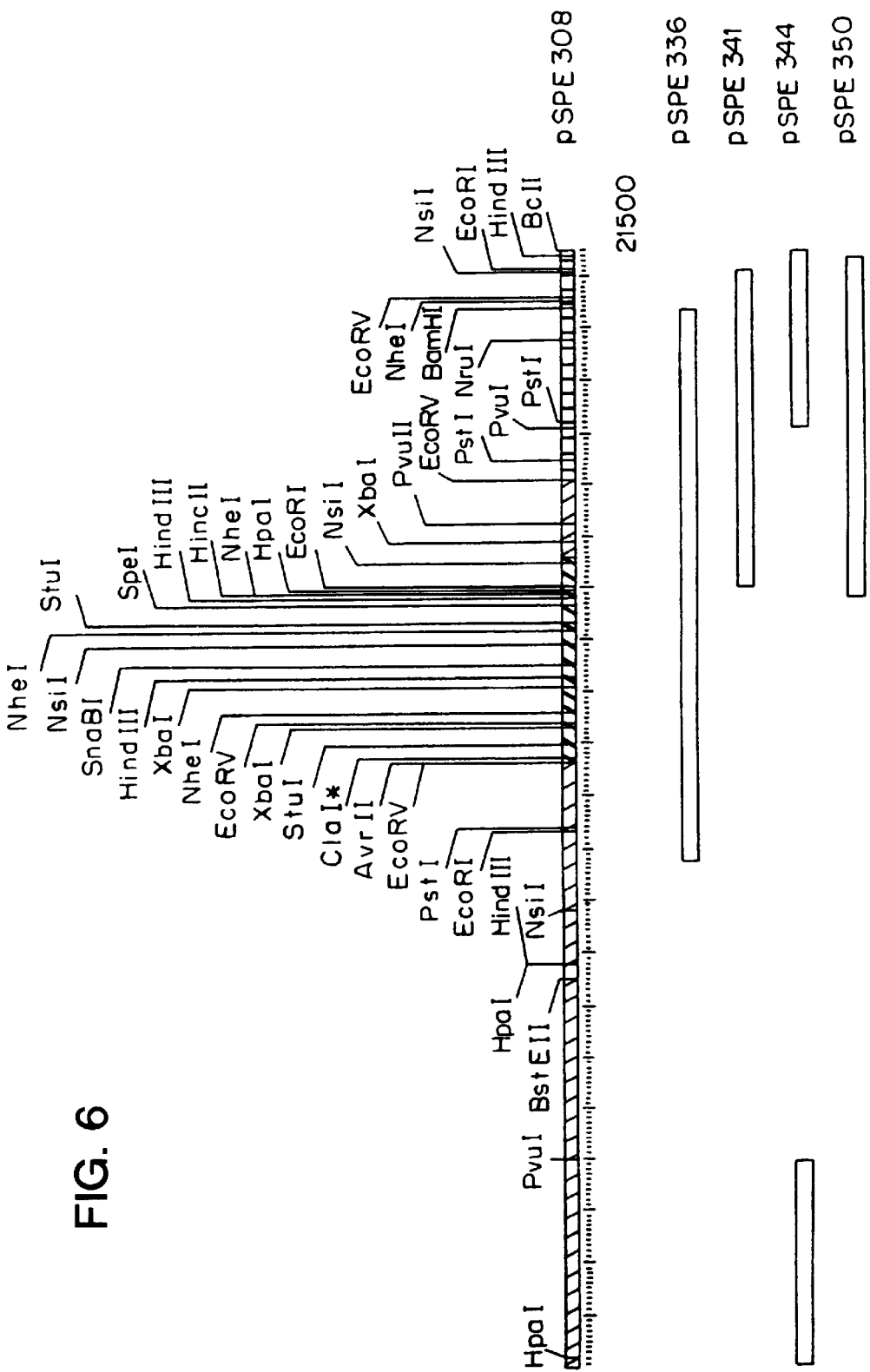

FIG. 6 is a restriction enzyme cleavage map of plasmids constructed by enzymatic cleavage of the plasmid pSPE 308. The hatched area denotes *P. multocida* DNA, the shaded area denotes the pmt gene, and the vertically hatched area denotes pUN121 DNA.

Figure 7:
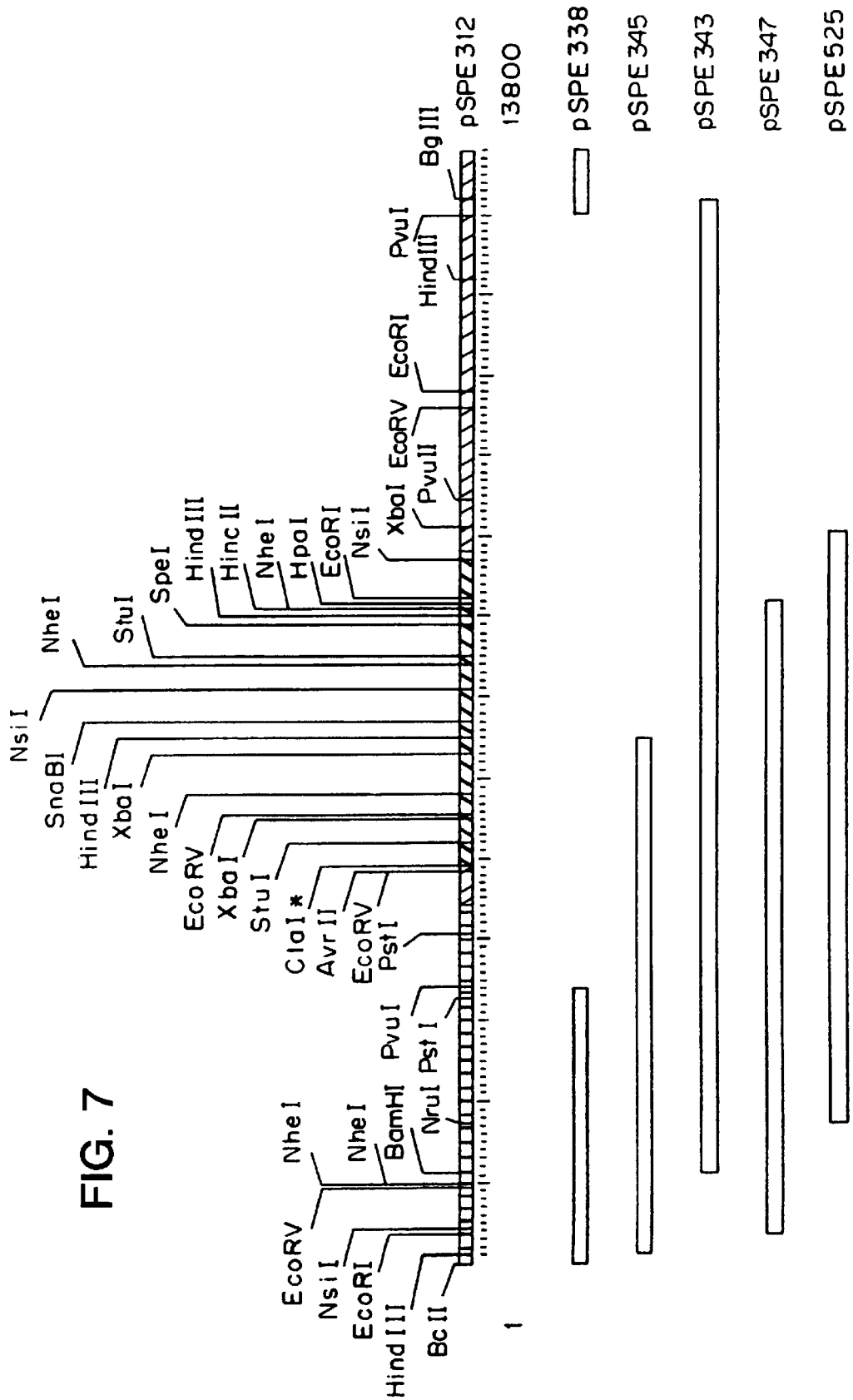

FIG. 7 is a restriction enzyme cleavage map of plasmids constructed by enzymatic cleavage of pSPE 312. The hatched area denotes *P. multocida* DNA, the vertically hatched area denotes pUN121 DNA, and the shaded area denotes the pmt gene.

Figure 8:
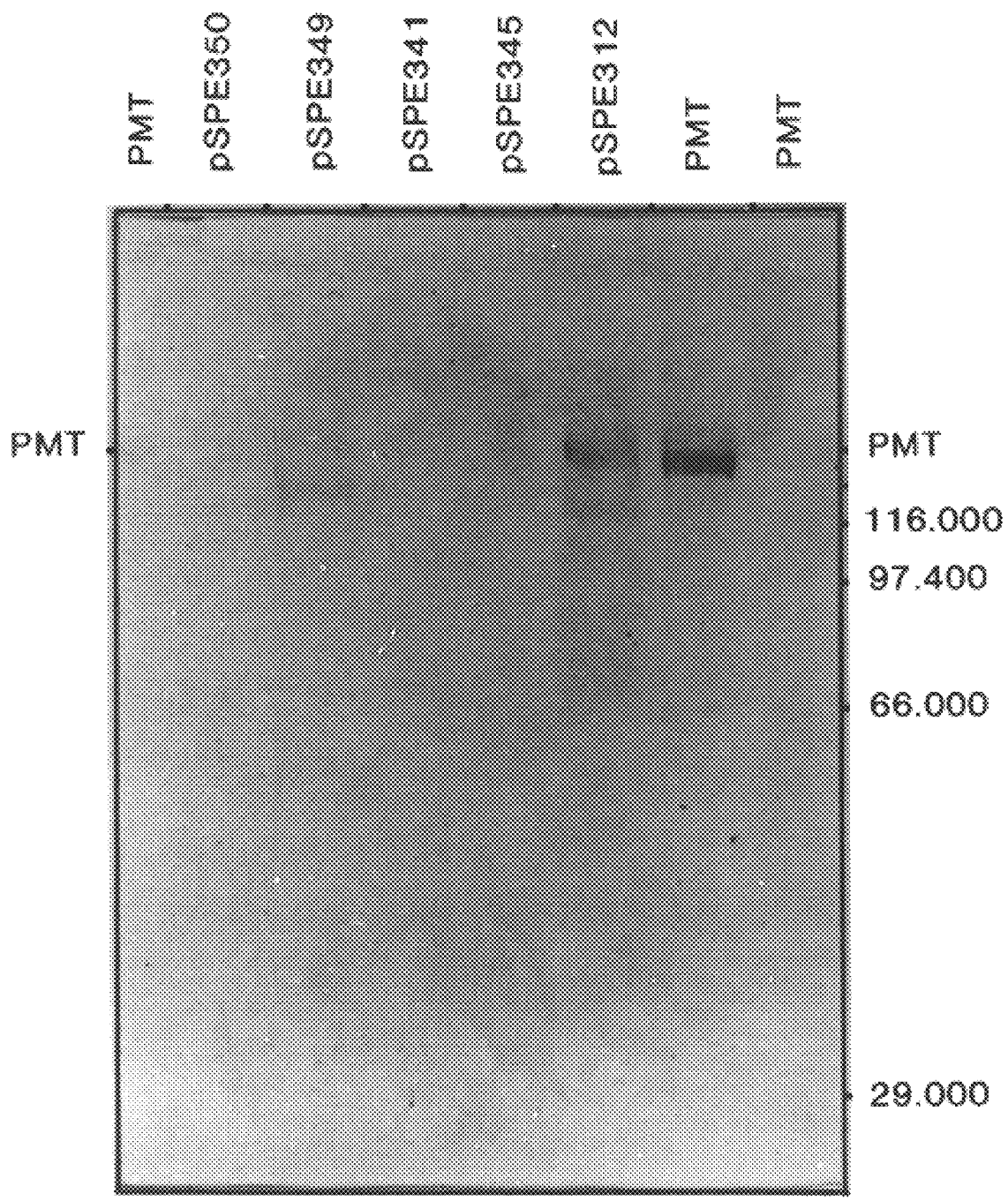

FIG. 8 is a Western blot showing PMT production by derivatives of plasmids pSPE 308 and pSPE 312. Lane 1: purified PMT; lane 2: pSPE 350; lane 3: pSPE 349; lane 4: pSPE 341; lane 5: pSPE 345; lane 6: pSPE 312; lanes 7 and 8: purified PMT. Plasmid pSPE 349 is identical to plasmid pSPE 347 shown in FIG. 7.

Figure 9:
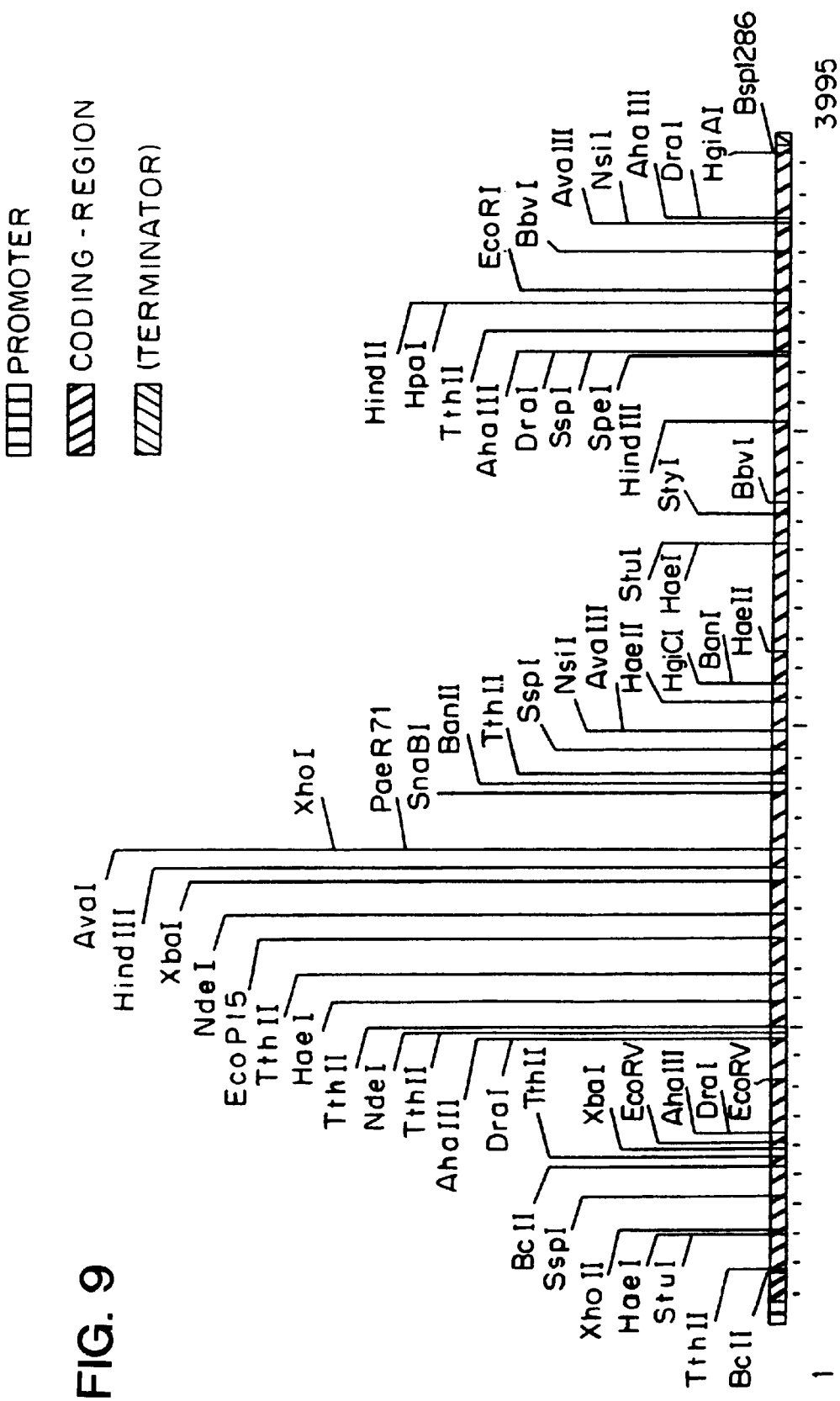

FIG. 9 is a restriction enzyme cleavage map of the pmt gene. The shaded area denotes the pmt gene, the vertically hatched area denotes a probable promoter, and the hatched area denotes a probable terminator.

FIGS. 10 (a)–(j) shows the DNA sequence (SEQ ID NO:1) of the pmt gene region and the amino acid sequence (SEQ ID NO:2) deduced on the basis of the DNA sequence. The amino acids are identified with single-letter codes according to conventional usage. The amino acid sequence has been shown to start at position 213 or 219.

Figure 11:
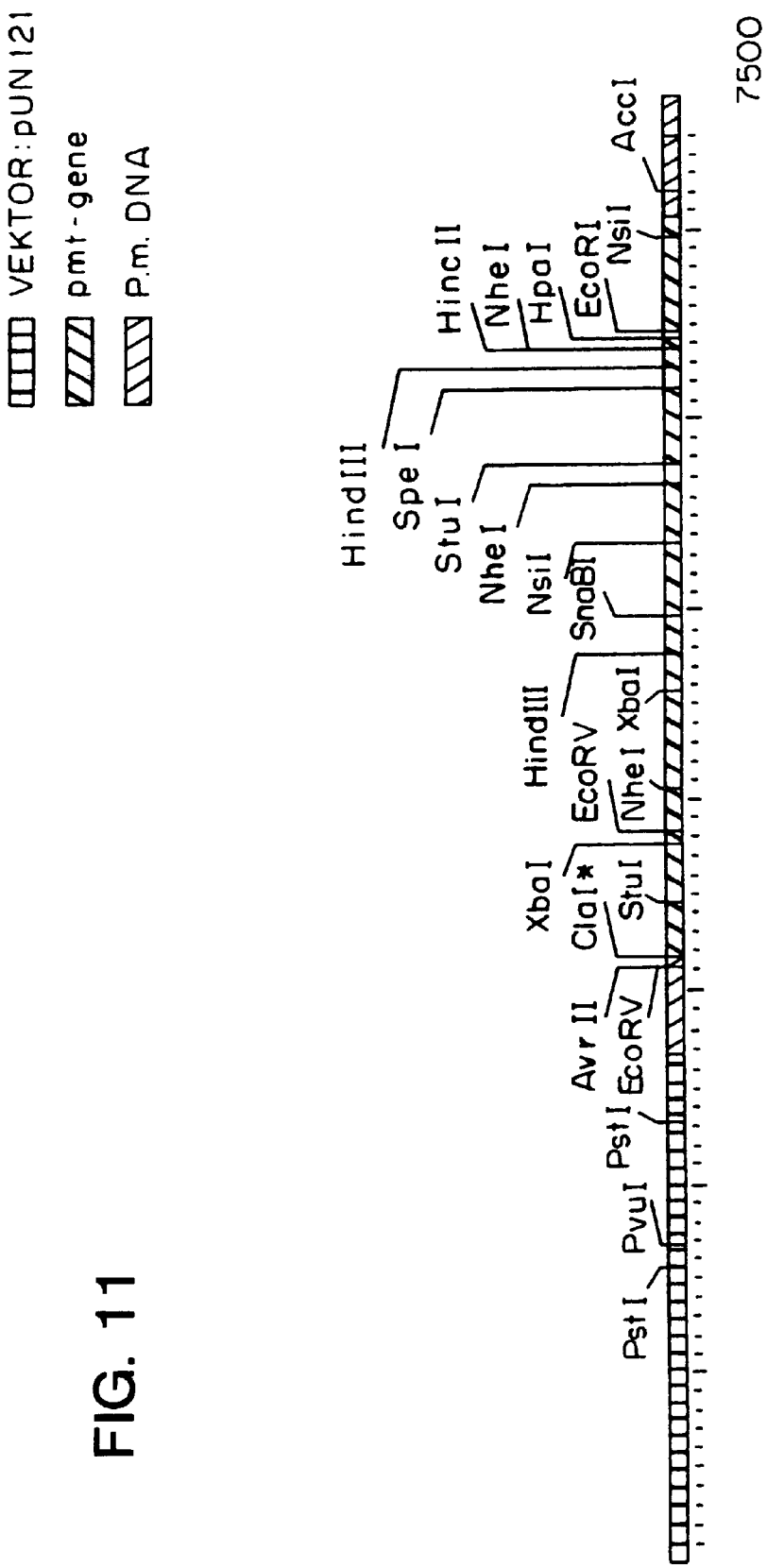

FIG. 11 is a restriction enzyme cleavage map of the plasmid pSPE 525 with a length of 7.7 kb. The hatched area denotes *P. multocida* DNA, the shaded area denotes the pmt gene, and the vertically hatched area denotes pUN121 DNA.

Figure 12:
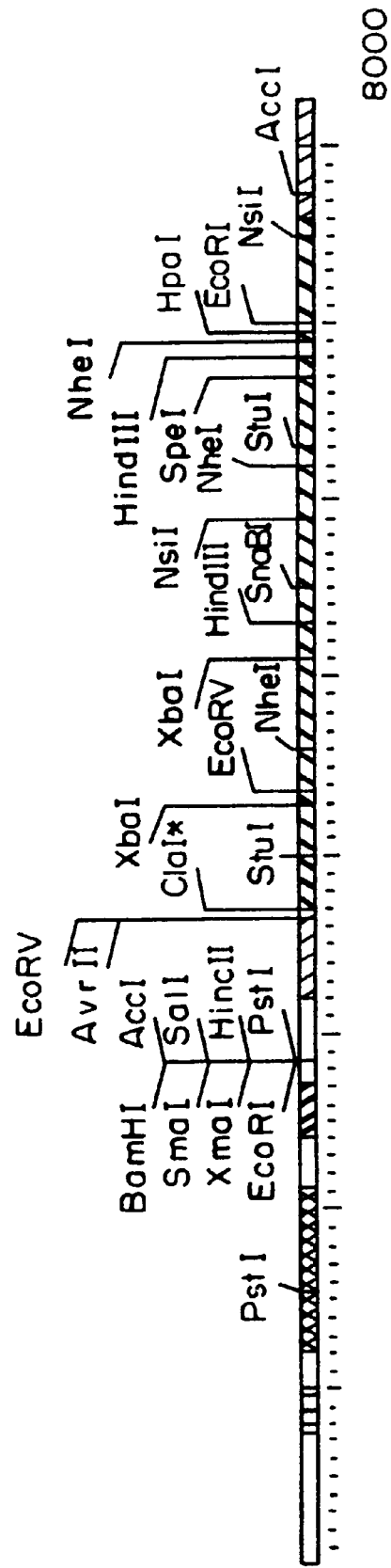

FIG. 12 is a restriction enzyme cleavage map of the expression vector pSPE 481 with a length of 8.25 kb. The hatched (towards the right) area denotes *P. multocida* DNA, the shaded area denotes the pmt gene, the hatched (towards the left) area denotes $\lambda P_L$ DNA, the cross-hatched area denotes the amp gene, and the vertically hatched area denotes the origin of replication.

Figure 13:
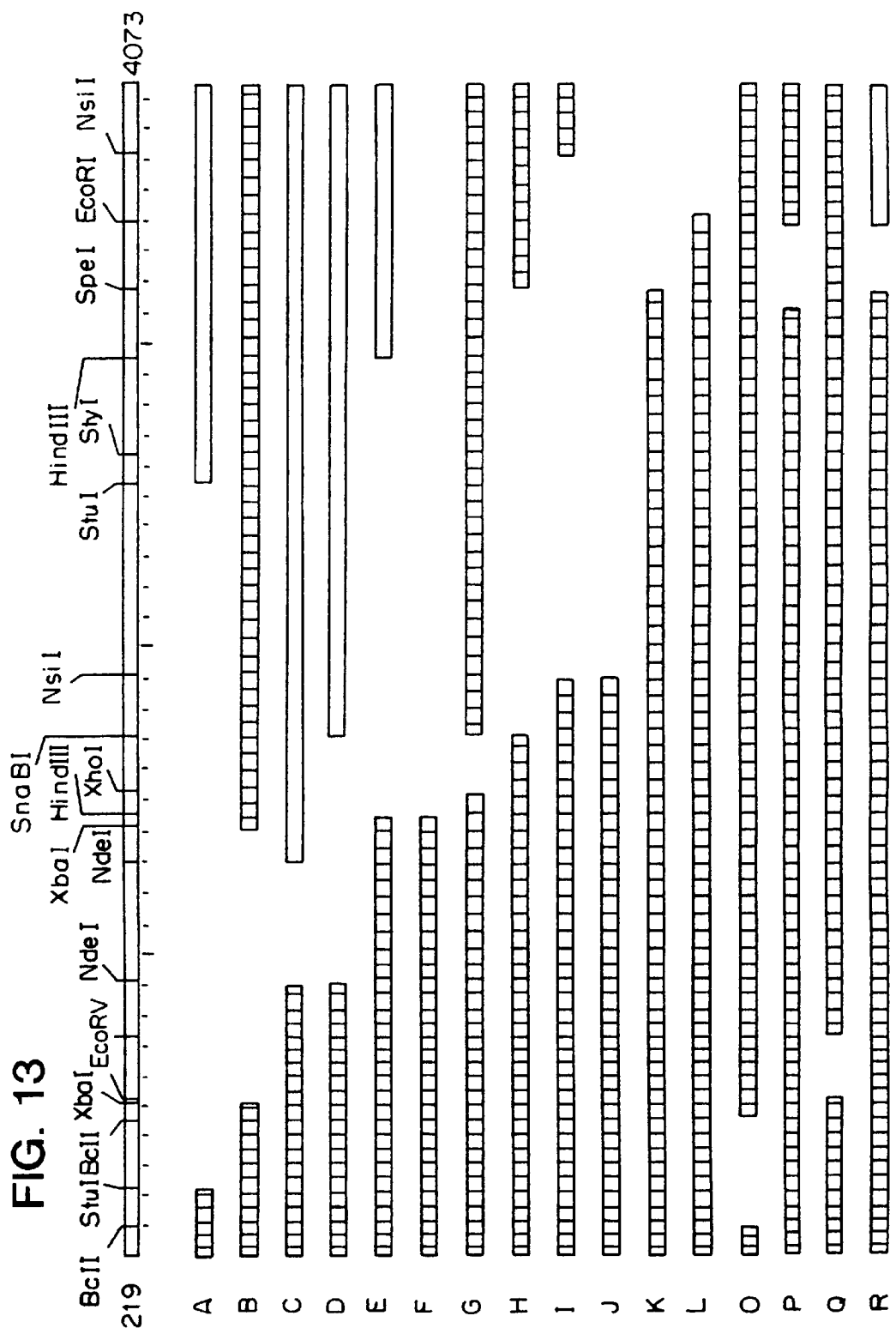

FIG. 13 is a restriction enzyme cleavage map of the toxA coding region. Extension of coding region present on each derivative plasmid (pSPE A-R) is indicated (A-R) by bars. Hatched bars: Coding region in correct reading frame; open bars: Coding region not in frame with the 5' part of the coding region.

Figure 14:
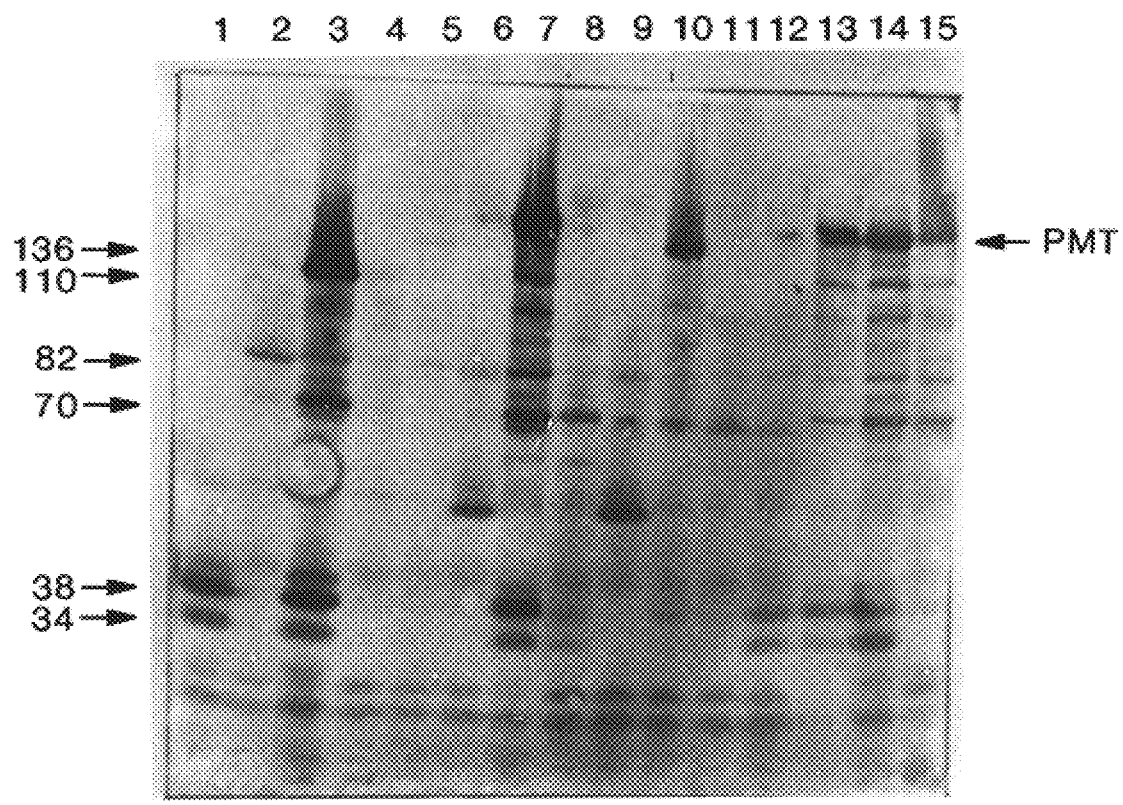

FIG. 14 is a Western blot showing the recognition by a mouse anti-PMT antiserum of PMT derivatives produced by the plasmids pSPE A-L. Lanes 7, 13, 14 and 15: different strains harbouring the entire pmt gene; lane 1: derivative A; lane 2: derivative I; lane 3: derivative B; lane 4: derivative J; lane 5: derivative L; lanes 6 and 9: derivative E; lane 8: derivative C; lane 10: derivative G; lane 11: derivative H; lane 12: derivative D. Approximate sizes (in kilodalton) of prominent full-length derivatives and degradation products are indicated.

FIG. 15 is a graph showing the distribution of relative absorbances ($A/A_o$) by PMT-ELISA of extracts of non-cytopathic (hatched bars) and cytopathic (black bars) field isolates of *P. multocida* diluted 1:1 in PBS-T-BSA.

FIG. 16 is a graph showing the mean±SD of relative absorbances ($A/A_o$) of dilutions of extracts of cytopathic (black squares) and non-cytopathic (open squares) field isolates of *P. multocida.*

FIG. 17 is a graph showing the presence of anti-PMT-antibodies in serum samples from anti-PMT-antibody-negative, infected and vaccinated pigs detected by competive ELISA. The graph shows the 50% blocking titers at an absorbance of 492 nm.

. . . negative

- - - infected

___ vaccinated

FIG. 18 shows the colony hybridization of *P. multocida* isolates, testing 17 toxin-positive and 18-toxin-negative strains as determined by the ELISA and EBL cell tests for the presence of the pmt gene.

FIG. 19 shows the determination of toxic activities of cell-free sonicates of recombinant *E.coli* clones. *E.coli* strain MT102 with PUN121 had no cytopathic effect on EBL-cells when diluted 1/25 in PBS (a). Sonicates of *E.coli* SPE312 (b) and toxigenic *P.multocida* (NCTC 12178) (c) diluted 1/3125 showed significant and identical effects (80× magnification).

FIG. 20 shows the *P.multocida* DNA flanking the pmt-gene (black area). The extension of the inserts of the plasmids pSPE308, pSPE312, pSPE344, pLOA03 and pLOB03 are indicated. The DNA contained in the probes used for the blotting (slant hatched area), and the fragments which contain the two homologous sequences (vertically hatched area) are shown.

FIG. 21 shows a Southern blot of restriction enzyme digested *P.multocida* DNA. Probe: 2,4 kb BglII-EcoRI fragment of pLOB03. Lanes 10*–14* is a short time exposure of lanes 10–14.

Lanes 1–4: Toxigenic *P.multocida* 45/78. Lanes 5–9: Nontoxigenic *P.multocida* MH81P8. Lane 10: pSPE308. Lane 11: pLOA03. Lane 12: pLOA02. Lane 13: pSPE312. Lane 14: pLOB03.

Restriction enzymes used: HindIII: Lanes 1, 5, 10, 11, 12 and 13.

EcoRI: Lanes 2, 6 and 14. BglII: Lanes 3 and 7. PvuII: Lanes 4 and 8.

PstI: Lane 9.

FIG. 22 shows a dot blot of 24 different *P.multocida* bacteriophage genomes. Probe: pLOA03. The probe does not hybridize to B2 and C5. A7: pSPE308; B7: pSPE312, C7: pLOA03 and D7: pLOB03 are positive controls.

EXAMPLE 1

Preparation of monoclonal antibodies against *P. multocida* toxin

Immunization

*P. multocida* toxin (PMT) was purified as described by Foged et al. (ref. 6), i.e., by 50% $(NH_4)_2SO_4$-precipitation of a cell-free extract of the toxigenic type D strain of *P. multocida* ssp. *multocida* 45/78 (refs. 3, 22) followed by DEAE-Sephacel® chromatography and preparative polyacrylamide gel electrophoresis (PAGE) in a manner known per se.

A suspension of the $(NH_4)_2SO_4$-precipitate prepared as described above and containing approx. 25 $\mu$g/ml of PMT was detoxified by incubation with 0.37% formaldehyde at 37° C. for 1 h. Female BALB/c mice (8–12 weeks old) were immunized subcutaneously on day 0 and 14 with 300 $\mu$l of a 1:1 dilution of the crude preparation of detoxified *P. multocida* toxin and Freund's incomplete adjuvant (day 0) or PBS (day 14). On day 30 and 45 1 $\mu$g of native PMT in 200 $\mu$l PBS was injected subcutaneously and on day 60 the mice were boosted intravenously with 0.5 $\mu$g of PMT in 100 $\mu$l PBS. Three days after the booster injection the mice were sacrified and their spleens removed for fusion.

Production of hybridoma cell lines and monoclonal antibodies

According to procedures described by Fazetas et al. (ref. 23) and Gebeychu et al. (ref. 20), the spleen cells and P3-X63-Ag8.653 myeloma cells were fused using 50% PEG 4000 GK (Merck) and the resulting hybridoma cells were grown selectively in hypoxanthine/aminopterin/thymine (HAT)—supplemented RPMI 1640 medium containing 15% fetal calf serum (FCS) and 4% human endothelial cell supernatant (Costar, The Netherlands).

Hybridoma cell lines were selected by analyzing their respective monoclonal antibodies by ELISA and immunoblotting.

ELISA for detection and titration of monoclonal antibodies

Microtiter plates (96-well Immuno Plate II, Nunc, Denmark) were coated with 50 μl/well of a 0.75 μg/ml solution of purified PMT in PBS at 4° C. for 16 h. and at 20° C. for 1 h. The wells were emptied and blocked with 200 μl PBS-T-BSA (PBS containing 0.05% (v/v) Tween®20 and 1% (w/v) bovine serum albumin) per well at 20° C. for 1 h., then washed 3 times with PBS-T. Fifty μl/well of hybridoma culture supernatant was applied at 20° C. for 1 h., and the plates were washed as described above. The anti-PMT antibody activity was measured calorimetrically after incubating at 20° C. for 1 h. with 50 μl/well of sheep anti-mouse immunoglobulin conjugated with horseradish peroxidase (Amersham International, U.K.) diluted 1:1,500 in PBS-T-BSA and (after 3 further PBS-T washes as above) with 50 μl of an o-phenylene diamine (OPD)$H_2O_2$ substrate solution. The reaction was stopped with 150 μl of 2 M $H_2SO_4$ after 5 min. and absorbance was determined in a Kontron SLT-210 photometer (SLT Lab-instr., Zurich, Switzerland) at 492 nm (ref. 620 nm).

The mean absorbance at the saturation level of the titration curve ($A_{sat}$) and the mean concentration of the MAb that resulted in 50% of the $A_{sat}$ ($C_{50}\%$) was determined by ELISA as described above, except that serial dilutions of the protein-A purified MAb in PBS-T-BSA was used. All results were based on at least duplicate determinations.

Immunoblotting

To determine the specificity of the monoclonal antibodies, the proteins contained in a crude cell-free extract of *P. multocida* 45/78, were separated by SDS-PAGE before transfer to a nitrocellulose membrane and immunological detection. Polyacrylamide gels (total acrylamide: 10%, relative bis-acrylamide: 3%) and an electrophoresis buffer were prepared according to Laemmli (ref. 24). Electrophoresis was performed vertically at 10° C. at a constant voltage of 60 V for 16 h. or 250 V for 4 h. Protein-bands on gels were either visualized by silver staining with a detection limit of less than 1 ng of protein per band (8) or transferred to a nitrocellulose membrane (0.45 μm) using a semidry electroblotter (Ancos, Ølstykke, Denmark (9)). The proteins on the nitrocellulose membrane were either detected by a colloidal gold silver enhancement staining method (detection limit: approx. 0.5 ng of protein per band) (ref. 25) or immunologically by a modification of the method previously described by Bjerrum et al. (ref. 26). A positive reaction in immunoblotting was recorded as + or (+), when an intense (or weak) staining of the PMT-band but no other protein band was observed. Staining of other bands or no reaction was recorded as –.

The molecular weight of PMT was estimated by comparison with known markers: ovalbumin (43.0 kd), BSA (66.3 kd), phosphorylase B (97.4 kd), β-galactosidase (116.2 kd), RNA-polymerase β (150.6 kd) and β' (155.2 kd) and myosin (approx. 200 kd).

ELISA for estimating epitope specificity

Estimation of apparent epitope specificity of anti-PMT MAbs was done by a competitive ELISA similar to a method described by Anderson et al. (ref. 27). Microtiter plates were coated with PMT and blocked as described above. Fifty μl of the competing MAb diluted to 10 μg/ml in PBS-T-BSA was added and incubated for 1 h. at 20° C. Without aspiration of the wells 25 μl biotinylated monoclonal antibody was added and the mixture was incubated for 20 min. at 20° C. After washings 50 μl of a 1:2,500 dilution of horseradish peroxidase-conjugated avidin (Kem-En-Tec, Denmark) was added and the plates incubated for 45 min. at 20° C. The substrate, reaction time and determination of absorbance were as described above.

The biotinylated MAb was used at a working dilution resulting in approx. 75% of the absorbance at the saturation level on the titration curve. This curve was obtained by using a diluent instead of the competing MAb and serial dilutions of the biotinylated MAb. The extent of blocking by a competitive MAb was calculated according to the formula $(1-A/A_o) \times 100\%$, where A is the mean of the absorbance for three wells with the competing MAb and $A_o$ is the mean of the absorbance of eight wells containing diluent instead of the competing MAb.

The data of 10 representative monoclonal antibodies (MAbs), all of the $IgG_1$ subclass, out of 92 ELISA-positive supernatants are shown in Tables 1 and 2.

TABLE 1

Characterization of 10 representative MAbs

| Hybridoma group No. | Representative MAb | $A_{sat}$ | $C_{50\%}$ ng/ml | Immunoblotting |
|---|---|---|---|---|
| 1 | P3F51 | 1.2 | 110 | + |
| 2 | P3F64 | 0.4 | 250 | + |
| 3 | P3F37 | 0.7 | 30 | (+) |
| 4 | P4F58 | 0.7 | 110 | + |
| 5 | P3F22 | 0.6 | 35 | + |
| 6 | P4F46 | 1.3 | 55 | + |
| 7 | P4F38 | 1.9 | 40 | + |
| 8 | P4F55 | 1.3 | 33 | + |
| 9 | P3F50 | 1.8 | 315 | + |
| 10 | P3F53 | 0.9 | 300 | (+) | a)$A_{sat}$ is the mean absorbance at 492 nm at the saturation level in the ELISA titration.

TABLE 2

Extent of blocking by 10 representative MAbs in the competitive ELISA

| Competing MAb (hybridoma group No. | | Biotinylated detector MAb (% decrease in $A_o^a$) | | | | | | | | |
|---|---|---|---|---|---|---|---|---|---|---|
| | | 1 | 2 | 3 | 4 | 5 | 6 | 7 | 8 | 9 | 10 |
| P3F51 | (1) | 92 | b | | | | | | | | |
| P3F64 | (2) | | 95 | 44 | | | | | | | |
| P3F37 | (3) | | 63 | 95 | 78 | | | | | | |
| P4F58 | (4) | | | 91 | 96 | 73 | | | | | |
| P3F22 | (5) | | | | 71 | 88 | | | | | |

TABLE 2-continued

Extent of blocking by 10 representative MAbs in the competitive ELISA

| Competing MAb (hybridoma group No. | | Biotinylated detector MAb (% decrease in $A_o{}^a$) | | | | | | | | | |
|---|---|---|---|---|---|---|---|---|---|---|---|
| | | 1 | 2 | 3 | 4 | 5 | 6 | 7 | 8 | 9 | 10 |
| P4F46[c] | (6) | | | | | | 92 | 90 | 93 | 16 | |
| P4F38[c] | (7) | | | | | | 93 | 92 | 95 | 27 | |
| P4F55[c] | (8) | | | | | | 92 | 92 | 95 | 15 | |
| P3F50 | (9) | | | | | | 16 | 24 | 13 | 84 | 91 |
| P3F53 | (10) | | | | | | | | | 56 | 83 |
| | $A_o$ | 1.43 | 0.19 | 0.53 | 0.80 | 0.64 | 0.64 | 0.85 | 1.01 | 0.26 | 0.52 |

[a]$A_o$ is the mean absorbance with diluent instead of competing MAb
[b]No blocking (between 12% increase and 9% decrease in $A_o$)
[c]The closely related hybridoma groups 6, 7 and 8 were differentiated by a two-site competitive ELISA using a catching MAb (method not described). Results indicated that group 6 was related to groups 3 and 4, group 7 to no other groups and group 8 to group 1.

The selected hybridoma cell lines were then cloned until they were stable. The resulting clones were then grown in "cell factories" (Nunc, Denmark) at 37° C. in RPMI 1640 medium supplemented with 10% FCS as well as injected about $5\times10^6$ cells/mouse into Balb/c mice which after a certain incubation time leads to the formation of a tumour in the peritoneum of the mouse releasing high quantities of antibody in its ascites (about 5–10 ml containing 5–25 mg/ml).

The hybridoma cell culture supernatants were passed through a protein A agarose column (Kem-En-Tec, Denmark). Bound antibodies were eluted with 0.05M acetic acid, pH 4.0, or 0.03M citric acid, pH 3.0, and immediately neutralized with an appropriate buffer. Purified antibodies were biotinylated as described by Guesdon et al., 1979, (ref. 28).

Two hybridoma cell lines, P3F37 and P3F51 shown in Table 1 to produce MAb, were deposited on Dec. 3, 1987 in the European Collection of Animal Cell Cultures, Centre for Applied Microbiology and Research, Porton Down, Salisbury, Wiltshire SP4 OJG, U.K., with the Accession numbers ECACC 87120301 and ECACC 87120302, respectively.

EXAMPLE 2

Quantification of PMT

Quantification of PMT was carried out by a sandwich ELISA procedure. The sandwich ELISA was initiated by coating each well of a microtiter plate (96 wells Immuno Plate II, Nunc, Denmark) with 50 µl of 2 µg/ml of the anti-PMT MAb, P3F51 (produced in Example 1) in 0.05 M carbonate buffer, pH 9.6 for 16 hours at 4° C. and 1 hour at 20° C. Each well was incubated for 1 hour with 200 µl of phosphate-buffered saline containing 0.05% Tween 20 and 1% bovine serum albumine (PBS-T-BSA). The plates could be stored for at least 6 months by applying 20 µl/well of PBS-sorbitol and sealing with adhesive tape. The analysis was initiated by two PBS-T washings followed by incubation of 50 µl/well of solutions expected to contain PMT. The solutions were appropriately diluted in PBS-T-BSA and incubated for 1 hour at 20° C. After 3 PBS-T washings each well was incubated with 50 µl of 0.5 µg/ml of the biotin conjugated MAb, P3F37, for 1 hour at 20° C. followed by another 3 PBS-T washings and incubation with 50 µl/well of a 1:2,500 dilution of horseradish-peroxidase conjugated avidin (Kem-En-Tec, Denmark) for 45 min. at 20° C. Finally, 50 µl/well of an o-phenylene diamine/$H_2O_2$ solution was added. The reaction was stopped with 2M $H_2SO_4$ after 5 min. and absorbance was determined in an Kontron SLT-210 photometer (SLT Labinstr., Zurich, Switzerland) at 492 nm (ref. 620 nm).

Calibration was performed with a PMT-preparation quantified by amino acid analysis (ref. 6) and all quantitative data were means of at least dual determinations.

Figure 1:
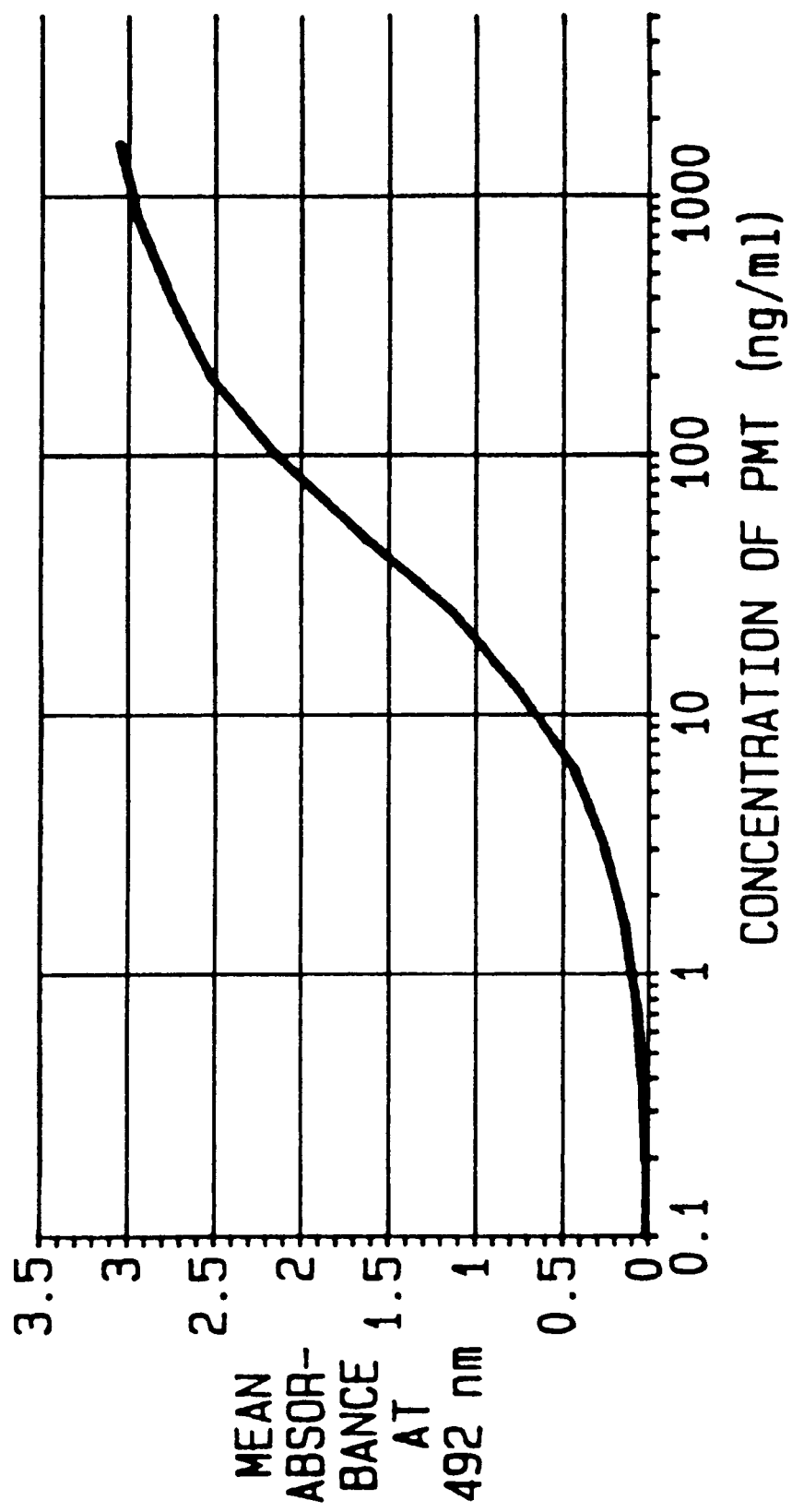
FIG. 1 is a graph showing the titration of PMT in a quantitative sandwich ELISA. The absorbance at 492 nm obtained in the ELISA is plotted against the PMT concentration. The minimum detectable concentration of PMT is about 1 ng/ml corresponding to about 50 $\mu$g or 0.35 fmol.

Using a sandwich ELISA, with the MAb P3F51 as catching antibody and biotinylated MAb P3F37 as detecting antibody, it was possible to detect less than 50 µg of PMT in a 50 µl sample. PMT at a concentration of 1 ng/ml resulted in an $A_{492}$ of approx. 0.1 corresponding to more than 8 times the background absorbance (cf. FIG. 1).

EXAMPLE 3

Affinity purification of PMT

About 100 mg of the protein-A purified MAb P3F51 prepared as described in Example 1 was coupled to 40 ml divinyl sulphone agarose (Mini-Leak, Kem-En-Tec, Denmark) as described by the manufacturer and loaded on a column (2.5×10 cm). The supernatant obtained by cultivation of the toxigenic type D strain P. multocida 45/78 was centrifuged (12,000×g for 30 min. at 4° C.), filtered (Gelman, 0.45 µm), mixed with 1/10 vol. of 1 M Tris-HCl, pH 7.7 and NaCl was added to 0.5 M before application to the affinity column. Repeated washings before elution of the column were carried out with an 0.1 M Tris-HCl buffer containing first 1% Triton® X-100, then 1.5 M NaCl and finally 0.1 M NaCl. All washing buffers contained 0.1% sodium azide and had a pH of 7.8. The PMT was eluted by 0.1 M glycine-HCl, pH 2.8 and immediately neutralized with 1 M $K_2HPO_4$, pH 9.0.

Figure 2:
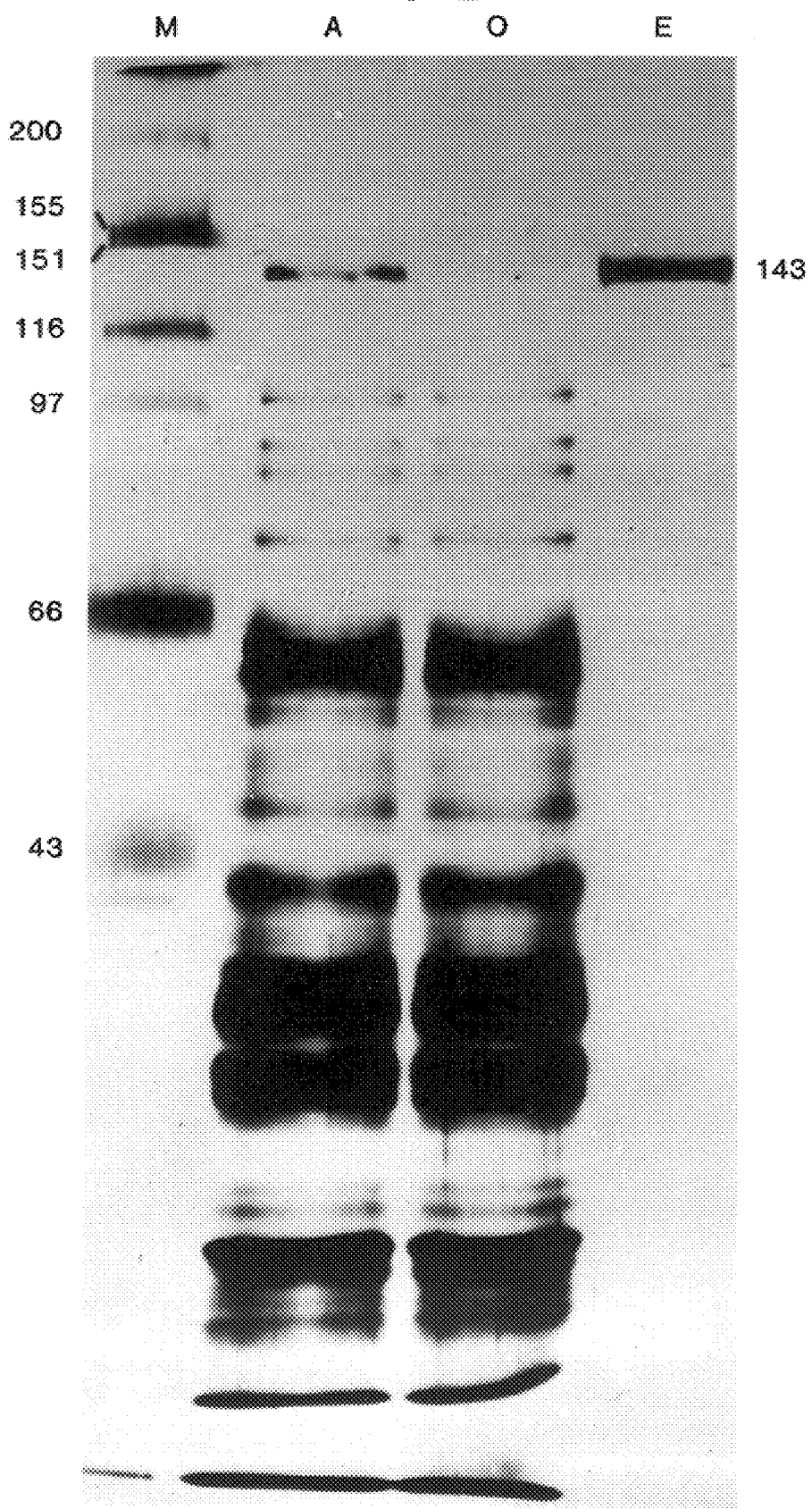
FIG. 2 shows an SDS-PAGE of fractions from the affinity chromatography described in Example 3. Lane A: the culture supernatant applied on the column, lane O: the effluent from the column, lane E: the eluted purified PMT, and lane M: molecular weight marker proteins.
Figure 3:
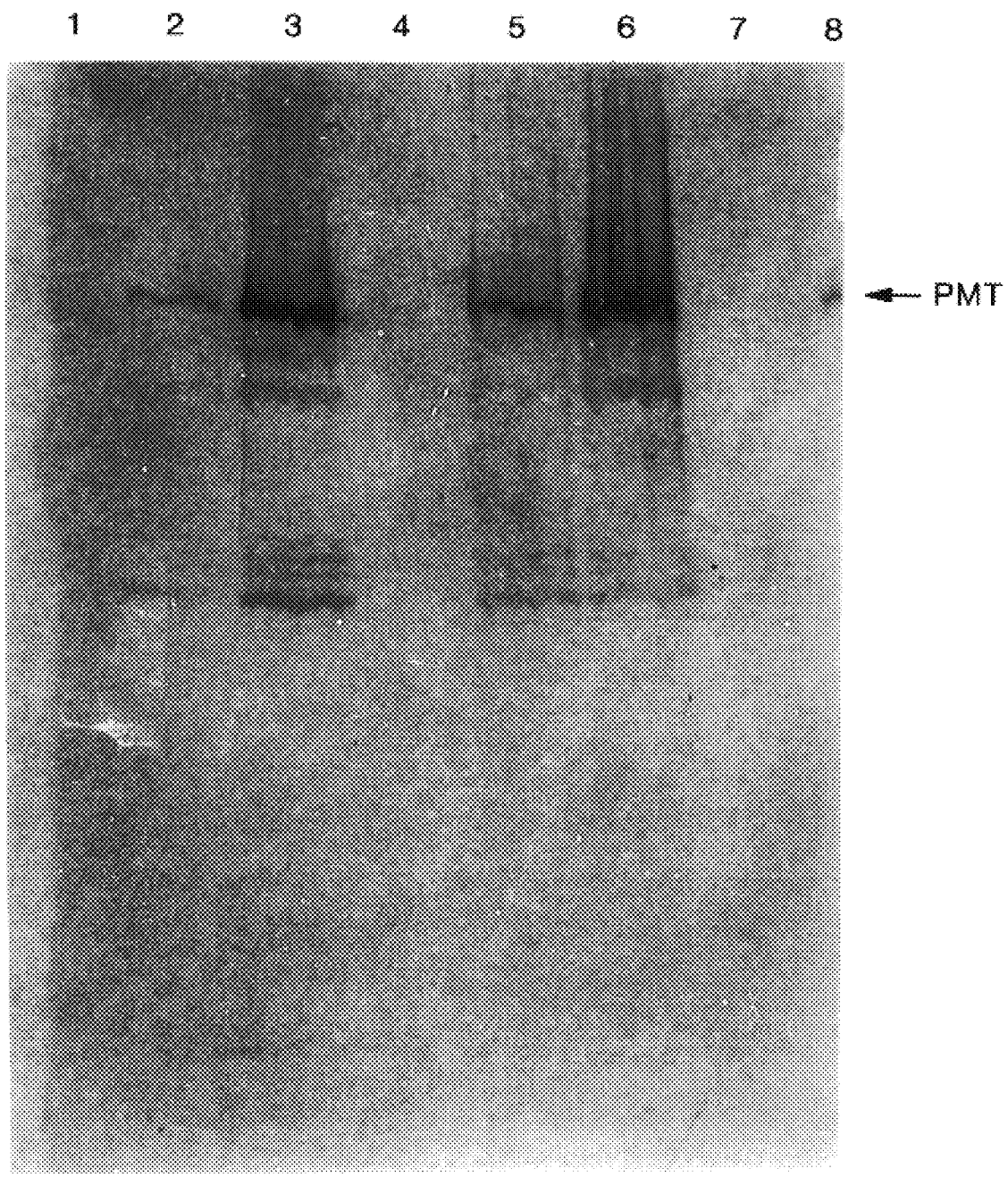
FIG. 3 is a Western blot showing PMT production by the 5 positive recombinant *E. coli* clones detected in the screening procedure. Lane 1: SPE 301; lanes 2 and 3: SPE 308; lane 4: SPE 315; lanes 5 and 6: SPE 312; lane 7: SPE 311; lane 8: purified PMT.
Figure 4:
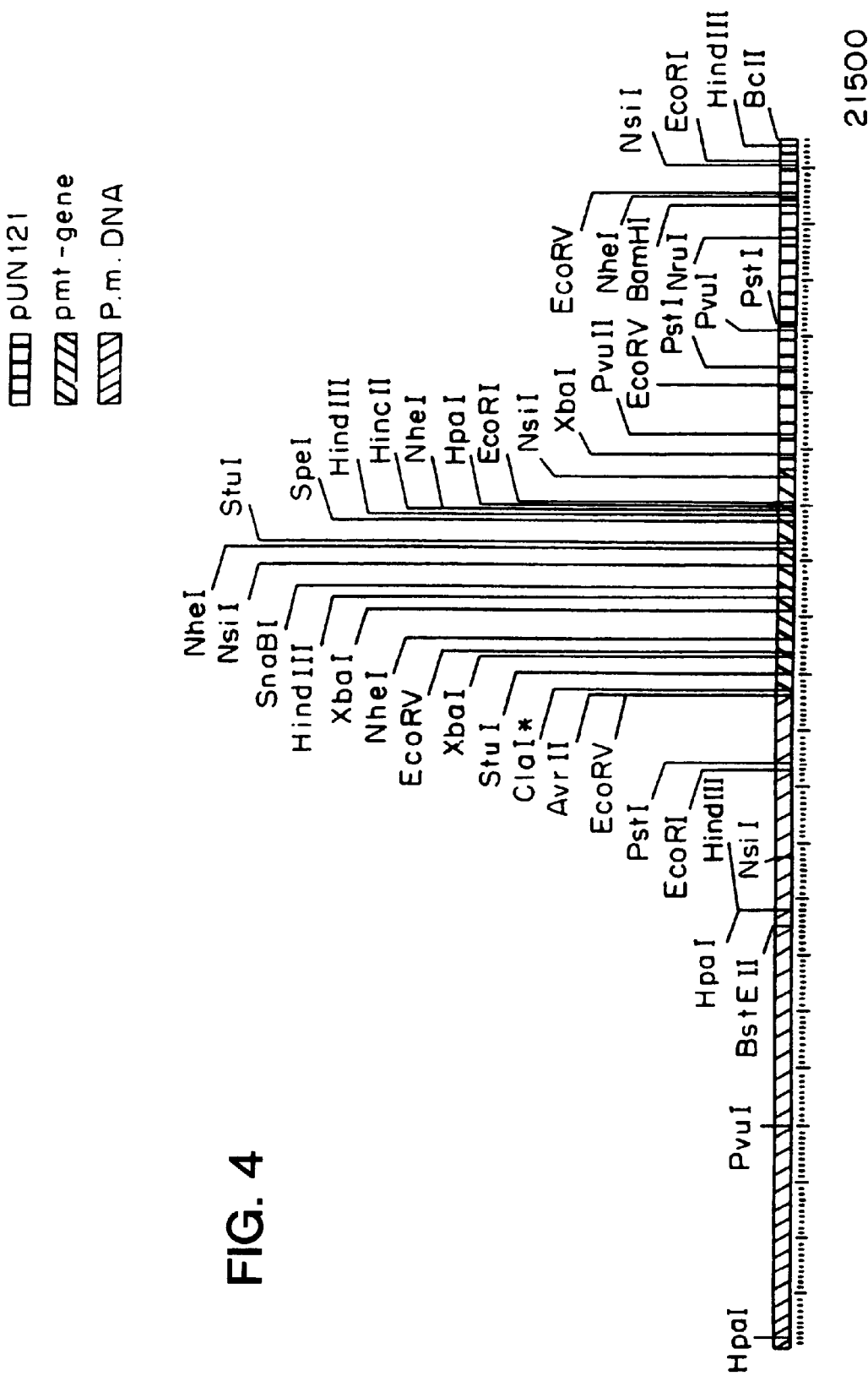
FIG. 4 is a restriction enzyme cleavage map of the plasmid pSPE 308 with a length of 21.5 kb (kilobase pairs).

The presence of PMT in the culture supernatant applied to the affinity column was indicated by the approx. 143 kd protein band seen by SDS-PAGE (FIG. 2). The staining pattern of proteins in the material passing through the column (i.e. the effluent) was identical to that seen with material before application, except for the 143 kd protein, which was retained on the column. Accordingly, the approx. 143 kd protein band is the only staining seen when the protein composition of the eluted material is visualized by SDS-PAGE (FIG. 2).

Approx. 2.67 mg of the 3.41 mg of PMT applied to the column was eluted in a final volume of 8 ml resulting in a 78% yield by affinity chromatography (Table 3). Nearly all the remaining 22% of PMT applied was eluted in fractions with PMT-concentrations below 50 µg/ml.

The specific purity (μg PMT/mg protein) was 284 times higher in the eluted material than in the culture supernatant (Table 3).

The average minimal dermonecrotic dose of affinity purified PMT in guinea pigs after intradermal injection and the average MCD of PMT for embryonic bovine lung (EBL) cells in the standardized EBL-cell test (ref. 29) was approx. 35 ng and 30 μg, respectively. The $LD_{50}$ of PMT in BALB/c mice was 20 to 40 ng (corresponding to approx. 1.5 μg/kg) and in Wistar rats approx. 100 ng (corresponding to 0.5 μg/kg) when administered intraperitoneally in a single dose.

TABLE 3

Purification of PMT by affinity chromatography

|  | Vol. (ml) | Protein (mg) | PMT (mg) | Purification factor | Recovery of PMT, % |
|---|---|---|---|---|---|
| Applied culture supernatant from P. multocida 45/78 | 13,200 | 970 | 3.41 | 1 | 100 |
| Effluent from affinity column | 13,200 | 970 | <0.01 | N.D.[a] | <0.35 |
| Eluted material | 8 | N.D. | 2.67 | 284[b] | 78 |

[a] N.D. not determined
[b] Estimated on the assumption of purity of PMT in the eluted material.

EXAMPLE 4

Establishment of a P. multocida gene library in Escherichia coli

Donor strain

P. multocida strain 45/78. The strain produces a dermonecrotic toxin as described by Foged et al. (ref. 6).

Recipient strain

Escherichia coli K-12 strain MT102. Genotype: thi, araD139, (ara-leu)Δ7697, lacΔX74, galU, rpsL, hsdR. This strain was constructed (by Mogens Trier Hansen, Novo Industri A/S, Denmark) as follows:

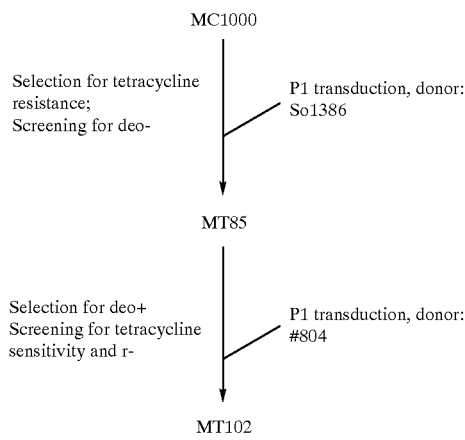

Escherichia coli strain list (all strains are K-12 strains)

| STRAIN | GENOTYPE | REFERENCE OR SOURCE |
|---|---|---|
| MC1000 | araD139, Δ(ara-Leu)7697, ΔlacX74, galU, galK, rpsL. | a) |
| Sø1386 | leu, Δ(deoO-deoC), Tn10-6 (91% co-transducible with deo | b) |
| MT85 | araD139, Δ(ara-leu)7697, ΔlacX74, galU, galK, rpsL, T10-6, Δ(deoO-deoC) | c) |
| ≈804 | met, supF, r−, m+, Δ(gal-lac) | d) | b) from Bente Mygind, Laboratoriet for Biologisk Kemi B, University of Copenhagen, Denmark.
c) constructed by Mogens Trier Hansen as shown above.
a) Casadaban and Cohen, 1980, (ref. 30).
d) Wood, 1966 (ref. 31).

Media

P. multocida was grown in Tryptic Soy Broth purchased from DIFCO. E. coli was grown in LB medium (ref. 27).

Restriction enzymes and T4 DNA ligase were obtained from New England Biolabs and used as recommended by the manufacturer.

DNA extraction

To isolate chromosomal DNA from P. multocida strain 45/78, cells from a 250 ml overnight stationary culture were resuspended in 10 ml 50 mM Tris-HCl, pH 8.0, 100 mM EDTA, and incubated with 25 mg lysozyme for 20 minutes at 37° C. 2 ml of 10% (w/v) SDS were added to the mixture which was mixed and put on ice for 10 minutes. To the solution was then added 15 ml of phenol saturated with TE-buffer (10 mM Tris-HCl, pH 8.0, 1 mM EDTA), after which it was heated to 65° C., mixed gently and cooled on ice. After centrifugation for 30 minutes at 4000×g the aqueous phase was extracted with ether and ethanol precipitated, and the pellet resuspended in TE-buffer. The DNA was further purified by banding in a CsCl density gradient (ref. 27). After purification, the DNA was resuspended in 1 ml TE-buffer.

Preparation of clonable DNA fragments

9–22 kilobase pair (kb) DNA fragments with 5'GATC overhangs were prepared in the following way. Chromosomal DNA prepared as described above was digested partially by incubation with the restriction endonuclease Sau3A. At certain intervals after the incubation had been initiated, fractions of the incubation mixture were stopped with 1/20 volume 0.25 M EDTA. A sample of each fraction was run in a 1% agarose gel in TAE buffer as described in (ref. 27), and a fraction containing 4–22 kb fragments was identified. This fraction was further fractionated on a 8 ml sucrose gradient (40–10%) by layering the DNA on top of the gradient prior to ultracentrifugation at 41000 rpm for 7.5 hours. 0.5 ml subfractions were extracted, diluted with 1 volume TE-buffer, ethanol-precipitated and resuspended in TE-buffer. Two of these, containing 9–16 and 15–22 kb fragments respectively, were used in the following cloning steps.

Cloning procedure

9–16 kb and 15–22 kb DNA fragments with 5'GATC overhangs were ligated with BclI restricted pUN121 (refs. 27 and 19) by means of T4 DNA ligase. Insertion of DNA into the unique BclI site of this vector leads to inactivation of the cI gene, encoding the lambda cI repressor, which subsequently is unable to repress transcription from the plasmid-encoded λ PL promoter into the tetracycline resistance gene. The resulting plasmids were tranformed to competent E. coli MT 102 cells as described in (ref. 27). Positive selection for clones with plasmid inserts is achieved by adding tetracycline to the medium (10 μg/ml). Using standard transformation techniques (ref. 27), 3332 tetracycline resistant recombinant *E. coli* clones were obtained,—100% of them containing inserts, thus constituting a *P. multocida* strain 45/78 gene library in *E. coli*. Colonies of the *E. coli* clones were grown on LB-plates containing 10 μg/ml of tetracycline. A scrape of these colonies was stored at −80° C. in a 20% glycerol solution.

EXAMPLE 5

Identification of *P. multocida* toxin producing *E. coli* clones

Screening procedure

The gene library was screened using the colony blot method to transfer colonies to nitrocellulose (ref. 14).

PMT-producing clones were then detected by incubation of the nitrocellulose filters as follows: A) 15 min. in 50 mM Tris, pH 9.6, 150 mM NaCl, 0.05% Tween-20 (washing buffer) and 2 μg/ml DNaseI, B) 2×10 min. in washing buffer without DNaseI, C) 30 min. in washing buffer and 3% gelatine and heated, D) 2×10 min. in washing buffer with 1% Triton X-100, E) 60 min. in a 10-fold dilution in washing buffer of a previously described hybridoma supernatant P3F51, F) 3×5 min. in washing buffer, G) 60 min. in washing buffer with horseradish peroxidase linked-anti-mouse Ig whole antibodies from Amersham (NA.931) diluted 1:1000, H) 3×5 min. in washing buffer,$_{1}$) 1 min. in 10 mM $Na_2HPO_4$, 10 mM citric acid, pH 5.0 (C/P buffer), and J) approximately 5 min. in a staining solution mixed immediately prior to use consisting of 80 mg dioctylsodiumsulfosuccinate (DONS), 24 mg 3,3',5,5'-tetramethylbenzidine, 10 ml ethanol, 30 ml C/P buffer and 20 μl $H_2O_2$. The enzyme reaction was terminated by incubation in 100 mg DONS in 12.5 ml ethanol and 37.5 ml $H_2O$.

The following clones were found to be positive by this procedure: SPE 301, 308, 311, 312 and 315.

Western blot

The positive clones obtained in the screening procedure were further analyzed using the Western blot technique (ref. 32).

In the Western blot procedure, one ml overnight cultures were pelleted (6000×g for 5 min.) and resuspended in 0.5 M Tris-HCL, pH 6.8, 3% SDS, 15% glycerol, 5% mercaptoethanol and bromophenol blue. The samples were boiled for 5 minutes prior to loading on a gel. Proteins were separated by sodium dodecylsulfate polyacrylamide gel electrophoresis (SDS-PAGE) (11), the separating gel consisting of 7% (w/v) acrylamide (acrylamide/bisacrylamide ratio of 40:1) in 0.4 M Tris, pH 6.8, 0.1% SDS, 0.05% glycerol.

Subsequent transfer to nitrocellulose filters was performed in a semi-dry electroblotter as described by Kyhse-Andersen (25). Further handling of the filters was as described above in the screening procedure.

The results appear from FIG. 3 which shows a Western blot of the 5 positive clones.

The transformant strains SPE 308 (lanes 2 and 3) and SPE 312 (lanes 5 and 6) harbouring the plasmids pSPE 308 and pSPE 312, respectively, were shown to be PMT-producing, whereas SPE 301, SPE 315 and SPE 311 were shown not to be. Purified PMT (lane 8) was used as control. The recombinant toxin produced by SPE 308 and SPE 312 shows the same properties as the native protein with respect to recognition in the competitive ELISA as described in Example 1; the size and the toxic activity in the EBL test (ref. 29) are unchanged.

EXAMPLE 6

Restriction mapping and localization of the PMT gene

The plasmids pSPE 308 and pSPE 312 were analyzed for recognition sequences for restriction enzymes (restriction sites), testing for restriction sites for most of the known enzymes with a 6 base pair (bp) recognition sequence. The results are shown in FIG. 4 (pPSPE 308) and FIG. 5 (pSPE 312). It appears from the figures that the two plasmids carry an approximately 6 kb overlap (from position 11000 to 17000 in pSPE308). The pmt gene is therefore localized within this area.

By constructing end-point deletions in the overlapping areas in pSPE 308 and pSPE 312 a number of plasmids, the pSPE 308 derivatives pSPE 336, pSPE 341, pSPE 344 and pSPE 350 as well as the pSPE 312 derivatives pSPE 338, pSPE 343, pSPE 345, pSPE 347/349 and pSPE 525 were constructed. The extents of the resulting plasmids are shown in FIGS. 6 and 7.

These plasmids were transformed to *E. coli* strain MT 102 and analyzed for the production of PMT by Western blotting as described above.

In the Western blot, a single protein with an apparent molecular weight of 125000 daltons was found. The blot is shown in FIG. 8. The plasmid pSPE 349 coding for this protein is deleted of a region to the right of the EcoR1 site at position 8200 in pSPE 312 (cf. FIGS. 5 and 7). The gene product of plasmid pSPE 349 therefore localizes the position and orientation of the pmt gene (shown as shaded area in FIG. 5). The coding region begins about 3.3 kb upstream of the EcoR1 site at position 8200 in PSPE 312 i.e. around the ClaI site at position 4900. Since the total coding region is estimated to be about 3.9 kb the structural gene ends about position 8800 on the map shown in FIG. 5.

EXAMPLE 7

Sequencing of the pmt gene

The nucleotide sequence carrying the pmt gene as localized in Example 4 was determined using the method described by Sanger et al. (ref. 33). The sequence of 4380 consecutive bp were determined. The DNA sequence of the region is shown in FIGS. 10 (*a*)–(*j*) (SEQ ID NO:1) in which the deduced amino acid sequence (SEQ ID NO:2) is indicated above the DNA sequence starting at position 219. The methionine codon of position 219–221 is preferred as a starting codon to the methionine codon of position 213–218 due to its perfect spacing to the putative ribosome binding site at position 201–210. The region containing the pmt gene was subjected to more detailed restriction mapping by a computer search for all restriction sites for restriction enzymes with 6 bp recognition sequences.

The results are shown in FIG. 9 which shows a high degree of conformity with the previously constructed restriction map.

EXAMPLE 8

Expression of *P. multocida* toxin in *E. coli*

The amount of PMT produced in different recombinant *E. coli* clones was determined by estimating the incorporation of S-35 labelled methionine using the following procedure. Cells were grown in AB minimal medium (ref. 21) supplemented with 0.2% glucose, 1 μg/ml thiamine and 50 μg/ml leucine at 37° C. At an optical density ($OD_{450}$) of 0.6, 1 μl of a 1 mCi/ml S-35 methionine solution (purchased from Amersham, S J. 1015) was added to a 1 ml sample of the culture at 37° C. 3 minutes later, 50 μl of 10 mg/ml unlabelled methionine was added as a chase and after further 3 minutes, the sample was put on ice. Samples were pelleted (6000×g for 5 minutes) and resuspended in loading buffer (0.5M Tris-HCl pH 6.8, 3% SDS, 15% glycerol, 5% mercaptoethanol, bromophenol blue). Subsequently, proteins were separated in SDS-PAGE as described in Example 5. Furthermore, the gel was dried and subjected to autoradiography overnight on a KODAK XAR-5 X-ray film.

Relative amounts of PMT were estimated by scanning of the X-ray film, using the β and β' subunits of the *E. coli* RNA-polymerase as a reference.

Recombinant clones tested in this way were MT102 strains harbouring the plasmids pSPE 312, pSPE 525 (shown in FIG. 11) and pSPE 481 (shown in FIG. 12), respectively. Plasmid pSPE 481 consists of the 7 kb PstI fragment of pSPE 525 ligated to a 1.3 kb PstI fragment of plasmid pPL 195, containing part of the ampicillin resistance gene and the lambda PL promoter and operator region. pPL 195 was constructed by inserting a pUC8 EcoRI-HindIII polylinker (ref. 33) into a EcoRI and HindIII restricted PLc28 vector (ref. 34). The resulting pSPE 481 plasmid carries the lambda PL promoter transcribing into the pmt gene.

TABLE 4

Estimated amount of PMT in the recombinant *E. coli* clones

|  | SPE312 | SPE525 | SPE481 |
|---|---|---|---|
| molecules/cell | <500 | 3000–4600 | 12000–15000 |

Data used in the above calculations

|  | β | β' | PMT |
|---|---|---|---|
| Methionine content (%) | 2.76 (23) | 2.56 (24) | 2.80 |
| Size (kD) | 150 (23) | 155 (24) | 146.5 |
| Molecules/cell (at 2.5–3 doublings/hour) | 4500 (25) | 4500 (25) |  |

Furthermore, the content of PMT in SPE481 was estimated using the following procedure. A 100 ml culture with an optical density ($OD_{450}$) of 5 was pelleted (6000×g for 5 minutes) and resuspended in 10 ml of 50 mM Tris-HCl pH 7.0. The supernatant, which did not contain any PMT, was discarded and the harvested cells were disrupted by sonication. PMT was then further purified on an anion-exchange column as described in ref. 6. The purified PMT was then subjected to a quantitative ELISA as described in Example 2, obtaining an estimated value of 2–5 µg PMT per ml of culture fluid.

The *Escherischia coli* K-12 strain MT102 harbouring the pSPE 481 plasmid has been deposited Mar. 21, 1988 according to the Budapest Treaty in Deutsche Sammlung von Mikroorganismen und Zellkulturen GmbH under the strain designation *Escherichia coli* K-12 SPE 481. The accession number is DSM 4488.

EXAMPLE 9

Production and characterization of toxin derivatives

The following derivatives of toxin-encoding plasmids were constructed with the purpose of producing truncated, i.e. detoxified, toxins which are potentially useful for immunogenic purposes. The constructions were prepared on the basis of the restriction mappings disclosed in Examples 6 and 7. The hypothetical toxin-derived proteins produced from plasmids pSPE A through pSPE Q, proteins A through R, are shown in FIG. 13. All derivatives were optimally expressed from the respective plasmids in strain SG 21059 kindly provided by Susan Gottesmann. The known genotype of this strain is Δgal 1on146::ΔTn10 Δlac.

1) pSPE A. The plasmid was constructed by restricting pSPE 481 with the restriction enzyme StuI prior to ligation. This deletion causes a change of reading frame. However, as described below, a PMT derivative could be detected in Western blotting as well as in the EBL toxicity test. This could be due to a small amount of erroneous frame-shifting in the translation procedure. See FIG. 13.

2) pSPE B. The plasmid was constructed by restricting pSPE 481 with the restriction enzyme XbaI prior to ligation. The plasmid codes for a hypothetical PMT derivative of about 108 kD, lacking amino acids 169 through 468 of PMT. See FIG. 13.

3) pSPE C. The plasmid was constructed by restricting pSPE 481 with the restriction enzyme NdeI prior to ligation. This deletion causes a change of reading frame. However, as described below, a PMT derivative could be detected in small amounts. This could be due to erroneous frame-shifting in the translation procedure. See FIG. 13.

4) pSPE D. The plasmid was constructed by restricting pSPE 481 with the restriction enzymes NdeI and SnaBI and subsequently blunt-ending the resulting ends, using T4 polymerase (purchased from New England Biolabs) as described by the manufacturer, prior to ligation. This deletion causes a change of reading frame. However, as described below, a PMT derivative could be detected in small amounts. This could be due to erroneous frame-shifting in the translation procedure. See FIG. 13.

5) pSPE E. The plasmid was constructed by restricting pSPE 481 with the restriction enzyme HindIII prior to ligation. The plasmid codes for a hypothetical PMT derivative of about 53 kD, since this deletion causes a change of reading frame. See FIG. 13.

6) pSPE F. The plasmid was constructed by restricting pSPE 312 with the restriction enzyme HindIII prior to ligation. Like pSPE E, this plasmid codes for a hypothetical PMT derivative of about 53 kD. See FIG. 13.

7) pSPE G. The plasmid was constructed by restricting pSPE 481 with the restriction enzymes SnaBI and XhoI and subsequently blunt-ending the resulting ends as above, prior to ligation. The plasmid codes for a hypothetical PMT derivative of about 135 kD, lacking amino acids 507 through 568 of PMT. See FIG. 13.

8) pSPE H. The plasmid was constructed by restricting pSPE 481 with the restriction enzymes SnaBI and SpeI and subsequently blunt-ending the resulting ends as above, prior to ligation. The plasmid codes for a hypothetical PMT derivative of about 88 kD, lacking amino acids 569 through 1058 of PMT. See FIG. 13.

9) pSPE I. The plasmid was constructed by restricting pSPE 481 with the restriction enzyme NsiI prior to ligation. The plasmid codes for a hypothetical PMT derivative of about 79 kD, lacking amino acids 634 through 1204 of PMT. See FIG. 13.

10) pSPE J. The plasmid was constructed by restricting pSPE 312 with the restriction enzyme NsiI prior to ligation. The plasmid codes for a hypothetical PMT derivative of about 70 kD. See FIG. 13.

11) pSPE K. The plasmid was constructed by restricting pSPE 481 with the restriction enzyme SpeI and blunt-ending the resulting ends as above prior to ligation. The plasmid codes for a hypothetical PMT derivative of about 117 kD. See FIG. 13.

12) pSPE L. The plasmid was constructed by restricting pSPE 312 with the restriction enzyme EcoRI prior to ligation. The plasmid codes for a hypothetical PMT derivative of about 124 kD. See FIG. 13.

13) pSPE O. The plasmid was constructed by partially restricting non-methylated pSPE 481 with the restriction enzyme BclI prior to ligation. The plasmid codes for a hypothetical PMT derivative of 133 kD, lacking amino acids 30 through 150 of PMT. See FIG. 13.

14) pSPE P. The plasmid was constructed by restricting pSPE 481 with the restriction enzyme SpeI, subsequent treatment with the exonuclease Bal31, restriction with EcoRI and finally treatment with Klenow fragment of DNA polymerase I in the presence of all four deoxyribonucleotides prior to ligation. The plasmid codes for a hypothetical PMT derivative of about 136 kD, lacking amino acids 1043 through 1130 of PMT. See FIG. 13.

15) pSPE Q. The plasmid was constructed from a derivative of pSPE 481, pSPE 680. pSPE 680 was constructed by restricting pSPE 481 with the restriction enzymes BamHI and ClaI, and treatment with Klenow fragment of DNA polymerase I in the presence of all four deoxynucleotides prior to ligation. Subsequently, pSPE Q was constructed by restricting pSPE 680 with EcoRV prior to ligation. The plasmid codes for a hypothetical PMT derivative of 127 kD, lacking amino acids 175 through 246 of PMT.

16) pSPE R. The plasmid was constructed by restricting pSPE 481 with the restriction enzymes SpeI and EcoRI and blunt-ending the resulting ends, as described above, prior to ligation. The resulting plasmid codes for a hypothetical PMT derivative of about 117 kD. See FIG. 13.

The reactivity of selected derivatives with a panel of anti-PMT MAbs has been studied by sandwich ELISA's based on detection with non-competitive combination pairs of MAbs. By this method an antigen-code (Ag-code), i.e. a term indicating the epitope-difference of the derivative compared to PMT, was determined for each derivative.

The minimal cytopathic dose (MCD) on 120 $\mu$l of $1.5\times10^5$ embryonic bovine lung cells has been estimated for some affinity-purified PMT derivatives.

The results of the two studies are indicated in the following table (Table 5):

TABLE 5

| Derivative | L | O | P | B* | C* | G* |
|---|---|---|---|---|---|---|
| Ag-code | PMT-α | PMT-β | PMT-β | PMT-γ | PMT-γ | PMT |
| MCD (ng) | 250 | 30000 | 5 | n.d. | n.d. | n.d. |

*not affinity-purified (sonicates)
n.d.: not done

The antigen-code "PMT" indicates that the derivative reacts indifferently compared to PMT by the sandwich-ELISA, i.e. all epitopes characterized by the panel of MAbs, which are present on PMT can be detected on the derivative. The Ag-code "PMT-x", where x is α, β or γ indicates that the MAb(s) reacting with epitope x on PMT are not reacting with the derivative. The results of these tests shows that epitope α is missing on derivative L, β is missing on O and P and γ is missing on B and C.

The MCD of PMT is approx. 0.01–0.03 ng and it is therefore obvious that the abovementioned derivatives L and O are practically non-cytopathic compared to PMT, whereas P shows slightly remaining cytopathic activity.

A Western blot was made using a mouse anti-PMT antiserum produced as described in Example 1, and using horseradish perioxidase rabbit anti-mouse Ig whole antibody (purchased from Amersham) as the secondary antibody. Strains harbouring the plasmids pSPE A, B, C, D, E, G, H, I and L were shown to react with the anti-PMT antiserum (cf. FIG. 14).

Trials carried out on mice for elucidation of the immunogenic effect of the (O-derivative)

Purpose

To study the immunogenic effect of PMT after deletion in the N-terminal end (O-derivative).

Method

For the trials, BALB/c mice were used. Sexually mature female mice were immunized subcutaneously 2 times at 14 days interval with 0.3 ml O-derivative (2.5–5 $\mu$g/ml) in 20% $_A$lhydrogel (cf. Example 12) in PBS+0.1% zero-mouse-serum.

Simultaneously with the 1st vaccination the female mice were mated. Thus, the 2nd vaccination took place about 1 week before expected birth.

1) About 10 days old the baby mice were divided into 2 groups. Half of them were dripped intranasally with PMT (totally 60 ng PMT), the other half was injected intraperitoneally (i.p.) with PMT in different concentrations. The number of dead animals was recorded.

2) All the adult female mice were bled after killing of the surviving baby mice. The blood samples were analysed by ELISA as described in Example 13 for the presence of antibodies against PMT. Immediately after blood sampling the mice were injected i.p. with different concentrations of PMT. The number of dead animals was recorded.

Schematic trial plan

| Trial week No. | |
|---|---|
| 3 | 31 female BALB/c mice were mated and subsequently immunized with O-derivative |
| 2 | |
| 1 | 31 female BALB/c mice were immunized for the second time with O-derivative |
| 0 | 31 female mice delivered 122 baby mice |
| 1 | the baby mice were divided into group I (61) which was treated intranasally with PMT. Group II (61) which was treated i.p. with PMT |
| 2 | surviving baby mice were killed<br>female BALB/c mice were bled<br>female BALB/c mice were injected i.p. with PMT |
| 3 | the number of surviving female BALB/c mice was recorded and the animals killed<br>Trial finished |

Results are shown in tables 6 and 7.

$LD_{75}$ in non-protected baby mice was about 20 ng PMT injected i.p.

$LD_{50}$ in non-protected adult mice was about 70 ng PMT injected i.p.

Conclusion

It can be concluded that mice born from mothers vaccinated with O-derivative vaccine in the doses described can survive i.p. injection of min. $25\times LD_{50}$ of PMT. The protection is obtained via antibodies transferred via colostrum from mother to offspring.

Furthermore it can be concluded that O-derivative vaccinated animals develop antibodies against PMT, even if some variation is seen. The mice can survive i.p. injection of min. $50\times LD_{50}$ of PMT.

Thus, mice vaccinated with O-derivative can transfer a considerable protection against PMT to the offspring via colostrum. The mice themselves develop antibodies against PMT and are protected against even high concentrations of PMT.

TABLE 6

SCHEME OF VACCINATION TRIALS WITH O-FRAGMENT IN MICE (ADULT)

| | | CO-NC. | Amount of PMT (challenge) | | | | | | |
|---|---|---|---|---|---|---|---|---|---|
| Trial | $\bar{x}$, (s) (ln titer) | (vaccine) | 200 ng | 250 ng | 800 ng | 3200 ng | 4000 ng | 8000 ng | 16000 ng |
| 1 | 6.49 (0.60) | 5 $\mu$g/ml | 0/2* | | 0/4 | 0/4 | | | |
| 2 | 1.27 (1.06) | 5 $\mu$g/ml | | | | | 1/3 | 3/4 | 4/4 |
| 3 | 1.06 (1.10) | 2.5 $\mu$g/ml | | 1/2 | | | 2/4 | | 3/4 |

*Number of dead mice/number of i.p. injected mice

TABLE 7

SCHEME OF TRIAL WITH O-FRAGMENT IN MICE (OFFSPRING)

| | Amount of PMT (challenge) | | | | | |
|---|---|---|---|---|---|---|
| Trial | 20 ng | 30 ng | 100 ng | 150 ng | 500 ng | 750 ng |
| 1 | 0/4* | | 0/7 | | 0/7 | |
| 2 | | 0/9 | | 0/10 | | 8/8 |
| 3 | | 0/1 | | 0/10 | | 4/5 |

*Number of dead mice/number of i.p. injected mice

EXAMPLE 10
Differentiation of PMT+ and PMT− strains by PMT-ELISA 615 field isolates and 7 reference strains of P. multocida were examined. The field isolates were obtained from nasal swabs (603 isolates) and lungs (12 isolates) of pigs from 156 Danish herds and were identified by the following criteria: acid produced from glucose, saccharose, mannitol, sorbitol and not from maltose, arabinose, dulcitol and inositol; and production of indole, ornithine decarboxylase, catalase, oxidase and not of urease.

Extracts for toxin analyses were prepared by harvesting blood agar (9 cm Petri dish) overnight (37° C.) cultures into 2 ml of sterile water by means of a spatula. The suspensions were left for extraction. at 37° C. for approximately 18 hours. One part of the extract was examined directly by PMT-ELISA as described in Example 2. All absorbances (A) were expressed as percentages of the absorbance obtained by a positive control ($A_O$). This control was a 1:1 dilution of an extract, freshly prepared for each test of the toxigenic type D reference strain P. multocida ssp. multocida 45/78.

Another part was centrifuged (30 min. at 1500×g), the supernatant sterile filtered and subsequently examined in the EBL-cell test as described earlier refs. 22 and 29).

The 615 field isolates were characterized as toxigenic (250) or non-toxigenic (365) by the EBL-cell test and were of capsular type A (119 toxigenic and 92 non-toxigenic isolates) or D (131 toxigenic and 273 non-toxigenic isolates).

Full agreement between the EBL-cell test and the PMT-ELISA was obtained for the 615 field isolates and the 7 reference strains (Table 8).

TABLE 8

| | EBL-cell-test a) | PMT-ELISA b) |
|---|---|---|
| 250 field isolates of | + | + |
| P. multocida ssp. multocida | | |
| 365 field isolates of | − | − |
| P. multocida ssp. multocida | | |
| Type strain (CCUG 17977) | − | − |
| P. multocida ssp. septica | | |
| Type strain (NCTC. 10204) | − | − |
| P. multocida ssp. galicida | | |
| Type strain (NCTC 10322) | − | − |
| P. multocida ssp. multocida, type A | | |
| Reference strain (ATCC 12945) | − | − |
| P. multocida ssp. multocida, type A | | |
| Reference strain (NCTC 12177) | + | + |
| P. multocida ssp. multocida, type A | | |
| Reference strain (ATCC 7707) | − | − |
| P. multocida ssp. multocida, type D | | |

TABLE 8-continued

| | EBL-cell-test a) | PMT-ELISA b) |
|---|---|---|
| Reference strain (NCTC 12178) | + | + |
| P. multocida ssp. multocida, type D | | | a) All EBL-positive (+) bacterial extracts bad EBL-titres above $10^3$ (median $10^4$, range $10^3$–$10^6$), in the EBL-cell test, EBL-negative (−) extracts were non-cytopathic.
b) All 1:1 diluted ELISA-positive (+) bacterial extracts had relative absorbances above 39% (mean ± SD: 94% ± 13%) in the PMT-ELISA, whereas all ELISA-negative (−) extracts had relative absorbances below 9% (2.1% ± 1.9%).

Figure 15:
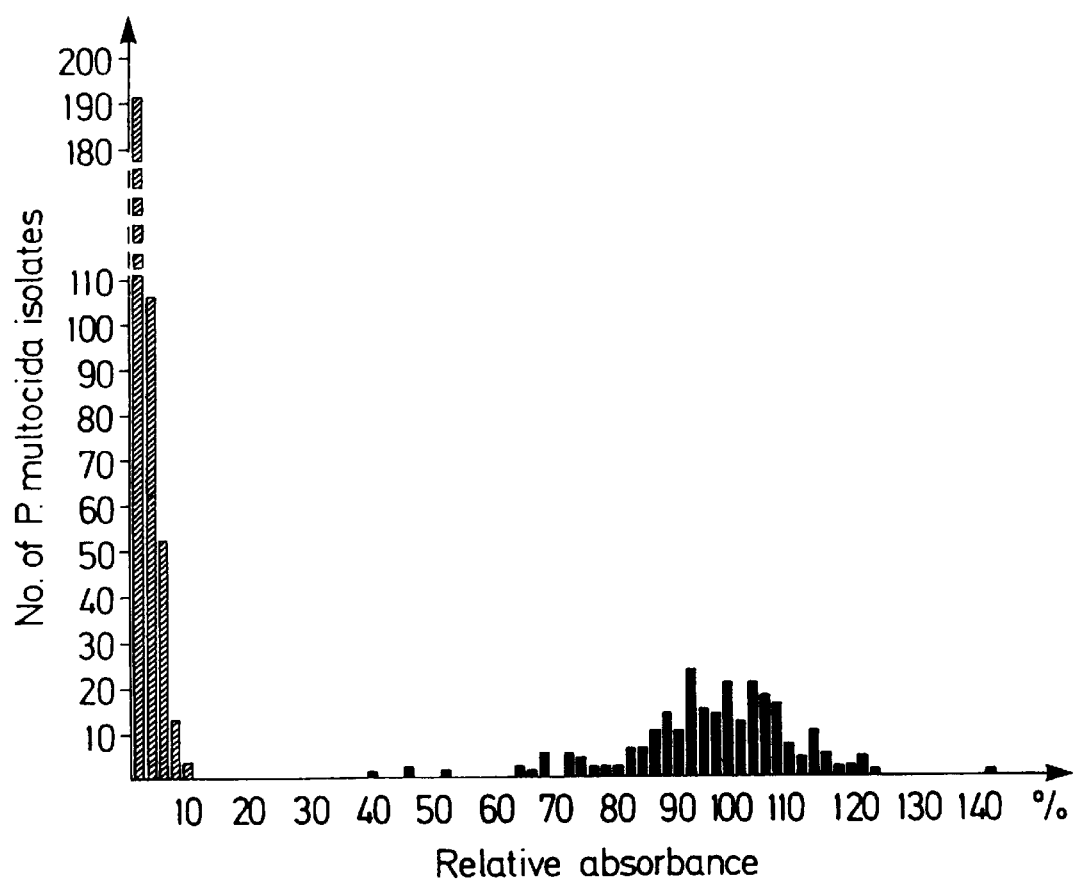
Figure 16:
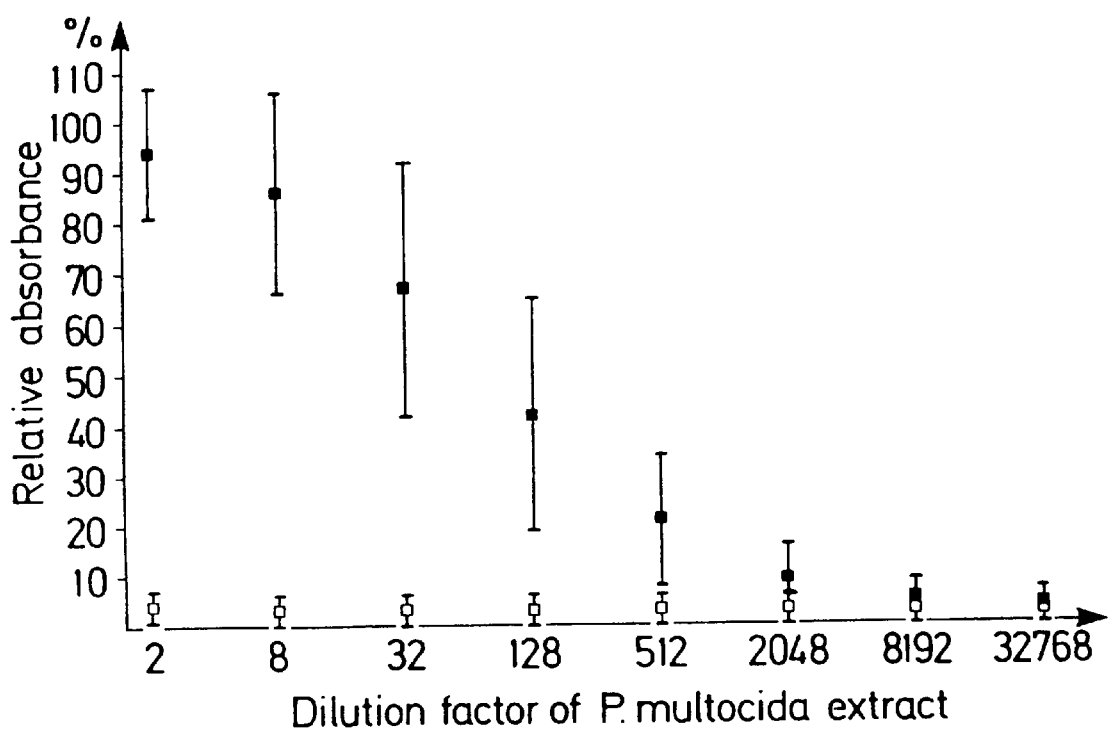

The cytopathic and non-cytopathic extracts of the 615 field isolates were separated in two clearly distinguishable groups by the PMT-ELISA (FIG. 15). Since the mean±SD of the absorbances (A) obtained from the 1:1 diluted extracts of the 250 toxigenic isolates was 1.72± 0.48, visual readings instead of photometric measurements of the ELISA-results would be satisfactory for the differentiation of extracts of P. multocida. The mean±SD of the PMT-concentration in the extracts of the toxigenic isolates of P. multocida was estimated being 2.8±1.9 μg/ml, and since the detection limit of the PMT-ELISA is approx. 50 pg (1 ng/ml) PMT (cf. Example 2), dilutions of the extracts (FIG. 16) and extracts with low PMT-concentrations may appropriately be tested by PMT-ELISA. The main advantages of the PMT-ELISA compared to existing tests are the independence of cell culture or laboratory animal facilities, the ability of a single laboratory worker to handle several hundreds of samples per day and the possibility of obtaining quantitative objective results from bacterial extracts in 4 hours.

EXAMPLE 11
Neutralization of PMT with monoclonal anti-PMT-antibodies

Samples (30 μl) of either PMT in PBS or PMT in a crude cell-free extract of P. multocida 45/78 (ref. 6) containing PMT in amounts up to 12 ng and 1 μg of purified MAb (P3F51) were incubated for 15 min. at 20° C. before application to embryonic bovine lung (EBL) cells (120 μl, 1.5×$10^5$ cells/ml) as described for the original EBL-cell test (ref. 29). The minimal cytopathic dose (MCD) of PMT was estimated when no MAb was present in the sample. The neutralization titer was recorded as the number of MCD which could be neutralized by 1 μg of MAb.

The results appear from Table 9 below.

TABLE 9

| Hybridoma group No. | Representative MAb | Neutralization in EBL-cell test (x MCD)[a] |
|---|---|---|
| 1 | P3F51 | 130 |
| 2 | P3F64 | 70 |
| 3 | P3F37 | <2 |
| 4 | P4F58 | 30 |
| 5 | P3F22 | 40 |
| 6 | P4F46 | 100 |
| 7 | P4F38 | 35 |
| 8 | P4F55 | 40 |
| 9 | P3F50 | 400 |
| 10 | P3F53 | 55 |

[a]Neutralization of the cytopathic effect on PMT was estimated as the number of minimal cytopathic doses (MCD) neutralized by 1 μg of MAb. The MCD of PMT is about 30 pg.

As indicated in Table 9, addition of 1 μg of MAb to PMT 15 min. before addition to the EBL-cells resulted in a 30 to 400 times increase of the MCD for 9 out of the 10 representative MAbs, whereas MAb P3F37 had a very low neutralizing effect on PMT. The neutralization of the cytopathic effect of PMT was also achieved when a crude cell-free extract of P. multocida 45/78 was used instead of pure PMT.

Samples (200 µl) containing PMT in variable amounts up to 2.56 µg and purified MAb (P3F51) in amounts between 0.15 and 15 µg were incubated for 15 min. at 20° C. and injected intraperitoneally (i.p.) in female BALB/c mice (6 weeks old, 15 to 20 g). Mice dying within a week from the time of PMT injection were recorded and the lethal dose of PMT and the neutralizing effect of the MAb was estimated. When 1.5 or 15 µg of P3F51 were added the lethal dose of PMT increased about 4 and 32 times, respectively, whereas 0.15 µg of the MAb had no neutralizing effect.

To study the in vivo neutralization ability of anti-PMT monoclonal antibodies a 200 µl solution containing 15 µg of purified monoclonal antibody (P3F51) was injected (i.p.) in female BALB/c mice (6 weeks old, 15–20 g) 2 days before i.p. administration of a 200 µl solution containing PMT in varying amounts up to 2.56 µg either in a pure form or as a crude cell-free extract of P. multocida 45/78 (ref. 6). The neutralizing effect was estimated as described above.

The lethal dose of PMT increased about 32 times when mice were passively immunized with 15 µg of P3F51 2 days before challenge with PMT or a crude cell-free extract of P. multocida 45/78.

EXAMPLE 12
Vaccination with purified PMT or derivative O 15 mg of PMT purified as described in Example 3 in 45 ml of PBS was dialyzed against 0.35% formaldehyde in PBS, pH 7.3–7.9, for 36 hours at 4° C. after which 1 g/l lysine-HCl was added to the dialysis liquid, and after 18 hours the dialysis was continued with repeated changes of PBS. The thus produced detoxified PMT was analyzed for lack of (or sufficiently reduced) toxic activity in the mouse lethality test and the cytopathic test on EBL-cells described above as well as a dermonecrotic test in guinea pigs as described by Foged et al. (1).

10 mg of biologically inactive (detoxified) PMT in 40 ml PBS was then coupled to 10 ml aluminium hydroxide gel purchased from Superfos, Denmark, under the trade name Alhydrogel as recommended by the manufacturer and diluted in 20% aluminium hydroxide in PBS to a final concentration of about 5 µg/ml or 125 µg/ml detoxified PMT.

Gestating gilts were immunized subcutaneously 4–6 weeks and 2–3 weeks before farrowing with a dose of 3 ml of the detoxified PMT vaccine composition prepared above. After farrowing piglets were inoculated intranasally with Bordetella bronchiseptica and P. multocida as described in ref. 1 and the protective effect of the immunization of the sows was estimated by measuring the average daily weight gain before slaughtering of the pigs (at about 90 kg live weight) and determination of osteopathological conditions in the snout of the pigs at slaughtering. Pigs from immunized sows were compared to pigs from non-immunized sows and the protective effect of the immunization is shown in Table 10.

TABLE 10

| | No. of animals (litters) | Mean daily weight gain after weaning | No. of animals with severe turbinate atrophy (%) |
|---|---|---|---|
| Pigs from non-immunized sows | 61 (8) | 781 g | 49 (80.3%) |
| Pigs from immunized sows | 174 (20) | 848 g | 20 (11.5%) |

In a study still in progress gilts were immunized with 50 µg/dose of affinity-purified derivative O from sonicates of an E.coli clone containing pSPE O as described in Example 9. No modifications of O were performed except for coupling to Alhydrogel. Preliminary results of the vaccination study indicates that:

a) the serum- and colostrum titers against native PMT are similar for gilts vaccinated with derivate O and formaldehyde treated PMT, b) the specific antibodies are transferred to piglets through colostrum equally well in both vaccine groups.

c) the clinical symptoms of atrophic rhinitis are prevented equally well in the progeny from gilts vaccinated with O (O-piglets) and formaldehyde treated PMT (P-piglets), and that this prevention seems to be close to 100%, when compared to piglets born by unvaccinated gilts (control piglets).

d) the toxigenic P. multocida used for the experimental infection can be reisolated in significantly higher rates from control piglets than from O- or P-piglets at 5 weeks of age.

EXAMPLE 13
Detection of anti-PMT-antibodies

Figure 17:
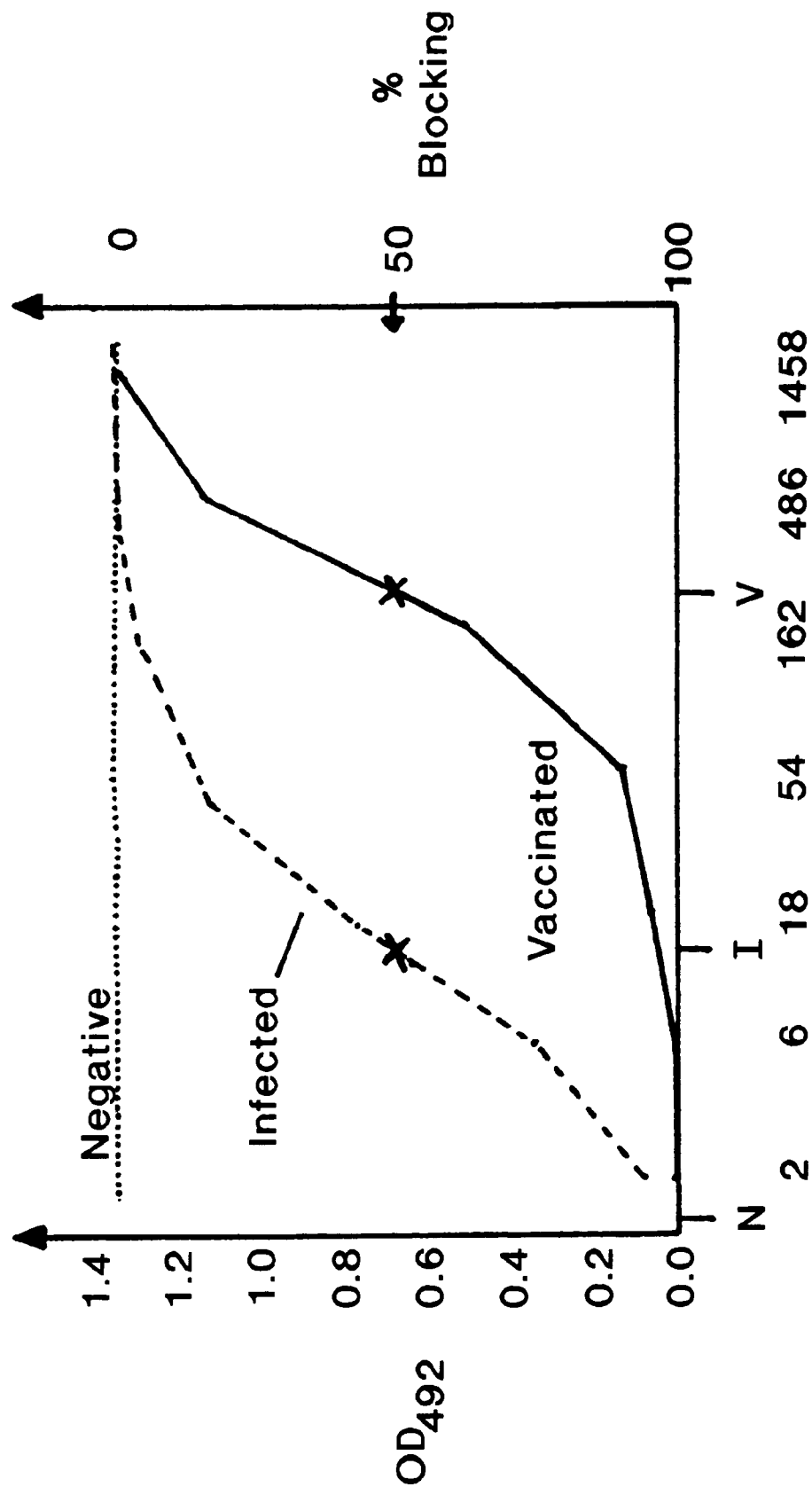

By proceeding substantially as described in Example 2, but by incubating the coating monoclonal anti-PMT-antibody with a premixed preparation of serum and a constant amount of PMT, it is possible to detect anti-PMT-antibodies in serum of for instance pigs infected with P. multocida or of animals vaccinated with a vaccine of the invention. The mixture which was prepared for concentrated or diluted serum samples was incubated for 30 min. at 37° C. before incubation for 15 min. in the microtiter plate. The presence of anti-PMT-antibodies in the serum sample was detected by a decrease in absorbance measured substantially as described in Example 1 (the section entitled "ELISA for estimating epitope specificity"). The results are shown in FIG. 17 which shows the 50% blocking titers of serum from an anti-PMT-antibody negative pig (<2), a pig infected with a toxin-producing P. multocida strain (about 14) and a gilt vaccinated with the vaccine described in Example 12 (about 250).

EXAMPLE 14
Detection of PMT by colony blot and immunoblotting

The presence of PMT in samples may be detected by a colony blot method (ref. 14) as described in Example 5 (the section entitled "Screening procedure")

Similarly, the presence of PMT in samples may be detected by separating proteins in the samples electrophoretically by SDS-PAGE (as described in Example 1) and transferring them electrophoretically to a nitrocellulose membrane where PMT, if present, can be visualized by immunoblotting as described in Example 1 (in the section entitled "Immunoblotting"). The electrophoretic location of the stained protein band also gives the apparent molecular weights of PMT (approximately 143 kd).

EXAMPLE 15
Genetic distinction between PMT+ and PMT− Isolates of *P. multocida* as determined by colony hybridization

*P. multocida* isolates (17 toxin-positive and 18 toxin-negative strains as determined by ELISA and EBL tests as described above) were inoculated on Tryptic Soy Broth Agar plates (purchased from DIFCO). After incubation overnight at 37° C., a replica was made on a nitrocellulose membrane filter (Schleicher & Schull BA 85). This replica was placed (face up) on top of 4 consecutive Whatman 3MM filters which were soaked in 10% SDS, denaturation buffer (0.5M NaOH, 1.5M NaCl), neutralization buffer (0.5M Tris-HCl pH 8.0, 1.5M NaCl) and 2×SSPE (360 mM NaCl, 20 mM $NaH_2PO_4$, 2 mM EDTA pH 7.4), respectively. Incubation was carried out for 5 minutes on each filter at room temperature. Subsequently, the nitrocellulose filter was dried and DNA was fixed to the filter by baking at 80° C. for 2 hours. Prehybridization and hybridizations were done in 6×SSC (0.15M NaCl, 0.015M sodium citrate, pH 7), 0.5% SDS and 5×Denhardt solution for 2 hours and overnight, respectively, at 65° C. The probe was a radioactively labelled XbaI fragment from position 1623 to 4376 in the sequence shown in FIGS. 10 (*a*)–(*j*) (SEQ ID NO:1) prepared by the nick translation method (ref. 22). After hybridization the filter was washed at 25° C. in 2×SSC, 0.5% SDS for 2×15 min. and in 0.2×SSC, 0.5% SDS for 2×1 hour at 65° C. and left for autoradiography overnight.

Figure 18:
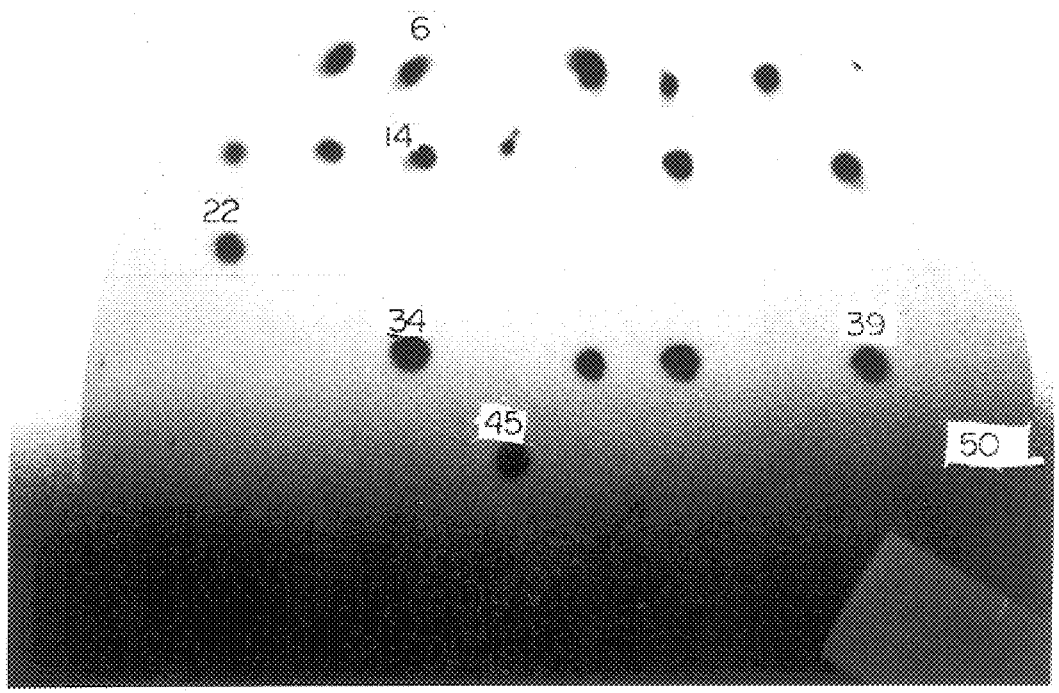

The results appear from FIG. 18 which shows that colonies at positions 5, 6, 8, 9, 10, 12, 13, 14, 15, 17, 19, 22, 34, 36, 37, 39, 45 and 50 were PMT+ and colonies at positions 7, 23, 24, 26, 28, 30, 32, 42, 44, 47, 48, 53, 56, 58, 63, 66, 73 and 75 were PMT−. These results are in accordance with the ELISA and EBL determinations. Hence, non-toxigenic strains of *P. multocida* owe their lack of toxin production to a lack of the PMT encoding pmt gene.

EXAMPLE 16
Purification of rPMT and comparison of rPMT with PMT

In the toxin purification procedure, cells harvested from a 1 l overnight stationary culture of SPE312 were resuspended in 10 ml of $H_2O$ and sonicated several times for 0.5 min. at 0° C. using a Branson sonifier 250 (Branson, Conn., U.S.A.). The sonicate was diluted to 50 ml in 0.1 M Tris-HCl, pH 7.8 containing 0.5 M NaCl before appliation to the affinity column which was prepared by immobilizing the anti-PMT Mab P3F51 as described in Example 3. After repeated washings of the affinity column, rPMT was eluted with 0.1 M glycin-HCl, pH 2.8 as earlier described for the affinity purification of PMT from extracts of toxigenic *P. multocida*. All fractions were immediately neutralized with 1 M $K_2HPO_4$.

A diluted bacterial sonicate of SPE312 containing approximately 82 µg of rPMT as determined by the quantitative ELISA described in Example 2 was applied to a 1-ml affinity column to which was coupled approximately 5 mg of anti-PMT MAb P3F51. No rPMT could be detected in the effluent from the column. Upon elution approximately 75 µg of rPMT was obtained in the two main fractions of 1.4 ml each. This corresponds to a recovery of 91% of the applied rPMT.

PMT assays

Quantification of rPMT was done as described for PMT (Example 2) using the capture anti-PMT MAb P3F51 and the biotinylated detector MAb P3F37 in the PMT-ELISA, a sandwich ELISA based on the same technique as explained below for the study of epitopes on rPMT and PMT. Quantification by the PMT-ELISA was compared to results obtained in a modified Coomassie brilliant blue dye-binding microassay previously used for the determinations of protein concentrations and dye-binding ability of PMT compared to bovine serum albumine (BSA).

Comparison of epitopes on rPMT and PMT was done by sandwich ELISA's based on 10 anti-PMT MAbs (Example 1) purified from hybridoma supernatants on protein A-agarose columns. These MAbs have been shown to react with different epitopes on PMT. The sandwich-ELISA's were done as described in Example 2. Dual determinations were performed for both antigens in all 100 combinations of the 10 catching MAbs and the same biotinylated detecting MAbs. Combination pairs of MAbs resulting in absorbances below 0.3 were considered competitive. For the non-competitive combination pairs, the results were described as the mean of dual determinations of absorbance obtained for rPMT relative to the mean of dual determinations of absorbance for PMT.

The dermonecrotic and lethal effects of rPMT and PMT were determined by injecting 200 µl of dilutions of the previously ELISA-quantified samples intradermally into guinea pigs or intraperitoneally into BALB/c mice, respectively. Samples resulting in a dermal lesion of 10 mm or more at 48 h after intradermal injection were scored as dermonecrotic and samples resulting in death in less than 5 days after intraperitoneal injection were scored as lethal. All results were based on at least duplicate determinations.

Affinity-purified rPMT and PMT had very similar patterns of reactions in the structural ELISA test based on 100 combination pairs of 10 different anti-PMT MAbs and 100 ng/ml of affinity purified antigen. For PMT 25 pairs resulted in an absorbance value ($A_{492}$) below 0.3 which was considered to indicate competitiveness. The same 25 pairs showed competitive reactions when the antigen was 100 ng/ml rPMT. The remaining 75 non-competitive combination pairs resulted in $A_{492}$ values above 0.3 both when PMT and rPMT was used. The overall mean±SD for the 75 calculated values of the relative absorbances of rPMT compared to PMT was 112%±8%. Only minor differences from the overall mean were observed for the mean values for the 10 catching MAbs and the 10 biotinylated detector MAbs.

PMT and rPMT reacted very similarly when tested for cytopathic effect on EBL-cells, for dermonecrotic activity in guinea pigs, and for lethality in mice, and their ability to bind Coomassie brilliant blue were equal and approximately 2.5 times weaker than the dye-binding ability of BSA (Table 11).

TABLE 11

Cytopathic, dermonecrotic, lethal and dye-binding effects of PMT and rPMT

| Sample | minimal cytopathic dose (pg) | minimal dermonecrotic dose (ng) | minimal lethal dose (ng) | dye-binding (%)[a] |
|---|---|---|---|---|
| PMT | 20–40 | 15–45 | 25–50 | 40–45 |
| rPMT | 20–40 | 35 | 30 | 35–45 |

[a]The concentration of BSA relative to the concentration of sample resulting in equal colour formation in the Coomassie brilliant blue dye-binding microassay.

EXAMPLE 17
Examination of *E.coli* and *P. multocida* sonicates for cytopathic activity Sonicates of *E.coli* SPE312 and *P. multocida* 45/78, prepared as described in Example 16 were tested for cytopathic effect in the embryonic bovine lung (EBL) cell test (ref. 29). A row of 5-fold dilutions was prepared for each sonicate and 30 µl of each sample was applied to 1.8×10⁴ EBL-cells in 120 µl of culture medium and the mixture incubated for 3 days at 37° C. before fixation and staining. Samples which resulted in monolayers of EBL-cells morphologically discernible from the epithelial-like swirling patterns of negative control culture, were scored as cytopathic. The cytopathic effects for affinity purified rPMT and PMT in the EBL-cell test were determined in the same way. The minimal cytopathic dose (MCD) for the samples was calculated as minimal amount of rPMT or PMT, determined by the quantitative PMT-ELISA causing a cytopathic effect.

Neutralization of the cytopathic effect of *E.coli* SPE 313 sonicate by anti-PMT MAbs was compared to neutralization of pure PMT: Samples (30 µl) containing approximately 1 µg of MAb and varying amounts of sonicate or PMT were incubated for 15 min. at 20° C. before application to EBL-cells. The results were recorded as the number of MCDs neutralized by each MAb, and as the ratio between the number of neutralized MCDs of the sonicate and pure PMT for each MAb.

Figure 19A:
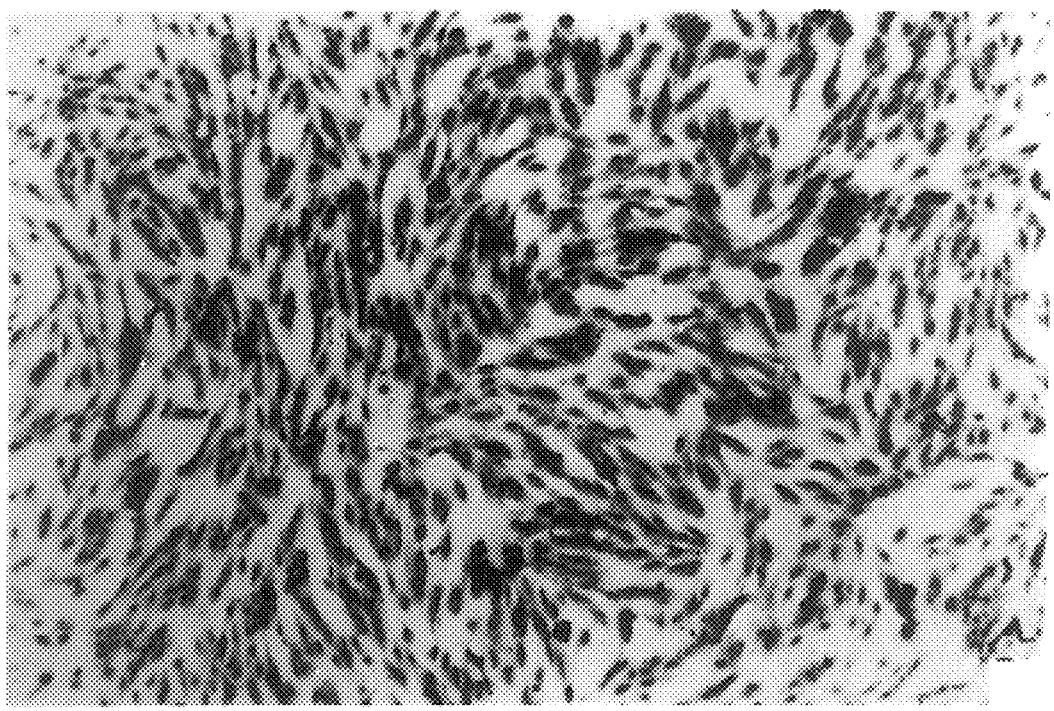
Figure 19B:
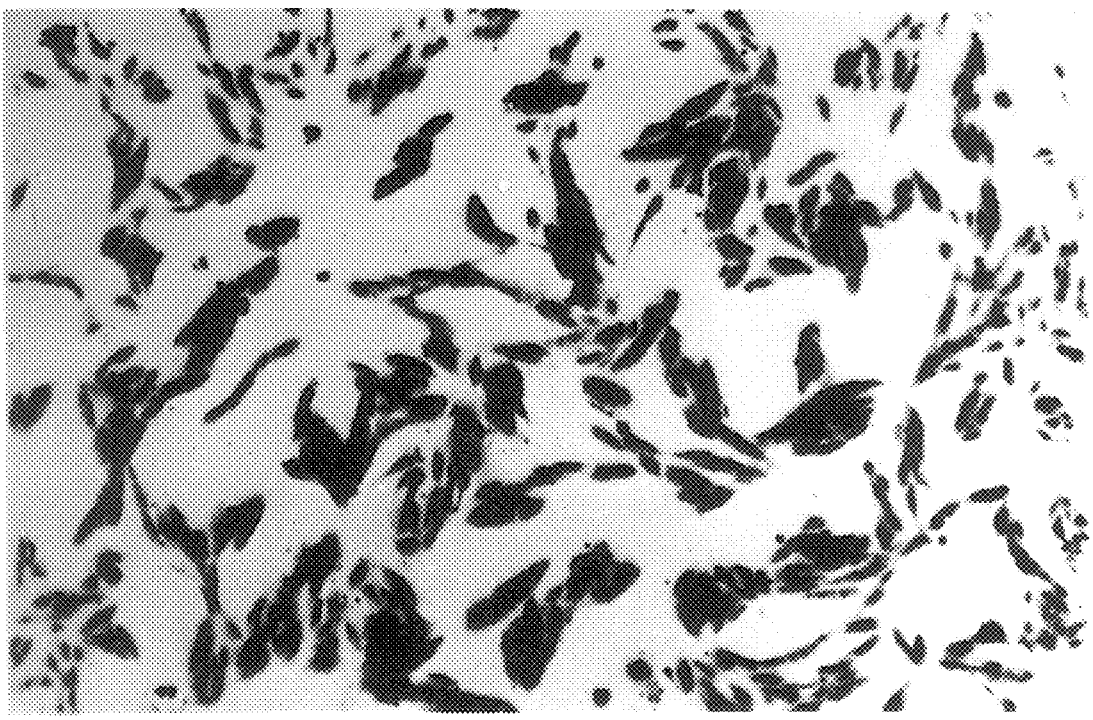
Figure 19C:
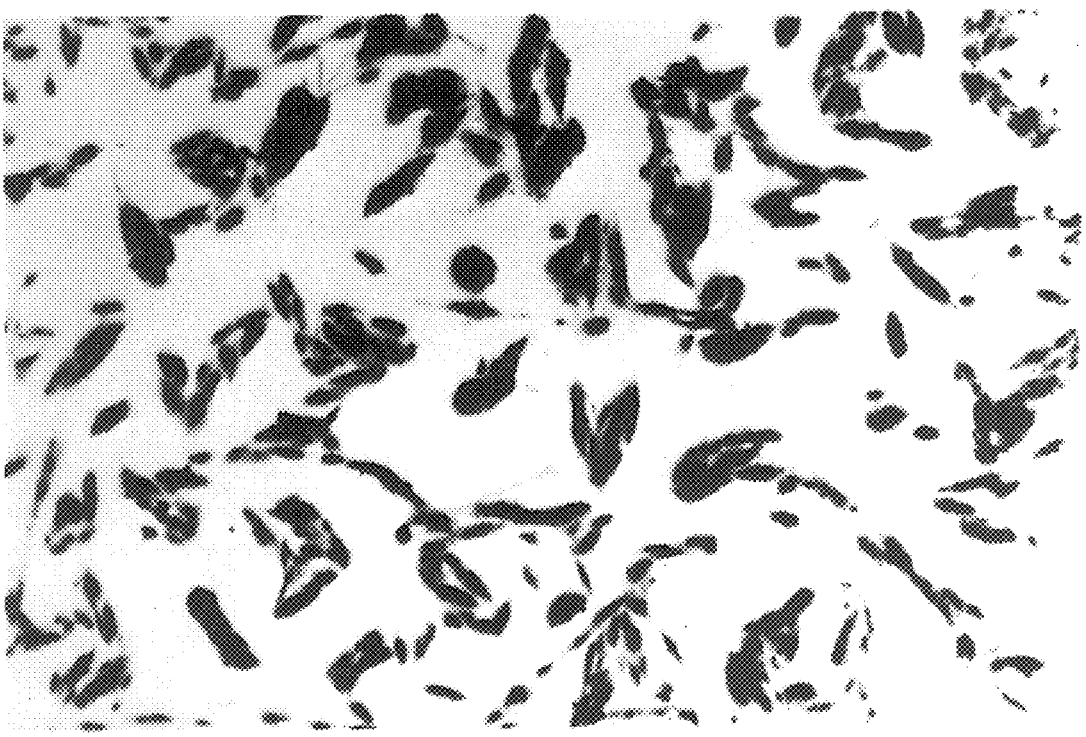

Sonicates of SPE308 and SPE312 were shown to cause morphological changes of embryonic bovine lung (EBL) cells, identical to those caused by toxigenic strains of *P. multocida* (FIG. 19 (data for SPE308 not shown)). As observed for pure PMT, the cytopathic effect of the sonicate of *E.coli* SPE312 could be neutralized by incubation with anti-PMT MAbs. Between 5 and 125 times MCD of the sonicate could be neutralized by various anti-PMT MAbs, whereas between 3 and 125 times MCD of the pure PMT were neutralized. The overall mean±SD for the 10 calculated values of the relative number of neutralized MCDs of *E.coli* SPE312 sonicate compared to PMT was 95%±32X. A PMT-unrelated MAb used as a control did not neutralize the effects of the two cytopathic preparations.

EXAMPLE 18

Analysis of the nature of the DNA flanking the pmt gene

In an attempt to investigate the nature of the DNA flanking the pmt gene in *P. multocida* 45/78, chromosome walking was performed as described in ref. 37. By using a colony hybridization procedure plasmids carrying *P. multocida* DNA were isolated from the *P. multocida* gene library described in Example 4.

Probes

The plasmid pLOL03 was constructed by subcloning a 0.8 kb AccI-HindIII DNA fragment of pSPE344 (FIG. 20) in the vector pGEM-blue (Promega, Wis., USA). The plasmid pLOR02 was likewise constructed by subcloning the 2.4 kb EcoRI-BglII fragment of pSPE312 (FIG. 20) in the vector pGEM-blue. The *E.coli* K12 strain DH5alpha (BRL, Md., USA) was used as host strain for pLOL03 and pLOR02. pLOL03 and pLOR02 in linearized forms were used for generating RNA probes of the *P. multocida* DNA carried by these plasmids. The RNA probes were radioactively labelled using the Riboprobe System II procedure (Promega, Wis., USA), and used in the colony hybridizations and Southern blots described below.

Colony hybridization

The *P. multocida* gene library was spread in appropriate dilution on several LB-plates containing 10 µg/ml tetracycline, and incubated overnight at 37° C. Replicas of the plates were made on nitrocellulose membrane filters, and the cells were lysed and the DNA fixed to the filters as described in example 15.

Prehybridization and hybridization was performed at 65° C. in 50% formamide, 6×SSC (0.15 NaCl, 0.015 M tri-sodium citrate, pH 7.0), 0.1% SDS, 5×Denhardt's solution and 200 µg/ml denatured Salmon sperm DNA for at least 2 hours and overnight, respectively. After hybridization, the filters were washed twice at room-temperature in 1×SSC, 0.1% SDS, and twice at 65° C. in 0.1×SSC, 0.1% SDS. After washing, the filters were left overnight for autoradiography.

Figure 20:
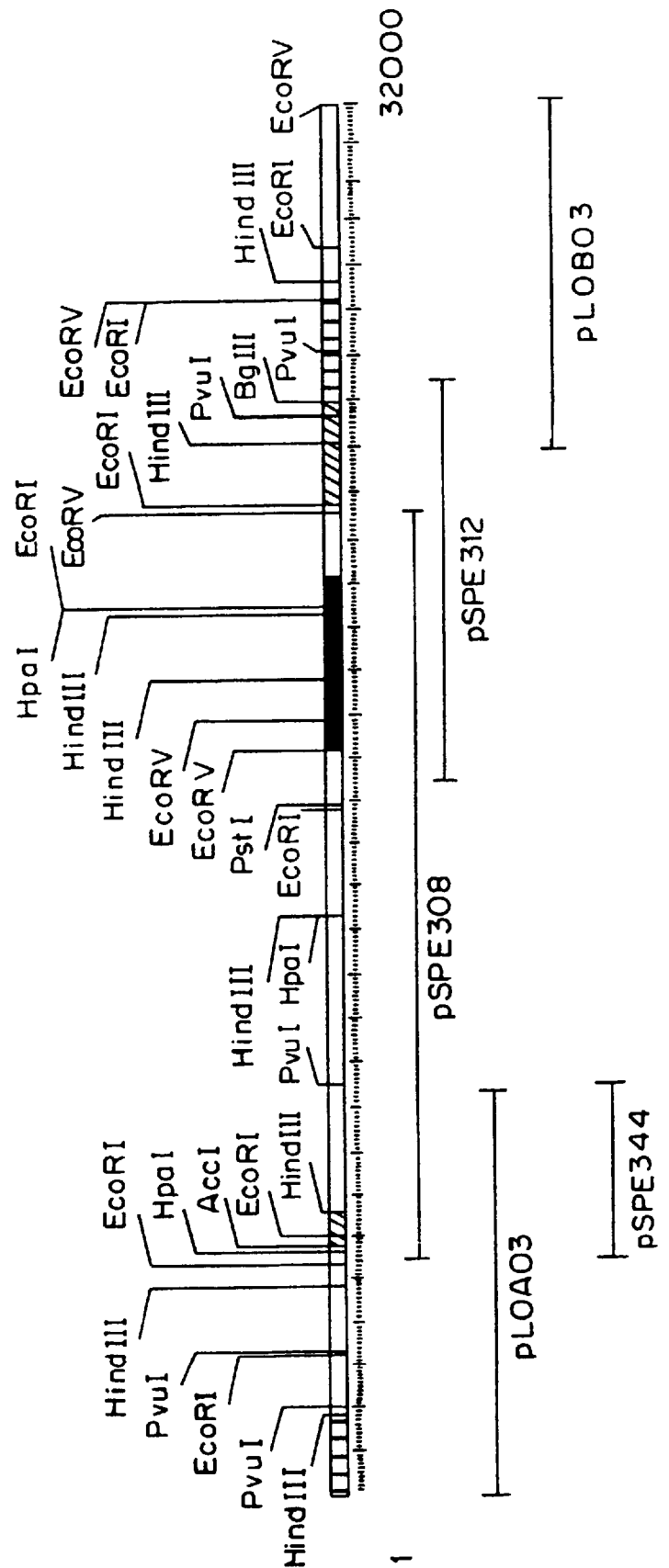

This procedure resulted in the isolation of a number of clones carrying *P. multocida* DNA flanking the inserts in pSPE308 or pSPE312. These clones were further analyzed using the Southern blot technique (ref. 17). The Southern blots showed that the following plasmids were recognized by the RNA probe coded for by pLOL03: pLOA01, pLOA02 and pLOA03. Similarly the plasmids pLOB01, pLOB02 and pLOB03 were recognized by the RNA probe coded for by pLOR02.

pLOA03 (approx. 14.2 kb) and pLOB03 (approx. 12.7 kb) carried the largest inserts. Their restriction maps and a Southern blot analysis show that pLOA03 and pSPE308 contain overlapping DNA of approximately 4.0 kb and that pLOB03 and pSPE312 contain overlapping DNA of approximately 1.7 kb as shown in FIG. 20.

Figure 21:
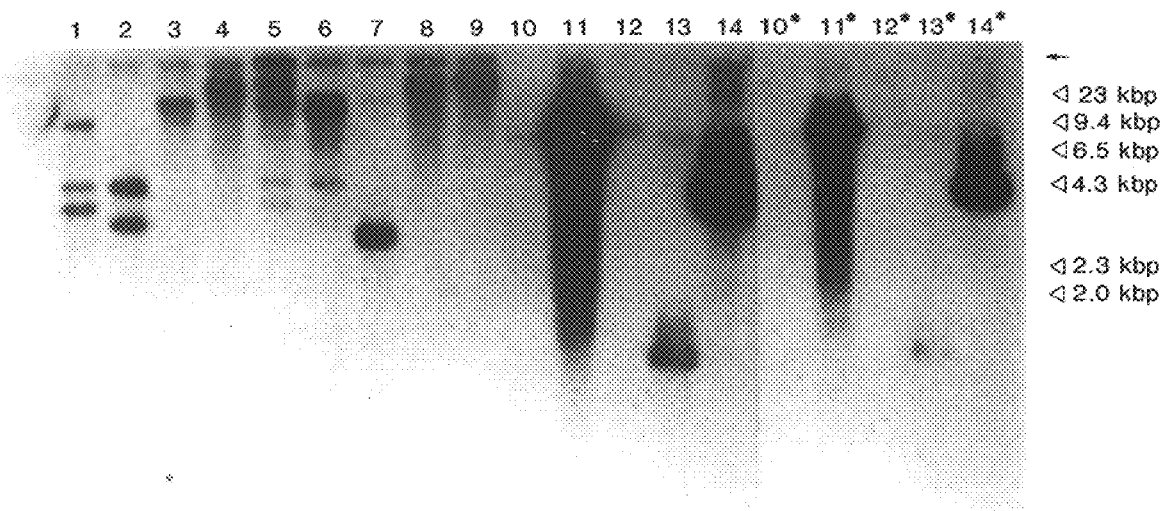

A Southern blot was made using DNA extracted as described in Example 4 (a KI gradient (0.875 g/ml) was used instead of the CsCl₂ gradient) from the toxigenic *P. multocida* 45/78 and from a non-toxigenic *P. multocida* strain MH81P8, type D (ref. 36) and the plasmids pLOA03, pLOA02, pSPE308, pSPE312 and pLOB03 digested by restriction enzymes as indicated in FIG. 21. The probe was the 2.4 kb BglII-EcoRI fragment of pLOB03 radioactively labelled by nicktranslation (Rigby et al., 1977, (ref. 19)). The result shows that:

1) The probe recognizes a DNA sequence on each of the plasmids pLOA03 and pLOB03. Thus, there is a homologous sequence on each side of the pmt gene. The distance between these homologous sequences is approximately 25 kb.
2) The probe recognizes distinct fragments of the chromosomal DNA of both *P. multocida* strains used in this Southern blot.

The above findings could indicate that the DNA flanking the pmt gene and thus the pmt gene itself has originally been carried by a bacteriophage, a transposon, a plasmid or another genetic element which is integrated into the bacterial chromosome.

Dot blot

Figure 22:
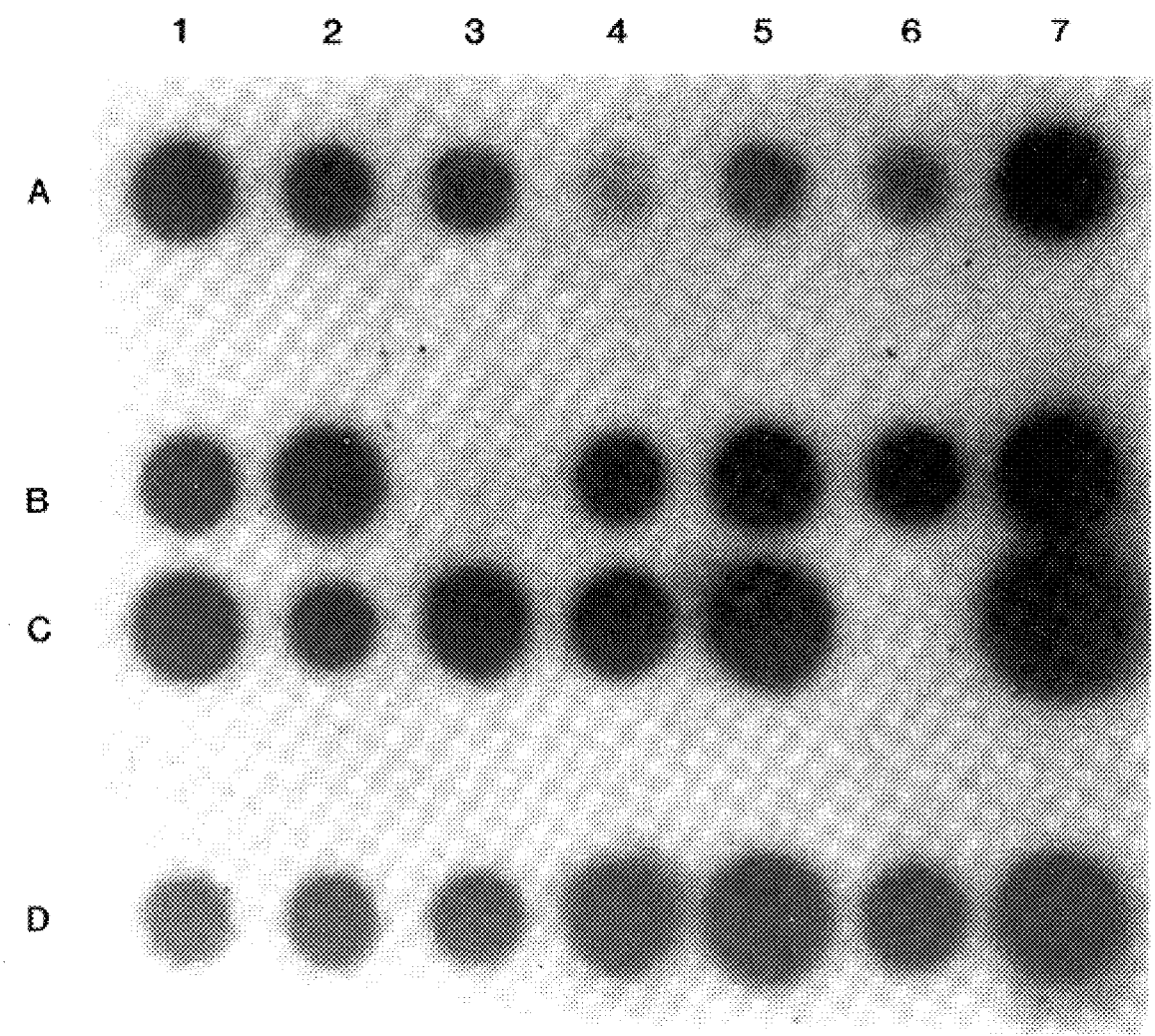

DNA from 24 bacteriophages isolated from *P. multocida* strains and all shown to be different in their lysis patterns towards a range of *P. multocida* strains were bound to a nylon filter by dot blotting. The plasmid pLOA03 was radioactively labelled by nicktranslation, and used as a probe against the filter. Hybridization and washing conditions were as described above. The results are shown in FIG. 22. The probe hybridized to 22 out of 24 bacteriophages and, as expected, to the four positive controls. By using pSPE308 and pLOB03 as probes, similar results were obtained. pSPE312 gave only a slight hybridzation to some of the bacteriophage genomes. The 4.5 kb pmt gene containing ClaI-PvuII fragment of pSPE312 (FIG. 5) did not show any homology to any of the bacteriophage genomes (autoradiographs are not shown).

These results show that there are sequences homologous to *P. multocida* bacteriophage DNA on both sides of the pmt gene. This further substantiates the notion that the pmt gene is carried by a prophage.

BIBLIOGRAPHY

1. K. B. Pedersen and K. Barfod, 1981. The aetiological significance of *Bordetella bronchiseptica* amd *P. multocida* in atrophic rhinitis of swine. *Nord. Vet.-Med.* 33: pp. 513–522.

2. J. M. Rutter and X. Rojas, 1982. Atrophic rhinitis in piglets: Differences in the pathogenicity of *Pasteurella multocida* in combined infections with *Bordetella bronchiseptica*. *Vet. Rec.* 110: pp. 531–535.
3. F. Elling and K. B. Pedersen, 1985. The pathogenesis of persistent turbinate atrophy induced by toxigenic *Pasteurella multocida* in pigs. *Vet. Pathol.* 22: pp. 469–474.
4. K. B. Pedersen, J. P. Nielsen, N. T. Foged, F. Elling, N. C. Nielsen and P. Willeberg, 1988. Atrophic rhinitis in pigs: Proposal for a revised definition. *Vet. Rec.* 22: pp. 490–491.
5. K. B. Pedersen and F. Elling, 1984. The pathogenesis of atrophic rhinitis in pigs induced by toxigenic *Pasteurella multocida*. *J. Comp. Pathol.* 94: pp. 203–214.
6. N. T. Foged, K. B. Pedersen and F. Elling, 1987, Characterization and biological effect of the *P. multocida* toxin. *FEMS Microbiol. Lett.* 43: pp. 45–51.
7. E. M. Kamp, P. J. v.d. Heijden and B. J. Tetenburg, 1987, Purification of a heat labile dermonecrotic toxin from culture fluid of *Pasteurella multocida*. *Vet. Microbiol.* 13: pp. 235–248.
8. T. Nakai, A. Sawata, M. Tsuji, Y. Samejima and K. Kume, 1984. Purification of dermonecrotic toxin from a sonic extract of *Pasteurella multocida* SP-72 *serotype D*. *Infect. Immun.* 46: pp. 429–434.
9. C. L. Trummel, J. O. Cisar, M. J. Pabst and P. Goforth, 1979. Stimulation of bone resorption by a factor from Actinomyces viscosus. *J. Perdont. Res.* 14: pp. 263–264.
10. P. A. Price, 1987. Structure and function of vitamin K-dependent bone proteins. In: C. Christiansen, J. S. Johansen, B. J. Riis (eds.) Osteoporosis, Nørhaven A/S, Viborg, Denmark, pp. 656–663.
11. Casadaban and S. Cohen, 1980. Analysis of gene control signals by DNA fusion and cloning in *Escherichia coli: J. Mol. Biol.* 16: pp. 118–133.
12. J. Mestecky, 1987. The common mucosal immune system and current strategies for induction of immune response in external secretions. *J. Clin. Immunol.* 7 (4): pp. 265–276.
13. H. W. D. Matthes, W. H. Zenke, T. Grundström, A. Staub, M. Wintzerith and P. Chambon, 1984. Simultaneous rapid chemical synthesis of over 100 oligonucleotides on a microscale. The *EMBO Journal* 3: pp. 801–805.
14. 14. T. Maniatis, E. F. Frisch and J. Sambrook, 1982. Molecular cloning. Cold Spring Harbor Laboratory, Cold Spring Harbor, N.Y.
15. 15. G. Köhler and C. Milstein, 1975. Continuous cultures of fused cells secreting antibody of predefined specificity. *Nature*, 256: pp. 495–497.
16. C. Klein, J. Luka and J. Zeuthen, 1980. Transformation induced by Epstein-Barr virus and the role of the nuclear antigen. *Cold Spring Harbor Symp. Quant. Biol.* 44: pp. 253–261.
17. J. W. Goding, 1983. Monoclonal antibodies: Principles and practice. Academic Press, London, 267 pages.
18. E. Southern, 1975, Detection of specific sequences among DN BA fragments separated by gel electrophoresis. *J. Mol. Biol.* 98, pp. 503.
19. Rigby, P. W. J., Dieckmann, M., Rhodes, C., and Berg, P. 1977. Labelling deoxyribonucleic acid to high specific activity in vitro by nick translation with DNA polymerase. I.*J.Mol.Biol.* 113: pp. 237–251.
20. Gebeyechu, G., Rao, P. Y., SooChan, P., Simms, D. A., and Klevan, L. 1987. Novel biotinylated nucleoticle— analogs for labelling and colorimetric detection of DNA. *Nucleic Acids Res.* 15: p.p. 4513–4534.
21. R. K. Saiki, S. J. Scharf, F. Faloona, K. B. Mullis, G. T. Horn, H. A. Ehrlich and N. A. Arnhiem, 1985. Enzymatic amplification of β-globin genomic sequences and restriction site analysis for diagnosis of sickle-cell anemia. *Science* 230: pp. 1350–1354.
22. J. P. Nielsen, M. Bisgaard, and K. B. Pedersen, 1986, Production of toxin in strains previously classified as *P. multocida*. *Acta Path. Microbiol. Immunol. Scand. Sec. B,* 94: pp. 203–204.
23. S. Fazekas, Groth, S. and D. Scheidegger, Production of monoclonal antibodies: Strategy and tactics, *J. Immunol. Meth.* 35, 1980, pp. 1–21.
24. U.K. Laemmli, 1970. Cleavage of structural proteins during the assembly of the head of bacteriophage T4. *Nature* 227: pp. 680–685.
25. J. Kyhse-Andersen, 1984, Electroblotting of multiple gels: A simple apparatus without buffer tank for rapid transfer of proteins from polyacrylamide to nitrocellulose. *J. Biochem. Biophys. Methods* 10: pp. 203–209.
26. O. J. Bjerrum, K. P. Larsen and M. Wilken, 1983. Some recent developments of the electroimmunochemical analysis of membrane proteins. Application of Zwittergent, Triton X-114 and western blotting technique, pp. 79–124. In H. Tschesche (ed.), Modern methods in protein chemistry. Walther de Gruyter Berlin, New York.
27. L. J. Anderson, J. C. Hierholzer, Y. O. Stone, C. Tsou and B. F. Fernie, 1986. Identification of epitopes on respiratory syncytial virus proteins by competitive binding immunoassay. *J. Clin. Microbiol.* 23: pp. 475–480.
28. J. L. Guesdon, T. Ternynck and T. Avrameas, 1979. The use of avidin-biotin interaction in immunoenzymatic techniques. *J. Histochem. Cytochem.* 27: pp. 1131–1139.
29. H. Towbin, T. Staehlin and J. Gordon, 1979, Electrophoretic transfer of proteins from polyacrylamide gel to nitrocellulose sheets: Procedure and applications. *Proc. Natl. Acad. Sci.* USA 76: pp. 4350–4354.
30. M. J. Casabadan and S. Cohen, 1980. Analysis of gene control signals by DNA fusion and cloning in *Escherichia coli. J. Mol. Biol.* 138: pp. 179–207.
31. W. B. Wood, 1966. Host specificity of DNA produced by *Escherichia coli:* Bacterial mutations affecting the restriction and modification of DNA. *J. Mol. Biol.* 16: pp. 118–133.
32. B. Nilsson, M. Uhlen, S. Josephson, S. Gatenbeck and L. Philipson, 1983, An improved positive selection plasmid vector constructed by oligonucleotide mediated mutagenesis, *Nucleic Acids Res.* 11(22): pp. 8019–8030.
33. F. Sanger, S. Nicklin and A. R. Coulson, 1977. DNA sequencing with chain-terminating inhibitors. *Proc. Natl. Acad. Sci.* USA 74: pp. 5463–5467.
34. D. J. Clark and O. Maaløe, 1967. DNA replication and the division cycle in *Escherichia coli. J. Mol. Biol.* 23:99–112.
35. K. K. Stanley, 1983, Solubilization and immunedetection of β-galactosidase hybrid proteins carrying foreign antigenic determinants. *Nucleic Acids Res.* 11(12): pp. 4077–4092.
36. J. M. Rutter, 1983. Virulence of *Pasteurella multocida* in atrophic rhinitis of gnotobiotic pigs infected with *Bordetella bronchiseptica*. *Res. Vet. Sci.* 34: pp. 287–295.
37. K. Kaiser and N. Murry, 1985: The use of phage lambda replacement vectors in the construction of representative genomic DNA libraries. In: DNA cloning, Vol. I, A practical approach, D. M. Glover (ed.) IRL Press, Oxford.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 4380 base pairs
       (B) TYPE: nucleic acid
       (C) STRANDEDNESS: double
       (D) TOPOLOGY: linear (ix) FEATURE:
       (A) NAME/KEY: CDS
       (B) LOCATION: 219..4076

(xi) SEQUENCE DESCRIPTION: SEQ ID NO:1:

```
AACAAGGGAA AATAGCTAGA TTAGACGATA TCGATAATAT CATAAATAAT ATTTAAAAAT      60

TACGCCCCTT GACCTAGAGG GGCTTTTTTA TTACATCAAA AAAATAAACC CAAACACTGC     120

GAATGTTTGG GGTTTTATTT ATAACCAAAA TACATTAATA TGTTTATTAA GTAAGCATTA     180

TCTTACTTTA GGAATAAACT AACATAGAGG TTATGGAT ATG AAA ACA AAA CAT         233
                                          Met Lys Thr Lys His
                                            1               5

TTT TTT AAC TCA GAT TTT ACT GTA AAA GGA AAA AGT GCC GAT GAA ATT       281
Phe Phe Asn Ser Asp Phe Thr Val Lys Gly Lys Ser Ala Asp Glu Ile
            10                  15                  20

TTT AGA AGA TTG TGT ACT GAT CAT CCT GAC AAG CAA TTA AAC AAT GTA       329
Phe Arg Arg Leu Cys Thr Asp His Pro Asp Lys Gln Leu Asn Asn Val
        25                  30                  35

AAA TGG AAA GAA GTT TTT ATT AAT CGT TTT GGT CAG ATG ATG CTA GAT       377
Lys Trp Lys Glu Val Phe Ile Asn Arg Phe Gly Gln Met Met Leu Asp
    40                  45                  50

ACT CCT AAT CCG AGA AAG ATT GTA GAA AAA ATT ATT AAT GAA GGG CTT       425
Thr Pro Asn Pro Arg Lys Ile Val Glu Lys Ile Ile Asn Glu Gly Leu
55                  60                  65

GAA AAA CAA GGC CTG AAA AAT ATA GAT CCT GAA ACT ACA TAT TTC AAC       473
Glu Lys Gln Gly Leu Lys Asn Ile Asp Pro Glu Thr Thr Tyr Phe Asn
70                  75                  80                  85

ATT TTT TCA TCT TCT GAC AGC TCC GAT GGG AAC GTT TTT CAT TAT AAC       521
Ile Phe Ser Ser Ser Asp Ser Ser Asp Gly Asn Val Phe His Tyr Asn
                90                  95                 100

TCT TTA TCA GAA TCC TAT CGA GTT ACT GAT GCC TGC CTA ATG AAT ATT       569
Ser Leu Ser Glu Ser Tyr Arg Val Thr Asp Ala Cys Leu Met Asn Ile
            105                 110                 115

TTT GTG GAG CGT TAT TTT GAT GAT TGG GAC TTG CTA AAT AGC TTA GCC       617
Phe Val Glu Arg Tyr Phe Asp Asp Trp Asp Leu Leu Asn Ser Leu Ala
        120                 125                 130

AGT AAT GGA ATA TAT TCA GTA GGA AAA GAA GGA GCT TAT TAT CCT GAT       665
Ser Asn Gly Ile Tyr Ser Val Gly Lys Glu Gly Ala Tyr Tyr Pro Asp
    135                 140                 145

CAT GAT TAT GGT CCA GAA TAT AAC CCT GTT TGG GGA CCA AAC GAA CAA       713
His Asp Tyr Gly Pro Glu Tyr Asn Pro Val Trp Gly Pro Asn Glu Gln
150                 155                 160                 165

ATT TAC CAT TCT AGA GTG ATT GCA GAT ATC CTT TAT GCT CGC TCC GTA       761
Ile Tyr His Ser Arg Val Ile Ala Asp Ile Leu Tyr Ala Arg Ser Val
                170                 175                 180

TGG GAT GAA TTT AAA AAA TAC TTC ATG GAG TAT TGG CAA AAA TAT GCT       809
Trp Asp Glu Phe Lys Lys Tyr Phe Met Glu Tyr Trp Gln Lys Tyr Ala
            185                 190                 195
```

-continued

| | |
|---|---|
| CAG CTT TAT ACC GAA ATG TTA TCT GAT ACA TTT CTT GCA ATG GCT ATT<br>Gln Leu Tyr Thr Glu Met Leu Ser Asp Thr Phe Leu Ala Met Ala Ile<br>        200                      205                   210 | 857 |
| CAG CAA TAT ACA CGA CAA ACG CTT ACT GAT GAA GGC TTT CTT ATG GTT<br>Gln Gln Tyr Thr Arg Gln Thr Leu Thr Asp Glu Gly Phe Leu Met Val<br>        215                      220                   225 | 905 |
| TGT AAC ACA TAT TAT GGC AAT AAG GAA GAA GTT CAA ATA ACT CTA CTA<br>Cys Asn Thr Tyr Tyr Gly Asn Lys Glu Glu Val Gln Ile Thr Leu Leu<br>230                      235                   240                 245 | 953 |
| GAT ATC TAT GGA TAC CCT TCC ACT GAT ATA ATT TGT ATA GAG CAA AAA<br>Asp Ile Tyr Gly Tyr Pro Ser Thr Asp Ile Ile Cys Ile Glu Gln Lys<br>                250                   255                 260 | 1001 |
| GGG CTT CCT ACT CCT AAA GTG ATA CTT TAC ATT CCT GGA GGA ACA CAA<br>Gly Leu Pro Thr Pro Lys Val Ile Leu Tyr Ile Pro Gly Gly Thr Gln<br>                265                   270                 275 | 1049 |
| CCA TTT GTT GAA TTT CTT AAT ACA GAT GAT CTG AAA CAA TGG ATT GCA<br>Pro Phe Val Glu Phe Leu Asn Thr Asp Asp Leu Lys Gln Trp Ile Ala<br>                  280                   285                 290 | 1097 |
| TGG CAT TTA AAA GAT AAC AAA CAT ATG GTC CGA TTC CGC AAA CAT TTC<br>Trp His Leu Lys Asp Asn Lys His Met Val Arg Phe Arg Lys His Phe<br>        295                      300                   305 | 1145 |
| TCG CTA AAA CAA CGT CAG GAA GGA GAA ACG TTT ACA GGT ATA GAT AAA<br>Ser Leu Lys Gln Arg Gln Glu Gly Glu Thr Phe Thr Gly Ile Asp Lys<br>310                      315                   320                 325 | 1193 |
| GCA CTT CAA TAT ATT GCA GAA GAG TCC CCT GAA TGG CCT GCC AAT AAA<br>Ala Leu Gln Tyr Ile Ala Glu Glu Ser Pro Glu Trp Pro Ala Asn Lys<br>                  330                   335                 340 | 1241 |
| TAC ATC CTT TAT AAT CCG ACA CAT TTA GAA ACA GAA AAT TTA TTT AAC<br>Tyr Ile Leu Tyr Asn Pro Thr His Leu Glu Thr Glu Asn Leu Phe Asn<br>                345                   350                 355 | 1289 |
| ATC ATG ATG AAG CGA ACA GAA CAG CGG ATG CTT GAA GAT AGT GAT GTA<br>Ile Met Met Lys Arg Thr Glu Gln Arg Met Leu Glu Asp Ser Asp Val<br>                  360                   365                 370 | 1337 |
| CAG ATT AGA TCA AAT TCA GAA GCT ACC CGT GAC TAT GCT CTT TCA TTA<br>Gln Ile Arg Ser Asn Ser Glu Ala Thr Arg Asp Tyr Ala Leu Ser Leu<br>        375                      380                   385 | 1385 |
| CTC GAA ACC TTT ATT TCA CAG TTA TCT GCA ATA GAT ATG TTA GTA CCA<br>Leu Glu Thr Phe Ile Ser Gln Leu Ser Ala Ile Asp Met Leu Val Pro<br>390                      395                   400                 405 | 1433 |
| GCA GTA GGT ATC CCA ATT AAT TTT GCC CTA TCA GCT ACA GCA TTA GGA<br>Ala Val Gly Ile Pro Ile Asn Phe Ala Leu Ser Ala Thr Ala Leu Gly<br>                  410                   415                 420 | 1481 |
| CTT AGC TCG GAT ATT GTA GTT AAT GGA GAT TCA TAT GAA AAG AGA AAA<br>Leu Ser Ser Asp Ile Val Val Asn Gly Asp Ser Tyr Glu Lys Arg Lys<br>                425                   430                 435 | 1529 |
| TAT GGA ATT GGG TCC TTA GTG CAA TCT GCA TTA TTC ACA GGA ATT AAT<br>Tyr Gly Ile Gly Ser Leu Val Gln Ser Ala Leu Phe Thr Gly Ile Asn<br>                440                   445                 450 | 1577 |
| CTT ATT CCA GTT ATT TCG GAA ACC GCA GAA ATT TTA TCT TCT TTC TCT<br>Leu Ile Pro Val Ile Ser Glu Thr Ala Glu Ile Leu Ser Ser Phe Ser<br>455                      460                   465 | 1625 |
| AGA ACA GAA GAA GAT ATT CCA GCT TTT TTC ACT GAA GAA CAA GCT TTA<br>Arg Thr Glu Glu Asp Ile Pro Ala Phe Phe Thr Glu Glu Gln Ala Leu<br>470                      475                   480                 485 | 1673 |
| GCT CAA CGC TTT GAA ATA GTA GAA GAA GAA TTA CAT TCT ATC TCA CCT<br>Ala Gln Arg Phe Glu Ile Val Glu Glu Glu Leu His Ser Ile Ser Pro<br>                490                   495                 500 | 1721 |
| GAT GAT CCT CCT CGA GAA ATT ACT GAC GAA AAT TTA CAT AAA ATT CGT<br>Asp Asp Pro Pro Arg Glu Ile Thr Asp Glu Asn Leu His Lys Ile Arg | 1769 |

-continued

```
            505                 510                 515
CTG GTA CGT CTT AAC AAT GAA AAT CAA CCT TTA GTT GTG TTA CGA AGA          1817
Leu Val Arg Leu Asn Asn Glu Asn Gln Pro Leu Val Val Leu Arg Arg
        520                 525                 530

TTA GGA GGA AAT AAA TTT ATC AGA ATC GAG CCT ATA ACA TTC CAG GAA          1865
Leu Gly Gly Asn Lys Phe Ile Arg Ile Glu Pro Ile Thr Phe Gln Glu
    535                 540                 545

ATA AAA GGT TCT TTA GTA AGT GAA GTT ATA AAT CCA GTG ACT AAT AAA          1913
Ile Lys Gly Ser Leu Val Ser Glu Val Ile Asn Pro Val Thr Asn Lys
550                 555                 560                 565

ACG TAC TAC GTA AGC AAT GCT AAA CTA TTA GGG GGC TCT CCT TAT AGT          1961
Thr Tyr Tyr Val Ser Asn Ala Lys Leu Leu Gly Gly Ser Pro Tyr Ser
                570                 575                 580

CCT TTC CGT ATT GGA TTA GAA GGT GTT TGG ACA CCA GAG GTA TTA AAA          2009
Pro Phe Arg Ile Gly Leu Glu Gly Val Trp Thr Pro Glu Val Leu Lys
            585                 590                 595

GCA AGA GCT TCC GTT ATT GGA AAG CCT ATT GGA GAA TCA TAT AAA AGA          2057
Ala Arg Ala Ser Val Ile Gly Lys Pro Ile Gly Glu Ser Tyr Lys Arg
        600                 605                 610

ATA TTA GCC AAA CTA CAA AGA ATA CAT AAC AGT AAT ATC TTA GAT GAG          2105
Ile Leu Ala Lys Leu Gln Arg Ile His Asn Ser Asn Ile Leu Asp Glu
    615                 620                 625

CGA CAA GGT TTA ATG CAT GAA CTC ATG GAG CTT ATT GAT CTT TAT GAA          2153
Arg Gln Gly Leu Met His Glu Leu Met Glu Leu Ile Asp Leu Tyr Glu
630                 635                 640                 645

GAA TCG CAA CCT TCT TCA GAG CGT TTG AAT GCT TTT CGT GAA CTG CGT          2201
Glu Ser Gln Pro Ser Ser Glu Arg Leu Asn Ala Phe Arg Glu Leu Arg
                650                 655                 660

ACT CAA TTA GAA AAA GCG CTT TAT CTT CCT GAA ATG GAA GCA TTA AAA          2249
Thr Gln Leu Glu Lys Ala Leu Tyr Leu Pro Glu Met Glu Ala Leu Lys
            665                 670                 675

AAA CAA ATA CTA CAG ATT CCT AAC AAA GGT TCT GGT GCC GCT CGA TTT          2297
Lys Gln Ile Leu Gln Ile Pro Asn Lys Gly Ser Gly Ala Ala Arg Phe
        680                 685                 690

TTA CTT CGT ACA GCC ATG AAT GAA ATG GCT GGA AAA ACC AGT GAA AGC          2345
Leu Leu Arg Thr Ala Met Asn Glu Met Ala Gly Lys Thr Ser Glu Ser
    695                 700                 705

ACG GCT GAT TTA ATA CGC TTT GCC TTG CAA GAT ACA GTA ATT TCA GCG          2393
Thr Ala Asp Leu Ile Arg Phe Ala Leu Gln Asp Thr Val Ile Ser Ala
710                 715                 720                 725

CCT TTT CGC GGA TAT GCT GGT GCG ATT CCA GAG GCA ATA GAC TTT CCT          2441
Pro Phe Arg Gly Tyr Ala Gly Ala Ile Pro Glu Ala Ile Asp Phe Pro
                730                 735                 740

GTA AAA TAT GTA ATA GAA GAC ATA TCT GTA TTT GAT AAA ATA CAG ACA          2489
Val Lys Tyr Val Ile Glu Asp Ile Ser Val Phe Asp Lys Ile Gln Thr
            745                 750                 755

AAT TAC TGG GAA CTT CCT GCT TAT GAA AGC TGG AAC GAA GGA AGT AAT          2537
Asn Tyr Trp Glu Leu Pro Ala Tyr Glu Ser Trp Asn Glu Gly Ser Asn
        760                 765                 770

AGC CGA TTA CTG CCT GGT TTG TTA CGT GAA TCG CAA AGC AAG GGG ATG          2585
Ser Arg Leu Leu Pro Gly Leu Leu Arg Glu Ser Gln Ser Lys Gly Met
    775                 780                 785

TTA AGT AAG TGT CGT ATC ATA GAA AAT AGC CTT TAT ATT GGA CAT AGC          2633
Leu Ser Lys Cys Arg Ile Ile Glu Asn Ser Leu Tyr Ile Gly His Ser
790                 795                 800                 805

TAT GAA GAA ATG TTT TAC AGC ATT TCT CCA TAT TCA AAC CAG GTT GGA          2681
Tyr Glu Glu Met Phe Tyr Ser Ile Ser Pro Tyr Ser Asn Gln Val Gly
                810                 815                 820

GGG CCT TAT GAA TTA TAT CCT TTC ACT TTT TTC AGT ATG CTT CAA GAA          2729
```

-continued

```
                Gly Pro Tyr Glu Leu Tyr Pro Phe Thr Phe Phe Ser Met Leu Gln Glu
                        825                 830                 835

GTA CAA GGT GAT TTA GGA TTT GAG CAG GCC TTT GCC ACA CGT AAC TTT             2777
Val Gln Gly Asp Leu Gly Phe Glu Gln Ala Phe Ala Thr Arg Asn Phe
        840                 845                 850

TTC AAT ACT CTT GTT TCT GAT CGA CTA TCC TTA ATG GAA AAT ACG ATG             2825
Phe Asn Thr Leu Val Ser Asp Arg Leu Ser Leu Met Glu Asn Thr Met
855                 860                 865

TTA CTT ACA GAA AGT TTT GAT TAT ACA CCT TGG GAT GCT ATT TAT GGA             2873
Leu Leu Thr Glu Ser Phe Asp Tyr Thr Pro Trp Asp Ala Ile Tyr Gly
870                 875                 880                 885

GAT ATT AAT TAT GAT GAA CAA TTT GCT GCA ATG TCT ATT AAT GAA CGC             2921
Asp Ile Asn Tyr Asp Glu Gln Phe Ala Ala Met Ser Ile Asn Glu Arg
                890                 895                 900

ATA GAA AAA TGT ATG AAT ACC TAT AGA GGT GTG GCA TTC CAA AAC TCT             2969
Ile Glu Lys Cys Met Asn Thr Tyr Arg Gly Val Ala Phe Gln Asn Ser
        905                 910                 915

TCA AAA AGT ATT GAC TTT TTC CTA AAT AAT CTA ACC ACA TTC ATT GAT             3017
Ser Lys Ser Ile Asp Phe Phe Leu Asn Asn Leu Thr Thr Phe Ile Asp
920                 925                 930

AAT GGA CTA ACC GAA ATT GCT ATA TCT GAT TTA CCG TAT GAT ATT GTG             3065
Asn Gly Leu Thr Glu Ile Ala Ile Ser Asp Leu Pro Tyr Asp Ile Val
935                 940                 945

CAA CAA GAA ATC TCT CAA TTC TTA CAA GGA AGT AAT GAA TGG AAA ACA             3113
Gln Gln Glu Ile Ser Gln Phe Leu Gln Gly Ser Asn Glu Trp Lys Thr
950                 955                 960                 965

CTT GAT GCC ATG TTA TTT AAC TTA GAT AAA GGA GAT ATT AAT GGT GCT             3161
Leu Asp Ala Met Leu Phe Asn Leu Asp Lys Gly Asp Ile Asn Gly Ala
                970                 975                 980

TTC AGA AAG CTT CTG CAA TCA GCA AAA GAT AAT AAT ATA AAA TTT AGA             3209
Phe Arg Lys Leu Leu Gln Ser Ala Lys Asp Asn Asn Ile Lys Phe Arg
        985                 990                 995

GCT ATA GGG CAT TCA GAT AAT TCT GTT CCG CCA TTT AAT AAC CCT TAT             3257
Ala Ile Gly His Ser Asp Asn Ser Val Pro Pro Phe Asn Asn Pro Tyr
        1000                1005                1010

AAG TCT TTA TAT TAT AAA GGA AAT ATA ATA GCT GAA GCA ATT GAA AAA             3305
Lys Ser Leu Tyr Tyr Lys Gly Asn Ile Ile Ala Glu Ala Ile Glu Lys
        1015                1020                1025

CTA GAT CGA GAA GGT CAA AAA TTT GTT GTA TTT GCT GAT AGT TCT CTG             3353
Leu Asp Arg Glu Gly Gln Lys Phe Val Val Phe Ala Asp Ser Ser Leu
1030                1035                1040                1045

CTC AAC AGC ACG CCT GGG ACA GGT CGT CCT ATG CCA GGA CTA GTT CAA             3401
Leu Asn Ser Thr Pro Gly Thr Gly Arg Pro Met Pro Gly Leu Val Gln
                1050                1055                1060

TAT TTA AAA ATA CCA GCA ACT GTA GTA GAT AGC GAT GGT GCA TGG CAA             3449
Tyr Leu Lys Ile Pro Ala Thr Val Val Asp Ser Asp Gly Ala Trp Gln
        1065                1070                1075

TTT CTT CCA GAT GTA GCT TCA AGC AGA GTT CCT ATT GAA GTT ACA GAG             3497
Phe Leu Pro Asp Val Ala Ser Ser Arg Val Pro Ile Glu Val Thr Glu
        1080                1085                1090

TTA GAA AAT TGG CAA GTC TTA ACT CCT CCA CAA GGT AAG ATT CTT GGA             3545
Leu Glu Asn Trp Gln Val Leu Thr Pro Pro Gln Gly Lys Ile Leu Gly
        1095                1100                1105

TTA AAG CAA TTT AAG TTA ACG GCA GGT TTT CCA ACA GAA CAA AGT CGC             3593
Leu Lys Gln Phe Lys Leu Thr Ala Gly Phe Pro Thr Glu Gln Ser Arg
1110                1115                1120                1125

TTA CCT CTT TTA GAG AAT TCG GTT TCT GAA GAT TTA AGG GAA GAA TTA             3641
Leu Pro Leu Leu Glu Asn Ser Val Ser Glu Asp Leu Arg Glu Glu Leu
                1130                1135                1140
```

-continued

```
ATG CAA AAG ATT GAT GCA ATA AAA AAT GAT GTG AAA ATG AAT AGT TTA      3689
Met Gln Lys Ile Asp Ala Ile Lys Asn Asp Val Lys Met Asn Ser Leu
        1145                1150                1155

GTG TGT ATG GAA GCT GGC TCT TGT GAT TCA GTA AGC CCT AAG GTA GCT      3737
Val Cys Met Glu Ala Gly Ser Cys Asp Ser Val Ser Pro Lys Val Ala
        1160                1165                1170

GCC CGT CTT AAA GAT ATG GGG TTA GAA GCT GGG ATG GGT GCT TCT ATT      3785
Ala Arg Leu Lys Asp Met Gly Leu Glu Ala Gly Met Gly Ala Ser Ile
        1175                1180                1185

ACC TGG TGG AGA CGT GAA GGC GGG ATG GAA TTT TCA CAT CAG ATG CAT      3833
Thr Trp Trp Arg Arg Glu Gly Gly Met Glu Phe Ser His Gln Met His
1190                1195                1200                1205

ACT ACT GCT TCC TTT AAA TTT GCT GGT AAA GAG TTT GCC GTG GAT GCT      3881
Thr Thr Ala Ser Phe Lys Phe Ala Gly Lys Glu Phe Ala Val Asp Ala
        1210                1215                1220

TCA CAT TTA CAA TTT GTA CAC GAC CAA TTA GAT ACA ACT ATC CTG ATA      3929
Ser His Leu Gln Phe Val His Asp Gln Leu Asp Thr Thr Ile Leu Ile
        1225                1230                1235

CTA CCT GTA GAT GAT TGG GCT TTA GAA ATA GCT CAA AGA AAT CGG GCT      3977
Leu Pro Val Asp Asp Trp Ala Leu Glu Ile Ala Gln Arg Asn Arg Ala
        1240                1245                1250

ATT AAT CCT TTT GTG GAA TAT GTT AGT AAA ACA GGA AAC ATG TTA GCA      4025
Ile Asn Pro Phe Val Glu Tyr Val Ser Lys Thr Gly Asn Met Leu Ala
        1255                1260                1265

CTC TTC ATG CCT CCT CTT TTC ACA AAG CCT CGC TTA ACA AGA GCA CTA      4073
Leu Phe Met Pro Pro Leu Phe Thr Lys Pro Arg Leu Thr Arg Ala Leu
1270                1275                1280                1285

TAACTAATTA AAAACTGTAT TAAAGCCTTA TATTATAAGG CTTTAATTTT CTTTCAAGAA    4133

TTATTAAGTA GAAGAATCAA AATCAATGAG ATAGATAAAA TCAAATGTTA TTACCAATAC    4193

AACTTTCTTA AGTATACTTT TTGAATTTTT TGCGTTAATA AATTTATAAT ACCCTTAACT    4253

CAATAAAAGA AGTTATTGAG AAGTTTAAAT CTTGTGAGCA AGATGAAGAT ATAATTTCAG    4313

CAATCGATCT TATTAGCGCT TCATATAGAA GGGCTGTGGA TGCAGTGGAA CAAAGATTCG    4373

GTTCTAG                                                              4380
```

(2) INFORMATION FOR SEQ ID NO:2:

(i) SEQUENCE CHARACTERISTICS:
        (A) LENGTH: 1285 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Thr Lys His Phe Phe Asn Ser Asp Phe Thr Val Lys Gly Lys
 1               5                  10                  15

Ser Ala Asp Glu Ile Phe Arg Arg Leu Cys Thr Asp His Pro Asp Lys
             20                  25                  30

Gln Leu Asn Asn Val Lys Trp Lys Glu Val Phe Ile Asn Arg Phe Gly
         35                  40                  45

Gln Met Met Leu Asp Thr Pro Asn Pro Arg Lys Ile Val Glu Lys Ile
     50                  55                  60

Ile Asn Glu Gly Leu Glu Lys Gln Gly Leu Lys Asn Ile Asp Pro Glu
 65                  70                  75                  80

Thr Thr Tyr Phe Asn Ile Phe Ser Ser Asp Ser Ser Asp Gly Asn
                 85                  90                  95

Val Phe His Tyr Asn Ser Leu Ser Glu Ser Tyr Arg Val Thr Asp Ala
```

-continued

```
                100                 105                 110
Cys Leu Met Asn Ile Phe Val Glu Arg Tyr Phe Asp Asp Trp Asp Leu
            115                 120                 125
Leu Asn Ser Leu Ala Ser Asn Gly Ile Tyr Ser Val Gly Lys Glu Gly
            130                 135                 140
Ala Tyr Tyr Pro Asp His Asp Tyr Gly Pro Glu Tyr Asn Pro Val Trp
145                 150                 155                 160
Gly Pro Asn Glu Gln Ile Tyr His Ser Arg Val Ile Ala Asp Ile Leu
                165                 170                 175
Tyr Ala Arg Ser Val Trp Asp Glu Phe Lys Lys Tyr Phe Met Glu Tyr
                180                 185                 190
Trp Gln Lys Tyr Ala Gln Leu Tyr Thr Glu Met Leu Ser Asp Thr Phe
            195                 200                 205
Leu Ala Met Ala Ile Gln Gln Tyr Thr Arg Gln Thr Leu Thr Asp Glu
            210                 215                 220
Gly Phe Leu Met Val Cys Asn Thr Tyr Tyr Gly Asn Lys Glu Glu Val
225                 230                 235                 240
Gln Ile Thr Leu Leu Asp Ile Tyr Gly Tyr Pro Ser Thr Asp Ile Ile
                245                 250                 255
Cys Ile Glu Gln Lys Gly Leu Pro Thr Pro Lys Val Ile Leu Tyr Ile
            260                 265                 270
Pro Gly Gly Thr Gln Pro Phe Val Glu Phe Leu Asn Thr Asp Asp Leu
            275                 280                 285
Lys Gln Trp Ile Ala Trp His Leu Lys Asp Asn Lys His Met Val Arg
            290                 295                 300
Phe Arg Lys His Phe Ser Leu Lys Gln Arg Gln Glu Gly Glu Thr Phe
305                 310                 315                 320
Thr Gly Ile Asp Lys Ala Leu Gln Tyr Ile Ala Glu Glu Ser Pro Glu
                325                 330                 335
Trp Pro Ala Asn Lys Tyr Ile Leu Tyr Asn Pro Thr His Leu Glu Thr
                340                 345                 350
Glu Asn Leu Phe Asn Ile Met Met Lys Arg Thr Glu Gln Arg Met Leu
            355                 360                 365
Glu Asp Ser Asp Val Gln Ile Arg Ser Asn Ser Glu Ala Thr Arg Asp
            370                 375                 380
Tyr Ala Leu Ser Leu Leu Glu Thr Phe Ile Ser Gln Leu Ser Ala Ile
385                 390                 395                 400
Asp Met Leu Val Pro Ala Val Gly Ile Pro Ile Asn Phe Ala Leu Ser
                405                 410                 415
Ala Thr Ala Leu Gly Leu Ser Ser Asp Ile Val Val Asn Gly Asp Ser
            420                 425                 430
Tyr Glu Lys Arg Lys Tyr Gly Ile Gly Ser Leu Val Gln Ser Ala Leu
            435                 440                 445
Phe Thr Gly Ile Asn Leu Ile Pro Val Ile Ser Glu Thr Ala Glu Ile
            450                 455                 460
Leu Ser Ser Phe Ser Arg Thr Glu Glu Asp Ile Pro Ala Phe Phe Thr
465                 470                 475                 480
Glu Glu Gln Ala Leu Ala Gln Arg Phe Glu Ile Val Glu Glu Glu Leu
                485                 490                 495
His Ser Ile Ser Pro Asp Asp Pro Arg Glu Ile Thr Asp Glu Asn
                500                 505                 510
Leu His Lys Ile Arg Leu Val Arg Leu Asn Asn Glu Asn Gln Pro Leu
            515                 520                 525
```

-continued

Val Val Leu Arg Arg Leu Gly Gly Asn Lys Phe Ile Arg Ile Glu Pro
        530                 535                 540

Ile Thr Phe Gln Glu Ile Lys Gly Ser Leu Val Ser Glu Val Ile Asn
545                 550                 555                 560

Pro Val Thr Asn Lys Thr Tyr Tyr Val Ser Asn Ala Lys Leu Leu Gly
                565                 570                 575

Gly Ser Pro Tyr Ser Pro Phe Arg Ile Gly Leu Glu Gly Val Trp Thr
                580                 585                 590

Pro Glu Val Leu Lys Ala Arg Ala Ser Val Ile Gly Lys Pro Ile Gly
                595                 600                 605

Glu Ser Tyr Lys Arg Ile Leu Ala Lys Leu Gln Arg Ile His Asn Ser
        610                 615                 620

Asn Ile Leu Asp Glu Arg Gln Gly Leu Met His Glu Leu Met Glu Leu
625                 630                 635                 640

Ile Asp Leu Tyr Glu Glu Ser Gln Pro Ser Ser Glu Arg Leu Asn Ala
                645                 650                 655

Phe Arg Glu Leu Arg Thr Gln Leu Glu Lys Ala Leu Tyr Leu Pro Glu
                660                 665                 670

Met Glu Ala Leu Lys Lys Gln Ile Leu Gln Ile Pro Asn Lys Gly Ser
        675                 680                 685

Gly Ala Ala Arg Phe Leu Leu Arg Thr Ala Met Asn Glu Met Ala Gly
        690                 695                 700

Lys Thr Ser Glu Ser Thr Ala Asp Leu Ile Arg Phe Ala Leu Gln Asp
705                 710                 715                 720

Thr Val Ile Ser Ala Pro Phe Arg Gly Tyr Ala Gly Ala Ile Pro Glu
                725                 730                 735

Ala Ile Asp Phe Pro Val Lys Tyr Val Ile Glu Asp Ile Ser Val Phe
                740                 745                 750

Asp Lys Ile Gln Thr Asn Tyr Trp Glu Leu Pro Ala Tyr Glu Ser Trp
        755                 760                 765

Asn Glu Gly Ser Asn Ser Arg Leu Leu Pro Gly Leu Leu Arg Glu Ser
        770                 775                 780

Gln Ser Lys Gly Met Leu Ser Lys Cys Arg Ile Ile Glu Asn Ser Leu
785                 790                 795                 800

Tyr Ile Gly His Ser Tyr Glu Glu Met Phe Tyr Ser Ile Ser Pro Tyr
                805                 810                 815

Ser Asn Gln Val Gly Gly Pro Tyr Glu Leu Tyr Pro Phe Thr Phe Phe
                820                 825                 830

Ser Met Leu Gln Glu Val Gln Gly Asp Leu Gly Phe Glu Gln Ala Phe
        835                 840                 845

Ala Thr Arg Asn Phe Phe Asn Thr Leu Val Ser Asp Arg Leu Ser Leu
        850                 855                 860

Met Glu Asn Thr Met Leu Leu Thr Glu Ser Phe Asp Tyr Thr Pro Trp
865                 870                 875                 880

Asp Ala Ile Tyr Gly Asp Ile Asn Tyr Asp Glu Gln Phe Ala Ala Met
                885                 890                 895

Ser Ile Asn Glu Arg Ile Glu Lys Cys Met Asn Thr Tyr Arg Gly Val
                900                 905                 910

Ala Phe Gln Asn Ser Ser Lys Ser Ile Asp Phe Phe Leu Asn Asn Leu
        915                 920                 925

Thr Thr Phe Ile Asp Asn Gly Leu Thr Glu Ile Ala Ile Ser Asp Leu
        930                 935                 940

-continued

```
Pro Tyr Asp Ile Val Gln Gln Glu Ile Ser Gln Phe Leu Gln Gly Ser
945                 950                 955                 960

Asn Glu Trp Lys Thr Leu Asp Ala Met Leu Phe Asn Leu Asp Lys Gly
            965                 970                 975

Asp Ile Asn Gly Ala Phe Arg Lys Leu Leu Gln Ser Ala Lys Asp Asn
            980                 985                 990

Asn Ile Lys Phe Arg Ala Ile Gly His Ser Asp Asn Ser Val Pro Pro
            995                 1000                1005

Phe Asn Asn Pro Tyr Lys Ser Leu Tyr Tyr Lys Gly Asn Ile Ile Ala
            1010                1015                1020

Glu Ala Ile Glu Lys Leu Asp Arg Glu Gly Gln Lys Phe Val Val Phe
1025                1030                1035                1040

Ala Asp Ser Ser Leu Leu Asn Ser Thr Pro Gly Thr Gly Arg Pro Met
                1045                1050                1055

Pro Gly Leu Val Gln Tyr Leu Lys Ile Pro Ala Thr Val Val Asp Ser
                1060                1065                1070

Asp Gly Ala Trp Gln Phe Leu Pro Asp Val Ala Ser Ser Arg Val Pro
            1075                1080                1085

Ile Glu Val Thr Glu Leu Glu Asn Trp Gln Val Leu Thr Pro Pro Gln
            1090                1095                1100

Gly Lys Ile Leu Gly Leu Lys Gln Phe Lys Leu Thr Ala Gly Phe Pro
1105                1110                1115                1120

Thr Glu Gln Ser Arg Leu Pro Leu Leu Glu Asn Ser Val Ser Glu Asp
                1125                1130                1135

Leu Arg Glu Glu Leu Met Gln Lys Ile Asp Ala Ile Lys Asn Asp Val
                1140                1145                1150

Lys Met Asn Ser Leu Val Cys Met Glu Ala Gly Ser Cys Asp Ser Val
            1155                1160                1165

Ser Pro Lys Val Ala Ala Arg Leu Lys Asp Met Gly Leu Glu Ala Gly
    1170                1175                1180

Met Gly Ala Ser Ile Thr Trp Trp Arg Arg Glu Gly Gly Met Glu Phe
1185                1190                1195                1200

Ser His Gln Met His Thr Thr Ala Ser Phe Lys Phe Ala Gly Lys Glu
                1205                1210                1215

Phe Ala Val Asp Ala Ser His Leu Gln Phe Val His Asp Gln Leu Asp
                1220                1225                1230

Thr Thr Ile Leu Ile Leu Pro Val Asp Asp Trp Ala Leu Glu Ile Ala
            1235                1240                1245

Gln Arg Asn Arg Ala Ile Asn Pro Phe Val Glu Tyr Val Ser Lys Thr
    1250                1255                1260

Gly Asn Met Leu Ala Leu Phe Met Pro Pro Leu Phe Thr Lys Pro Arg
1265                1270                1275                1280

Leu Thr Arg Ala Leu
                1285
```

What is claimed is:

1. An isolated and purified DNA molecule selected from the group consisting of:

a) a DNA molecule that encodes a polypeptide derivative comprising the amino acid sequence of SEQ ID NO:1, lacking amino acids 1043–1130;

b) a DNA molecule that encodes a polypeptide derivative comprising the amino acid sequence of SEQ ID NO:1, lacking amino acids 1130–1285; and c) a DNA molecule encoding a detoxified polypeptide derivative of *Pasteurella multocida* toxin, wherein the derivative is a truncated form of the toxin and comprises an amino acid sequence that is identical to but shorter than the amino acid sequence of the *Pasteurella multocida* toxin of SEQ ID NO:1, and wherein the toxin derivative specifically binds an antibody that specifically binds *Pasteurella multocida* toxin (PMT).

2. The DNA molecule of claim 1, wherein the antibody is a monoclonal antibody.

3. An isolated and purified DNA molecule selected from the group consisting of a DNA molecule that encodes a polypeptide derivative of *Pasteurella multocida* toxin comprising an amino acid sequence that is identical to but shorter than the amino acid sequence of SEQ ID NO:1, lacking amino acids 1043–1130, and a DNA molecule that encodes a detoxified polypeptide derivative of *Pasteurella multocida* toxin comprising an amino acid sequence that is identical to but shorter than the amino acid sequence of SEQ ID NO:1, lacking amino acids 1130–1285, and wherein the polypeptide derivative specifically binds an antibody that specifically binds *Pasteurella multocida* toxin (PMT).

4. The DNA molecule of claim 3, wherein the antibody is a monoclonal antibody.

5. The DNA molecule of claim 1, wherein the DNA molecule encodes a polypeptide derivative comprising the amino acid sequence of SEQ ID NO:1, lacking amino acids 1043–1130.

6. The DNA molecule of claim 1, wherein the DNA molecule encodes a polypeptide derivative comprising the amino acid sequence of SEQ ID NO:1, lacking amino acids 1130–1285.

7. The DNA molecule of claim 1, further comprising a nucleotide sequence that encodes another polypeptide, wherein the DNA molecule encodes a fusion protein.

8. An expression vector comprising the DNA molecule of claim 1.

9. A microorganism containing the expression vector of claim 8.

10. The microorganism of claim 9, wherein the microorganism is a bacterium.

11. The microorganism of claim 10, wherein the bacterium is *Escherichia coli*.

12. A method for the production of a Pasteurella multocida toxin derivative, comprising the steps:

a) transforming a suitable host microorganism with a DNA molecule according to claim 1;

b) culturing said host microorganism to express a polypeptide derivative;

c) separating said polypeptide derivative from said host microorganism; and d) recovering said polypeptide derivative.

13. The method of claim 12, further comprising the step of testing said recovered polypeptide derivative for toxicity.

* * * * *